United States Patent
Brunicardi et al.

(10) Patent No.: US 11,060,087 B2
(45) Date of Patent: Jul. 13, 2021

(54) SYNTHETIC PROMOTERS FOR HIGH THROUGHPUT SCREENING AND GENE MODULATION

(71) Applicant: The Regents of the University of California, Oakland, CA (US)

(72) Inventors: Francis C. Brunicardi, Pacific Palisades, CA (US); Shi-He Liu, Sylvania, OH (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 493 days.

(21) Appl. No.: 15/623,285

(22) Filed: Jun. 14, 2017

(65) Prior Publication Data

US 2018/0009864 A1    Jan. 11, 2018

Related U.S. Application Data

(60) Provisional application No. 62/350,584, filed on Jun. 15, 2016.

(51) Int. Cl.
| | |
|---|---|
| *C12N 15/113* | (2010.01) |
| *C07K 14/47* | (2006.01) |
| *C12N 15/86* | (2006.01) |
| *C12N 15/63* | (2006.01) |
| *C12N 15/85* | (2006.01) |
| *C12N 15/11* | (2006.01) |
| *C12N 15/10* | (2006.01) |
| *A61K 48/00* | (2006.01) |

(52) U.S. Cl.
CPC ............ *C12N 15/113* (2013.01); *C07K 14/47* (2013.01); *C07K 14/4747* (2013.01); *C12N 15/11* (2013.01); *C12N 15/63* (2013.01); *C12N 15/85* (2013.01); *C12N 15/86* (2013.01); *A61K 48/0058* (2013.01); *C12N 15/1086* (2013.01); *C12N 2750/14143* (2013.01); *C12N 2830/008* (2013.01); *C12N 2830/85* (2013.01)

(58) Field of Classification Search
CPC ...... C12N 15/113; C12N 15/11; C12N 15/63; C12N 15/85; C12N 15/86; C12N 2830/008; C12N 2830/85; C07K 14/4747; C07K 14/47
USPC .............................. 536/24.1; 435/320.1, 325
See application file for complete search history.

(56) References Cited

U.S. PATENT DOCUMENTS 6,800,737 B2 * 10/2004 Altieri ................ C07K 14/4747
530/386

* cited by examiner

*Primary Examiner* — Anne Marie S Wehbe
(74) *Attorney, Agent, or Firm* — Gates & Cooper LLP

(57) ABSTRACT

The present invention provides nucleic acid constructs, expression vectors, transgenic cell and methods of making and using the same, wherein the nucleic acid construct includes a synthetic promoter designed from the endogenous promoter of BIRC5 and LAMC2. In illustrative working embodiments of the invention, an exogenous nucleic acid fragment encoding thymidine kinase is operably linked to the synthetic promoter which is then shown to regulate the expression of this polypeptide.

13 Claims, 34 Drawing Sheets

Specification includes a Sequence Listing.

BIRC5 5' regulatory sequence (SEQ ID NO: 1)

Homo sapiens chromosome 17, alternate assembly CHM1_1.1, whole genome shotgun sequence (partial)

NCBI Reference Sequence: NC_018928.2

```
   1 aaattgacat cgggccgggc gcagtggctc acatctgtaa tcccagcact ttgggaggcc
  61 gaggcaggca gatcacttga ggtcaggagt ttgagaccag cctggcaaac atggtgaaac
 121 cccatctcta ctaaaaatac aaaaattagc ctggtgtggt ggtgcatgcc tttaatctca
 181 gctactcggg aggctgaggc aggagaatcg cttgaacccg t       ggag gaggttgcag
 241 tgagctgaga tcatgccact gcactccagc ctgggcgata gagcgagact cagtttcaaa
 301 taaataaata aacatcaaaa taaaagtta ctgtattaaa gaatggggc ggggtgggag
 361 gggtggggag aggttgcaaa aataaataaa taaataaata aaccccaaaa tgaaaagac
 421 agtggaggca ccaggcctgc gtggggctgg agggctaata aggccaggcc tcttatctct
 481 ggccatagaa ccagagaagt gagtggatgt gatgcccagc tccagaagtg actccagaac
 541 accctgttcc aaagcagagg acacactgat ttttttttta ataggctgca ggacttactg
 601 ttggtgggac gccctgcttt gcgaagggaa aggaggagtt tgccctgagc acaggccccc
 661 accctccact gggctttccc cagctccctt gtcttcttat cacggtagtg gcccagtccc
 721 tggcccctga ctccagaagg tggccctcct ggaaacccag gtcgtgcagt caacgatgta
 781 ctcgccggga cagcgatgtc tgctgcactc catccctccc ctgttcattt gtccttcatg
 841 cccgtctgga gtagatgctt tttgcagagg tggcaccctg taaagctctc ctgtctgact
 901 tttttttttt ttttagactg agttttgctc ttgttgccta ggctggagtg caatggcaca
 961 atctcagctc actgcaccct ctgcctccg ggttcaagcg attctcctgc ctcagcctcc
1021 cgagtagttg ggattacagg catgcaccac cacgcccagc taattttttgt attttttagta
1081 gagacaaggt ttcaccgtga tggccaggct ggtcttgaac tccaggactc aagtgatgct 1141 cctgcctagg cctctcaaag tgttgggatt acaggcgtga gccactgcac ccggcctgca
1201 cgcgttcttt gaaagcagtc gaggggggcgc taggtgtggg caggggacgag ctggcgcggc
1261 gtcgctgggt gcaccgcgac cacgggcaga gccacgcggc gggaggacta caactcccgg
1321 cacacccggc gccgccccgc ctctactccc agaaggccgc ggggggtgga ccgcctaaga
1381                                          cgcggc  cgccattaa       ag      tc
                                              TIS
                                               +1
1441 accgttggc agaggt   c     cat gggtgcccg acgttgcccc ctgcctggca
     gcccttcctc aaggaccacc gcatctctac attcaagaac tggcccttct tggagggctg
     cgcctgcacc ccggagcggg tgagactgcc cggcctcc
```

Key regulatory elements
P53 binding site
E2F/Rb regulatory element
SP1: Specificity Protein 1
CDE: Cell Cycle-dependent Elements
CHR: Cell Cycle Genes Homology Region TIS: Transcriptional Initial Site

FIG. 1A

ATTTTTAGTAGAGACAAGGTTTCACCGTGATGGCCAGGCTGGTCTTGAACTC

CAGGACTCAAGTGATGCTCCTGCCTAGGCCTCTCAAGTGTTGGGATTACAG

GCGTGAGCCACTGCACCCGGCCTGCACGCGTTCTTTGAAAGCAGTGAGG

GGCGCTAG(G/A)TGTGGGCAGGACGAGCTGGGCGCGTCGCTGGGTGC

ACCGCGACCACGGCCAGAGCCACGGGGAGGACTACAACTCCCGGCAC

ACCCCGGCCGCCCCGCCCTCTACTCCCAGAAGCCGCGGGGTGGACCGCC

TAAGAGAGCGGTGCCCGACATGCCCGCGGCCATTAACCGCCAGA

TTGAATCGC(C/G)GGACCGGTTGGCAGAAGTGGCGGGGCATGGGGTG (SEQ ID NO: 2)

FIG. 1B

BIRC5-S0 (SEQ ID NO: 3)

cctgcctaggcctctcaaagtgttgggattacaggcgtgagccactgcacccggcctgcacgcgttcttt
gaaagcagtcgaggggggcgctaggtgtgggcagggacgagctggcgcggcgtcgctgggtgcaccgcgac
cacgggcagagccacgcggcgggaggactacaactcccggcacaccccgcgccgccccgcctctactccc
agaaggccgcggggggtggaccgcctaagaggcgtgcgctcccgacatgccccgcggcgcgctccc
gacatgccccgcggcgcgccattaaccgccag        tcgcgggaccgtt    c    c
c    c

FIG. 2A

BIRC5-S1 (SEQ ID NO: 4)

cctgcctaggcctctcaaagtgttgggattacaggcgtgagccactgcacccggcctgcacgcgttctttgaaagca
gtcgaggggggcgctaggtgtgggcagggacgagctggcgcggcgtcgctgggtgcaccgcgaccacgggcagagcca
cgcggcgggaggactacaactcccggcacaccccgcgccgccccgcctctactcccagaaggccgcggggggtggac
cgcctaagagggcgtgcgctcccgacatgccccgc
**cctgcctaggcctctcaaagtgttgggattacaggcgtgagccactgcacccggcctgcacgcgttctttgaaagca
gtcgaggggggcgctaggtgtgggcagggacgagctggcgcggcgtcgctgggtgcaccgcgaccacgggcagagcca
cgcggcgggaggactacaactcccggcacaccccgcgccgccccgcctctactcccagaaggccgcggggggtggac
cgcctaagagggcgtgcgctcccgacatgccccgcg**gcgcgccattaaccgccagatttgaatcgcgggacccgttg
gcagaggtggcggcggcggc

FIG. 2B

BIRC5-S2 (BIRC5-SP) (SEQ ID NO: 5)

cctgcctaggcctctcaaagtgttgggattacaggcgtgagccactgcacccggcctgcacgcgttctttgaaagca
gtcgaggggggcgctaggtgtgggcagggacgagctggcgcggcgtcgctgggtgcaccgcgaccacgggcagagcca
cgcggcgggaggactacaactcccggcacaccccgcgccgccccgcctctactcccagaaggccgcggggggtggac
cgcctaagagggcgtgcgctcccgacatgccccgcggcgcgccattaaccgccagatttgaatcgcgggacccgttg
gcagaggtggcggcggcggc**cctgcctaggcctctcaaagtgttgggattacaggcgtgagccactgcacccggcct
gcacgcgttctttgaaagcagtcgaggggggcgctaggtgtgggcagggacgagctggcgcggcgtcgctgggtgcac
cgcgaccacgggcagagccacgcggcgggaggactacaactcccggcacaccccgcgccgccccgcctctactccca
gaaggccgcggggggtggaccgcctaagagggcgtgcgctcccgacatgccccgcggcgcgccattaaccgccagat
ttgaatcgcgggacccgttggcagaggtggcggcggcggc**

FIG. 2C

BIRC5-S3 (SEQ ID NO: 6)

Cctgcctaggcctctcaaagtgttgggattacaggcgtgagccactgcacccggcctgcacgcgttctttgaaagca
gtcgaggggggcgctaggtgtgggcagggacgagctggcgcggcgtcgctgggtgcaccgcgaccacgggcagagcca
cgcggcgggaggactacaactcccggcacaccccgcgccgccccgcctctactcccagaaggccgcggggggtggac
cgcctaagagggcgtgcgctcccgacatgccccgcggcgcgccattaaccgccagatttgaatcgcgggaccgttg
gcagaggtggcggcggcgg**cctgcctaggcctctcaaagtgttgggattacaggcgtgagccactgcacccggcct
gcacgcgttctttgaaagcagtcgaggggggcgctaggtgtgggcagggacgagctggcgcggcgtcgctgggtgcac
cgcgaccacgggcagagccacgcggcgggaggactacaactcccggcacaccccgcgccgccccgcctctactccca
gaaggccgcggggggtggaccgcctaagagggcgtgcgctcccgacatgccccgcggcgcgccattaaccgccagat
ttgaatcgcgggacccgttggcagaggtggcggcggcgg**cctgcctaggcctctcaaagtgttgggattacaggcg
tgagccactgcacccggcctgcacgcgttctttgaaagcagtcgaggggggcgctaggtgtgggcagggacgagctgg
cgcggcgtcgctgggtgcaccgcgaccacgggcagagccacgcggcgggaggactacaactcccggcacaccccgcg
ccgccccgcctctactcccagaaggccgcggggggtggaccgcctaagagggcgtgcgctcccgacatgccccgcgg
cgcgccattaaccgccagatttgaatcgcgggacccgttggcagaggtggcggcggcgg

FIG. 2D

BIRC5-S3E (SEQ ID NO: 7)

Cctgcctaggcctctcaaagtgttgggattacaggcgtgagccactgcacccggcctgcacgcgttctttgaaagca
gtcgagggggcgctaggtgtgggcagggacgagctggcgcggcgtcgctgggtgcaccgcgaccacgggcagagcca
cgcggcgggaggactacaactcccggcacaccccgcgccgccccgcctctactcccagaaggccgcgggggggtggac
cgcctaagagggcgtgcgctcccgacatgccccgcggcgcgccattaaccgccagatttgaatcgcgggacccgttg
gcagaggtggcggcggcgg**cctgcctaggcctctcaaagtgttgggattacaggcgtgagccactgcacccggcct
gcacgcgttctttgaaagcagtcgagggggcgctaggtgtgggcagggacgagctggcgcggcgtcgctgggtgcac
cgcgaccacgggcagagccacgcggcgggaggactacaactcccggcacaccccgcgccgccccgcctctactccca
gaaggccgcggggggtggaccgcctaagagggcgtgcgctcccgacatgccccgcggcgcgccattaaccgccagat
ttgaatcgcgggacccgttggcagaggtggcggcggcgg**cctgcctaggcctctcaaagtgttgggattacaggcg
tgagccactgcacccggcctgcacgcgttctttgaaagcagtcgagggggcgctaggtgtgggcagggacgagctgg
cgcggcgtcgctgggtgcaccgcgaccacgggcagagccacgcggcgggaggactacaactcccggcacaccccgcg
ccgccccgcctctactcccagaaggccgcggggggtggaccgcctaagagggcgtgcgctcccgacatgccccgcgg
cgcgccattaaccgccagatttgaatcgcgggacccgttggcagaggtggcggcggcgg**ggtgccccgacgttgcc
ccctgcctggcagccctttctcaaggaccaccgcatctctacattcaagaactggcccttcttggagggctgcgcct
gcacccggagcgggtgagactgcccggcctcc**

FIG. 2E

BICR5-S4 (SEQ ID NO: 8)

cctgcctaggcctctcaaagtgttgggattacaggcgtgagccactgcacccggcctgcacgcgttctttgaaagca
gtcgagggggcgctaggtgtgggcagggacgagctggcgcggcgtcgctgggtgcaccgcgaccacgggcagagcca
cgcggcgggaggactacaactcccggcacaccccgcgccgccccgcctctactcccagaaggccgcggggggtggac
cgcctaagagggcgtgcgctcccgacatgccccgcggcgcgccattaaccgccagatttgaatcgcgggacccgttg
gcagaggtggcggcggcgg**cctgcctaggcctctcaaagtgttgggattacaggcgtgagccactgcacccggcct
gcacgcgttctttgaaagcagtcgagggggcgctaggtgtgggcagggacgagctggcgcggcgtcgctgggtgcac
cgcgaccacgggcagagccacgcggcgggaggactacaactcccggcacaccccgcgccgccccgcctctactccca
gaaggccgcggggggtggaccgcctaagagggcgtgcgctcccgacatgccccgcggcgcgccattaaccgccagat
ttgaatcgcgggacccgttggcagaggtggcggcggcgg**cctgcctaggcctctca
aagtgttgggattacaggcgtgagccactgcacccggcctgcacgcgttctttgaaagcagtcgagggggcgctagg
tgtgggcagggacgagctggcgcggcgtcgctgggtgcaccgcgaccacgggcagagccacgcggcgggaggactac
aactcccggcacaccccgcgccgccccgcctctactcccagaaggccgcggggggtggaccgcctaagagggcgtgc
gctcccgacatgccccgcggcgcgccattaaccgccagatttgaatcgcgggacccgttggcagaggtggcggcggc
ggc

FIG. 2F

LAMC2 (SEQ ID NO: 9)

```
   1 CAAAGCCTTC TTGACAGCCA CCTCTCTGAA TTATTGTCAC TAGCCTCCTT
  51 AGGAGAAGAG ACAATATAGT TTATACCAAG ATTTGCAGTT GTCTAGATAT
 101 TACTCACTTC AGCTAGCACT GTGCTAGTAG ATAACATTCA AAGTTGGTCT
 151 CAACAAATAT TTTCTCTAGT GCCCATGGAG AGTGGCTGAG AAATACACTC
 201 TAAGATGTAA AAGAGTTTGG TATCTAGATC CTCTTTCTTA TTCATTTCAA
 251 GCCAATATTT ATTAAGCACC AACTGCAAGC TAGATACTAT TATAGTTAGG
 301 AATATAAAGT GGGCCAGGGA TGGTGTTTAT GCCTATAATC CCAGCACTTT
 351 GGGAGGCCAA GGCAGGAGGA TTACTTGAGG CCAGGAATTC AAGGTCAGCC
 401 TGCCCAACAC AGCAAGACCT CGTCTCTACA AAAAATTAAA AAATTAGCTG
 451 GGTGTGGTGG CATTTGCCTG TAGCCCTAGC TACTCAAGAG GCTGAGGTGG
 501 GAGGATTGCT TGAGCCCAGG GGTTGGAGGC TGCAGTGCGC TATGATGGTG
 551 CCATTGAAAA CAAAACAAA AACCAACCAA CAAACAAAAA AACAAACAAA
 601 AAGAAAACGA TACTCAGTCT TTATAGGGAG GTTGGCCAGT CAATAGGTTA
 651 CTTTATGAGT TGCTAACCCT GGTGAGCAGG AAGTTATGTG GACCAGGAGA
 701 GAAACCCTTG GTTCAGCCTG GAGAAGGAG AGGTTGACCC TAAACTGGAG
 751 GGTGGAGAGG ACCCTGTTGT GACTCCGA CTGACTTGTC TTCCTTGATG
 801 TCCTTTAAGC CGGAGCTGAT TCGGGCTGCT GCCTTATTTC TGAGTTAGCG
 851 CTCTTAAGAT TGGGCCTCCC AGTTTGAGGA AGGGCGGGC TGCTGTCTAC
 901 CTCTGTGAAT CTGCCCTGGA CCACCCGGG AGAGAAGGAG GGCTCCGGGG
                                                        -278
 951 AATCTCGCAC ATTCCAGGCA AAGGCTCCCG GGCCGCAGCC TCTGTGCCAC
                                                        -228
1001 ACCCTTGGCC CGGGCCAGGT GTGCGCCCTC CTCGCTGCGA GGGGGAGCGG
                                                        -178
1051 GCGGCTGCGG GGAGCGATTT TCCAGCCCGG TTTGTGCTCT GTGTGTTTGT
             -120                        -98       5'AP1/SP1
1101 CTGCCTCTGG AGGGCTGGGT CCTCCTTATT CACAGGTCAG TCACACCCTG
       -78                              -51  3'AP1          -32
1151 AAACACAGGC TCTCTTCCTG TCAGGACTGA GTCAGGTAGA AGAGTCGATA
                                       +1
1201 AAACCACCTG ATCAAGGAAA AGGAAGGCCC AGCGGAGCGC AGAGTGAGAA
1251 CCACCAACCG
```

FIG. 3

LamS1 (SEQ ID NO: 10)

CGGGCCAGGT ▓TGCGCCCTC CTCGCTGCGA GGGGGAGCGG GCGGCTGCGG
GGAGCGATTT TCCAGCCCGG TTTGTGCTCT GTGTGTTTGT CTGCCTCTGG
AGGGCTGGGT CCTCCTTATT CAC▓▓▓▓▓▓▓▓▓▓CACCCTG AAACACAGGC
TCTCTTCCTG TCAGGAC▓▓▓▓▓▓▓GGTAGA AGAGTC▓TGCGCCCTC CTCGCTGCGA
GGGGGAGCGG GCGGCTGCGG GGAGCGATTT TCCAGCCCGG TTTGTGCTCT
GTGTGTTTGT CTGCCTCTGG AGGGCTGGGT CCTCCTTATT CAC▓▓▓▓▓▓▓
▓▓CACCCTG AAACACAGGC TCTCTTCCTG TCAGGAC▓▓▓▓▓▓▓GGTAGA
AGAGTC▓TGCGCCCTC CTCGCTGCGA GGGGGAGCGG GCGGCTGCGG GGAGCGATTT
TCCAGCCCGG TTTGTGCTCT GTGTGTTTGT CTGCCTCTGG AGGGCTGGGT
CCTCCTTATT CAC▓▓▓▓▓▓▓▓▓▓CACCCTG AAACACAGGC TCTCTTCCTG
TCAGGAC▓▓▓▓▓▓▓GGTAGA AGAGTCAAGCT▓▓▓▓ AAACCACCTG ATCAAGGAAA
AGGAAGGC▓C AGCGGAGCGC AGAGTGAGAA CCACCAACCG ▓▓▓▓▓▓▓

FIG. 4A

LamS1: (SEQ ID NO: 11)

CGTCGGGCCAGGTGTGCGCCCTCCTCGCTGCGAGGGGGAGCGGGCGGCTGCGGGGAGCGATTT
TCCAGCCCGGTTTGTGCTCTGTGTGTTTGTCTGCCTCTGGAGGGCTGGGTCCTCCTTATTCACA
GGTGAGTCACACCCTGAAACACAGGCTCTCTTCCTGTCAGGACTGAGTCAGGTAGAAGAGTCGT
GCGCCCTCCTCGCTGCGAGGGGGAGCGGGCGGCTGCGGGGAGCGATTTTCCAGCCCGGTTTGTG
CTCTGTGTGTTTGTCTGCCTCTGGAGGGCTGGGTCCTCCTTATTCACAGGTGAGTCACACCCTG
AAACACAGGCTCTCTTCCTGTCAGGACTGAGTCAGGTAGAAGAGTCGTGCGCCCTCCTCGCTGC
GAGGGGGAGCGGGCGGCTGCGGGGAGCGATTTTCCAGCCCGGTTTGTGCTCTGTGTGTTTGTCT
GCCTCTGGAGGGCTGGGTCCTCCTTATTCACAGGTGAGTCACACCCTGAAACACAGGCTCTCTT
CCTGTCAGGACTGAGTCAGGTAGAAGAGTCAAGCTTATAAAACCACCTGATCAAGGAAAAGGAA
GGCACAGCGGAGCGCAGAGTGAGAACCACCAACCG

FIG. 4B

LamS2 (SEQ ID NO: 12)

■CGGGCCAGGT■TGCGCCCTC CTCGCTGCGA GGGGGAGCGG GCGGCTGCGG
GGAGCGATTT TCCAGCCCGG TTTGTGCTCT GTGTGTTTGT CTGCCTCTGG
AGGGCTGGGT CCTCCTTATT CACAGGTGAG TCACACCCTG AAACACAGGC
TCTCTTCCTG TCAGGACTGA GTCAGGTAGA AGAGTC caactcccgg cacaccccgc
gccgccccgc ctctactccc agaaggccgc gggggggtgga ccgcctaaga gggcgtgcgc
tcccgacatg ccccgcggcg cgccattaac cgccagattt gaatcgcggg accgttggc
agaggtggcg gcggcggc

FIG. 4C

LamS2: (SEQ ID NO: 13)

CGGTCGGGCCAGGTGTGCGCCCTCCTCGCTGCGAGGGGGAGCGGGCGGCTGCGGGGAGCGATTT
TCCAGCCCGGTTTGTGCTCTGTGTGTTTGTCTGCCTCTGGAGGGCTGGGTCCTCCTTATTCACA
GGTGAGTCACACCCTGAAACACAGGCTCTCTTCCTGTCAGGACTGAGTCAGGTAGAAGAGTCca
actcccggcacaccccgcgccgccccgcctctactcccagaaggccgcgggggtggaccgcct
aagagggcgtgcgctcccgacatgccccgcggcgcgccattaaccgccagatttgaatcgcggg
accgttggcagaggtggcggcggcggc

FIG. 4D

LamS3 (SEQ ID NO: 14)

ACTAGT ACCGGT■caactcccgg cacaccccgc gccgccccgc ctctactccc agaaggccgc gggggtgga
ccgcctaaga gggcgtgcgc tcccgacatg ccccgcggcg cgccattaac cgccagattt
gaatcgcggg accgttggc agaggtggcg gcggcggc CGGGCCAGGT■TGCGCCCTC CTCGCTGCGA
GGGGGAGCGG GCGGCTGCGG GGAGCGATTT TCCAGCCCGG TTTGTGCTCT
GTGTGTTTGT CTGCCTCTGG AGGGCTGGGT CCTCCTTATT CACAGGTGAG
TCACACCCTG AAACACAGGC TCTCTTCCTG TCAGGACTGA GTCAGGTAGA AGAGTC

AAGCTT

FIG. 4E

LamS3: (SEQ ID NO: 15)

CGGTcaactcccggcacaccccgcgccgccccgcctctactcccagaaggccgcgggggggtgga
ccgcctaagagggcgtgcgctcccgacatgccccgcggcgcgccattaaccgccagatttgaat
cgcgggacccgttggcagaggtggcggcggcggcCGGGCCAGGTGTGCGCCCTCCTCGCTGCGA
GGGGGAGCGGGCGGCTGCGGGAGCGATTTTCCAGCCCGGTTTGTGCTCTGTGTGTTTGTCTGC
CTCTGGAGGGCTGGGTCCTCCTTATTCACAGGTGAGTCACACCCTGAAACACAGGCTCTCTTCC
TGTCAGGACTGAGTCAGGTAGAAGAGTCAAGCTT

FIG. 4F

Enhancer at 3' CGP island of Survivin in Lung Cancer Cell Lines

Figure 8: (A) RT-PCR and (B) western blotting revealed that BIRC5 was significantly overexpressed in PDAC specimens and PDAC cell lines. (B) Generation of a powerful synthetic promoter (SP) to BIRC5 (BIRC5-SP) demonstrates significantly luciferase expression compared to CMV and endogenous BIRC5 promoter BIRC5-EP) in ATCC PDAC cells.

Figure 9: High-throughput screening for BIRC5 inhibitory small molecule drugs. Normalized luciferase activity was used to monitor the drug effects on BIRC5-SP-luc2 PDAC cells. The most potent BIRC5 inhibitory drugs including standard chemotherapeutics, as well as other drugs for repurposing, are listed and categorized.

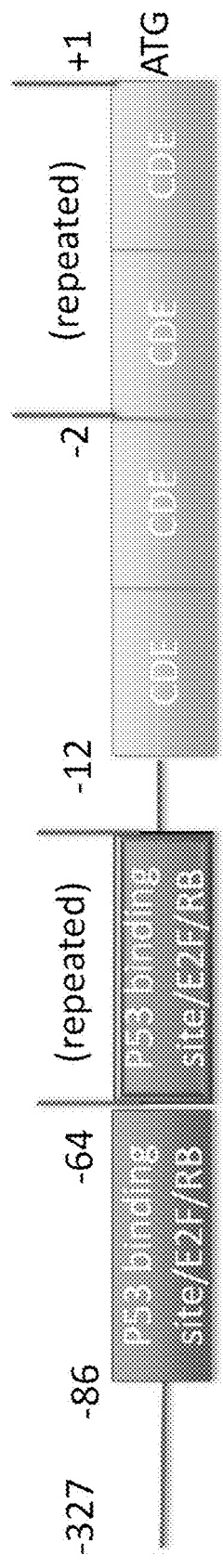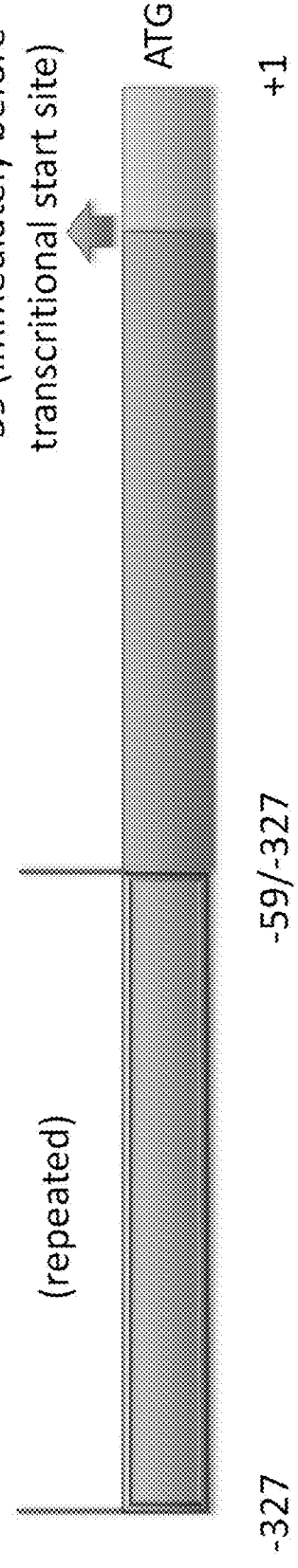
FIG. 11

Synthesis 3: Synthetic Survivin Promoter by multiple repeated core promoter region
SurS2 = BL2  ATG
SurS3 
SurS4 
SurS3E 
FIG. 12

SEQUENCE LISTING

<160> NUMBER OF SEQ ID NOS: 24

<210> SEQ ID NO 1
<211> LENGTH: 1598
<212> TYPE: DNA
<213> ORGANISM: Homo sapiens

<400> SEQUENCE: 1

```
aaattgacat cgggccgggc gcagtggctc acatctgtaa tcccagcact tgggaggcc      60 gaggcaggca gatcacttga ggtcaggagt ttgagaccag cctggcaaac atggtgaaac    120
cccatctcta ctaaaaatac aaaaattagc ctggtgtggt ggtgcatgcc tttaatctca    180
gctactcggg aggctgaggc aggagaatcg cttgaacccg tggcggggag gaggttgcag    240
tgagctgaga tcatgccact gcactccagc ctgggcgata gagcgagact cagtttcaaa    300
taaataaata aacatcaaaa taaaaagtta ctgtattaaa gaatgggggc ggggtgggag    360
gggtggggag aggttgcaaa ataaataaa taaataaata aaccccaaaa tgaaaaagac     420
agtggaggca ccaggcctgc gtggggctgg agggctaata aggccaggcc tcttatctct    480
ggccatagaa ccagagaagt gagtggatgt gatgcccagc tccagaagtg actccagaac    540
accctgttcc aaagcagagg acacactgat tttttttta ataggctgca ggacttactg     600
ttggtgggac gccctgcttt gcgaagggaa aggaggagtt tgccctgagc acaggccccc    660
accctccact gggctttccc cagctccctt gtcttcttat cacggtagtg gcccagtccc    720
tggcccctga ctcagaagg tggccctcct ggaaacccag gtcgtgcagt caacgatgta     780
ctcgccggga cagcgatgtc tgctgcactc catccctccc ctgttcattt gtccttcatg    840
cccgtctgga gtagatgctt tttgcagagg tggcaccctg taaagctctc ctgtctgact    900 ttttttttt ttttagactg agttttgctc ttgttgccta ggctggagtg caatggcaca    960
atctcagctc actgcaccct gcctcccg ggttcaagcg attctcctgc ctcagcctcc     1020
cgagtagttg ggattacagg catgcaccac cacgcccagc taatttttgt atttttagta   1080
gagacaaggt ttcaccgtga tggccaggct ggtcttgaac tccaggactc aagtgatgct   1140
cctgcctagg cctctcaaag tgtgggatt acaggcgtga gccactgcac ccggcctgca    1200
cgcgttcttt gaaagcagtc gagggggcgc taggtgtggg cagggacgag ctggcgcggc   1260
gtcgctgggt gcaccgcgac cacgggcaga gccacgcggc gggaggacta caactcccgg   1320
cacaccccgc gccgccccgc ctctactccc agaaggccgc gggggtggac ccgcctaaga   1380
gggcgtgcgc tcccgacatg ccccgcggcg cgccattaac cgccagattt gaatcgcggg   1440
acccgttggc agaggtggcg gcggcggcat gggtgccccg acgttgcccc ctgcctggca   1500 gcccttctc aaggaccacc gcatctctac attcaagaac tggcccttct tggagggctg    1560
cgcctgcacc ccggagcggg tgagactgcc cggcctcc                           1598
```

<210> SEQ ID NO 2
<211> LENGTH: 405
<212> TYPE: DNA
<213> ORGANISM: Homo sapiens

<400> SEQUENCE: 2

```
atttttagta gagacaaggt ttcaccgtga tggccaggct ggtcttgaac tccaggactc     60
aagtgatgct cctgcctagg cctctcaaag tgtgggatt acaggcgtga gccactgcac    120
ccggcctgca cgcgttcttt gaaagcagtc gagggggcgc tagrtgtggg cagggacgag   180
ctggcgcggc gtcgctgggt gcaccgcgac cacgggcaga gccacgcggc gggaggacta   240
caactcccgg cacaccccgc gccgccccgc ctctactccc agaaggccgc gggggtgga    300 ccgcctaaga gggcgtgcgc tcccgacatg ccccgcggcg cgccattaac cgccagattt   360
gaatcgcsgg acccgttggc agaggtggcg gcggcggcat gggtg                    405
```

<210> SEQ ID NO 3
<211> LENGTH: 357

<212> TYPE: DNA
<213> ORGANISM: Homo sapiens

<400> SEQUENCE: 3

```
cctgcctagg cctctcaaag tgttgggatt acaggcgtga gccactgcac ccggcctgca    60
cgcgttcttt gaaagcagtc gagggggcgc taggtgtggg cagggacgag ctggcgcggc   120
gtcgctgggt gcaccgcgac cacgggcaga gccacgcggc gggaggacta caactcccgg   180
cacacccccgc gccgccccgc ctctactccc agaaggccgc gggggggtgga ccgcctaaga  240
gggcgtgcgc tcccgacatg ccccgcgggc gtgcgctccc gacatgcccc gcggcgcgcc   300
attaaccgcc agatttgaat cgcgggaccc gttggcggcg cggcggcgg cggcggc      357
```

<210> SEQ ID NO 4
<211> LENGTH: 594
<212> TYPE: DNA
<213> ORGANISM: Homo sapiens

<400> SEQUENCE: 4

```
cctgcctagg cctctcaaag tgttgggatt acaggcgtga gccactgcac ccggcctgca    60
cgcgttcttt gaaagcagtc gagggggcgc taggtgtggg cagggacgag ctggcgcggc   120
gtcgctgggt gcaccgcgac cacgggcaga gccacgcggc gggaggacta caactcccgg   180
cacacccccgc gccgccccgc ctctactccc agaaggccgc gggggggtgga ccgcctaaga  240
gggcgtgcgc tcccgacatg ccccgccctg cctaggcctc tcaaagtgtt gggattacag   300
gcgtgagcca ctgcacccgg cctgcacgcg ttctttgaaa gcagtcgagg gggcgctagg   360
tgtgggcagg gacgagctgg cgcggcgtcg ctgggtgcac cgcgaccacg ggcagagcca   420
cgcggcggga ggactacaac tcccggcaca ccccgcgccg ccccgcctct actcccagaa   480
ggccgcgggg ggtggaccgc ctaagagggc gtgcgctccc gacatgcccc gcggcgcgcc   540
attaaccgcc agatttgaat cgcgggaccc gttggcagag gtggcggcgg cggc         594
```

<210> SEQ ID NO 5
<211> LENGTH: 656
<212> TYPE: DNA
<213> ORGANISM: Homo sapiens

<400> SEQUENCE: 5

```
cctgcctagg cctctcaaag tgttgggatt acaggcgtga gccactgcac ccggcctgca    60
cgcgttcttt gaaagcagtc gagggggcgc taggtgtggg cagggacgag ctggcgcggc   120
gtcgctgggt gcaccgcgac cacgggcaga gccacgcggc gggaggacta caactcccgg   180
cacacccccgc gccgccccgc ctctactccc agaaggccgc gggggggtgga ccgcctaaga  240
gggcgtgcgc tcccgacatg ccccgcgggcg cgccattaac cgccagattt gaatcgcggg   300
acccgttggc agaggtggcg gcggcggccc tgcctaggcc tctcaaagtg ttgggattac   360
aggcgtgagc cactgcaccc ggcctgcacg cgttctttga aagcagtcga gggggcgcta   420
ggtgtgggca gggacgagct ggcgcggcgt cgctgggtgc accgcgacca cgggcagagc   480
cacgcggcgg gaggactaca actcccggca caccccgcgc cgccccgcct ctactcccag   540
aaggccgcgg ggggtggacc gcctaagagg gcgtgcgctc ccgacatgcc ccgcggcgcg   600
ccattaaccg ccagatttga atcgcgggac ccgttggcag aggtggcggc ggcggc        656
```

<210> SEQ ID NO 6
<211> LENGTH: 984
<212> TYPE: DNA

<213> ORGANISM: Homo sapiens

<400> SEQUENCE: 6

| | |
|---|---|
| cctgcctagg cctctcaaag tgttgggatt acaggcgtga gccactgcac ccggcctgca | 60 |
| cgcgttcttt gaaagcagtc gagggggcgc taggtgtggg cagggacgag ctggcgcggc | 120 |
| gtcgctgggt gcaccgcgac cacgggcaga gccacgcggc gggaggacta caactcccgg | 180 |
| cacaccccgc gccgccccgc ctctactccc agaaggccgc gggggtggga ccgcctaaga | 240 |
| gggcgtgcgc tcccgacatg ccccgcggcg cgccattaac cgccagattt gaatcgcggg | 300 |
| acccgttggc agaggtggcg gcggcggccc tgcctaggcc tctcaaagtg ttgggattac | 360 |
| aggcgtgagc cactgcaccc ggcctgcacg cgttctttga aagcagtcga gggggcgcta | 420 |
| ggtgtgggca gggacgagct ggcgcggcgt cgctgggtgc accgcgacca cgggcagagc | 480 |
| cacgcggcgg gaggactaca actcccggca caccccgcgc cgccccgcct ctactcccag | 540 |
| aaggccgcgg ggggtggacc gcctaagagg gcgtgcgctc ccgacatgcc ccgcggcgcg | 600 |
| ccattaaccg ccagatttga atcgcgggac ccgttggcag aggtggcggc ggcggccctg | 660 |
| cctaggcctc tcaaagtgtt gggattacag gcgtgagcca ctgcacccgg cctgcacgcg | 720 |
| ttctttgaaa gcagtcgagg gggcgctagg tgtgggcagg gacgagctgg cgcggcgtcg | 780 |
| ctgggtgcac cgcgaccacg ggcagagcca cgcggcggga ggactacaac tcccggcaca | 840 |
| ccccgcgccg ccccgcctct actcccagaa ggccgcgggg gtggaccgc ctaagagggc | 900 |
| gtgcgctccc gacatgcccc gcggcgcgcc attaaccgcc agatttgaat cgcgggaccc | 960 |
| gttggcagag gtggcggcgg cggc | 984 |

<210> SEQ ID NO 7
<211> LENGTH: 1111
<212> TYPE: DNA
<213> ORGANISM: Homo sapiens

<400> SEQUENCE: 7

| | |
|---|---|
| cctgcctagg cctctcaaag tgttgggatt acaggcgtga gccactgcac ccggcctgca | 60 |
| cgcgttcttt gaaagcagtc gagggggcgc taggtgtggg cagggacgag ctggcgcggc | 120 |
| gtcgctgggt gcaccgcgac cacgggcaga gccacgcggc gggaggacta caactcccgg | 180 |
| cacaccccgc gccgccccgc ctctactccc agaaggccgc gggggtggga ccgcctaaga | 240 |
| gggcgtgcgc tcccgacatg ccccgcggcg cgccattaac cgccagattt gaatcgcggg | 300 |
| acccgttggc agaggtggcg gcggcggccc tgcctaggcc tctcaaagtg ttgggattac | 360 |
| aggcgtgagc cactgcaccc ggcctgcacg cgttctttga aagcagtcga gggggcgcta | 420 |
| ggtgtgggca gggacgagct ggcgcggcgt cgctgggtgc accgcgacca cgggcagagc | 480 |
| cacgcggcgg gaggactaca actcccggca caccccgcgc cgccccgcct ctactcccag | 540 |
| aaggccgcgg ggggtggacc gcctaagagg gcgtgcgctc ccgacatgcc ccgcggcgcg | 600 |
| ccattaaccg ccagatttga atcgcgggac ccgttggcag aggtggcggc ggcggccctg | 660 |
| cctaggcctc tcaaagtgtt gggattacag gcgtgagcca ctgcacccgg cctgcacgcg | 720 |
| ttctttgaaa gcagtcgagg gggcgctagg tgtgggcagg gacgagctgg cgcggcgtcg | 780 |
| ctgggtgcac cgcgaccacg ggcagagcca cgcggcggga ggactacaac tcccggcaca | 840 |
| ccccgcgccg ccccgcctct actcccagaa ggccgcgggg gtggaccgc ctaagagggc | 900 |
| gtgcgctccc gacatgcccc gcggcgcgcc attaaccgcc agatttgaat cgcgggaccc | 960 |
| gttggcagag gtggcggcgg cggcggtgcc ccgacgttgc cccctgcctg gcagcccttt | 1020 |

```
ctcaaggacc accgcatctc tacattcaag aactggccct tcttggaggg ctgcgcctgc    1080 acccccggagc gggtgagact gcccggcctc c                                  1111

<210> SEQ ID NO 8
<211> LENGTH: 1312
<212> TYPE: DNA
<213> ORGANISM: Homo sapiens

<400> SEQUENCE: 8
cctgcctagg cctctcaaag tgttgggatt acaggcgtga gccactgcac ccggcctgca      60
cgcgttcttt gaaagcagtc gagggggcgc taggtgtggg cagggacgag ctggcgcggc     120
gtcgctgggt gcaccgcgac cacgggcaga gccacgcggc gggaggacta caactcccgg     180
cacaccccgc gccgccccgc tctactccca gaaggccgc ggggggtgga ccgcctaaga      240
gggcgtgcgc tcccgacatg ccccgcggcg cgccattaac cgccagattt gaatcgcggg     300
acccgttggc agaggtggcg gcggcggccc tgcctaggcc tctcaaagtg ttgggattac     360
aggcgtgagc cactgcaccc ggcctgcacg cgttctttga aagcagtcga gggggcgcta     420
ggtgtgggca gggacgagct ggcgcggcgt cgctgggtgc accgcgacca cgggcagagc     480
cacgcggcgg gaggactaca actcccggca caccccgcgc cgccccgcct ctactcccag     540
aaggccgcgg gggtggacc gcctaagagg gcgtgcgctc ccgacatgcc ccgcggcgcg     600
ccattaaccg ccagatttga atcgcgggac ccgttggcag aggtggcggc ggcggccctg     660
cctaggcctc tcaaagtgtt gggattacag gcgtgagcca ctgcacccgg cctgcacgcg     720
ttctttgaaa gcagtcgagg gggcgctagg tgtgggcagg gacgagctgg cgcggcgtcg     780
ctgggtgcac cgcgaccacg ggcagagcca cgcggcggga ggactacaac tcccggcaca     840
ccccgcgccg ccccgcctct actcccagaa ggccgcgggg ggtggaccgc taagagggc     900 gtgcgctccc gacatgcccc gcggcgcgcc attaaccgcc agatttgaat cgcgggaccc     960
gttggcagag gtggcggcgg cggccctgcc taggcctctc aaagtgttgg gattacaggc    1020
gtgagccact gcacccggcc tgcacgcgtt ctttgaaagc agtcgagggg gcgctaggtg    1080
tgggcaggga cgagctggcg cggcgtcgct gggtgcaccg cgaccacggg cagagccacg    1140 cggcggagg actacaactc ccggcacacc ccgcgccgcc ccgcctctac tcccagaagg     1200
ccgcgggggg tggaccgcct aagagggcgt gcgctcccga catgccccgc ggcgcgccat    1260
taaccgccag atttgaatcg cgggacccgt tggcagaggt ggcggcggcg gc            1312

<210> SEQ ID NO 9
<211> LENGTH: 1260
<212> TYPE: DNA
<213> ORGANISM: Homo sapiens

<400> SEQUENCE: 9
caaagccttc ttgacagcca cctctctgaa ttattgtcac tagcctcctt aggagaagag      60
acaatatagt ttataccaag atttgcagtt gtctagatat tactcacttc agctagcact     120
gtgctagtag ataacattca agttggtct caacaaatat tttctctagt gcccatggag      180
agtggctgag aaatacactc taagatgtaa aagagtttgg tatctagatc ctctttctta     240
ttcatttcaa gccaatattt attaagcacc aactgcaagc tagatactat tatagttagg     300
aatataaagt gggccaggga tggtgtttat gcctataatc ccagcacttt gggaggccaa     360
ggcaggagga ttacttgagg ccaggaattc aaggtcagcc tgcccaacac agcaagacct     420
```

| | |
|---|---|
| cgtctctaca aaaaattaaa aaattagctg ggtgtggtgg catttgcctg tagccctagc | 480 |
| tactcaagag gctgaggtgg gaggattgct tgagcccagg ggttggaggc tgcagtgcgc | 540 |
| tatgatggtg ccattgaaaa caaaaacaaa aaccaaccaa caaacaaaaa aacaaacaaa | 600 |
| aagaaaacga tactcagtct ttatagggag gttggccagt caataggtta ctttatgagt | 660 |
| tgctaaccct ggtgagcagg aagttatgtg gaccaggaga gaaaccettg gttcagcctg | 720 |
| gagaaaggag aggttgaccc taaactggag ggtggagagg accctgttgt gactctccga | 780 |
| ctgacttgtc ttccttgatg tcctttaagc cggagctgat tcgggctgct gccttatttc | 840 |
| tgagttagcg ctcttaagat tgggcctccc agtttgagga aggggcgggc tgctgtctac | 900 |
| ctctgtgaat ctgccctgga ccaccccggg agagaaggag ggctccgggg aatctcgcac | 960 |
| attccaggca aaggctcccg ggccgcagcc tctgtgccac acccttggcc cgggccaggt | 1020 |
| gtgcgccctc ctcgctgcga gggggagcgg gcggctgcgg ggagcgattt tccagcccgg | 1080 |
| tttgtgctct gtgtgtttgt ctgcctctgg agggctgggt cctccttatt cacaggtgag | 1140 |
| tcacaccctg aaacacaggc tctcttcctg tcaggactga gtcaggtaga agagtcgata | 1200 |
| aaaccacctg atcaaggaaa aggaaggcac agcggagcgc agagtgagaa ccaccaaccg | 1260 |

<210> SEQ ID NO 10
<211> LENGTH: 613
<212> TYPE: DNA
<213> ORGANISM: Homo sapiens

<400> SEQUENCE: 10

| | |
|---|---|
| cgggccaggt gtgcgccctc ctcgctgcga gggggagcgg gcggctgcgg ggagcgattt | 60 |
| tccagcccgg tttgtgctct gtgtgtttgt ctgcctctgg agggctgggt cctccttatt | 120 |
| cacaggtgag tcacaccctg aaacacaggc tctcttcctg tcaggactga gtcaggtaga | 180 |
| agagtcgtgc gccctcctcg ctgcgagggg gagcgggcgg ctgcggggag cgattttcca | 240 |
| gcccggtttg tgctctgtgt gtttgtctgc ctctggaggg ctgggtcctc cttattcaca | 300 |
| ggtgagtcac accctgaaac acaggctctc ttcctgtcag gactgagtca ggtagaagag | 360 |
| tcgtgcgccc tcctcgctgc gagggggagc gggcggctgc ggggagcgat tttccagccc | 420 |
| ggtttgtgct ctgtgtgttt gtctgcctct ggagggctgg gtcctcctta ttcacaggtg | 480 |
| agtcacaccc tgaaacacag gctctcttcc tgtcaggact gagtcaggta gaagagtcaa | 540 |
| gcttataaaa ccacctgatc aaggaaaagg aaggcacagc ggagcgcaga gtgagaacca | 600 |
| ccaaccggaa ttc | 613 |

<210> SEQ ID NO 11
<211> LENGTH: 611
<212> TYPE: DNA
<213> ORGANISM: Homo sapiens

<400> SEQUENCE: 11

| | |
|---|---|
| cggtcgggcc aggtgtgcgc cctcctcgct gcgagggga gcgggcggct gcggggagcg | 60 |
| attttccagc ccggtttgtg ctctgtgtgt ttgtctgcct ctggagggct gggtcctcct | 120 |
| tattcacagg tgagtcacac cctgaaacac aggctctctt cctgtcagga ctgagtcagg | 180 |
| tagaagagtc gtgcgccctc ctcgctgcga gggggagcgg gcggctgcgg ggagcgattt | 240 |
| tccagcccgg tttgtgctct gtgtgtttgt ctgcctctgg agggctgggt cctccttatt | 300 |
| cacaggtgag tcacaccctg aaacacaggc tctcttcctg tcaggactga gtcaggtaga | 360 |
| agagtcgtgc gccctcctcg ctgcgagggg gagcgggcgg ctgcggggag cgattttcca | 420 |

```
gcccggtttg tgctctgtgt gtttgtctgc ctctggaggg ctgggtcctc cttattcaca    480
ggtgagtcac accctgaaac acaggctctc ttcctgtcag gactgagtca ggtagaagag    540
tcaagcttat aaaaccacct gatcaaggaa aaggaaggca cagcggagcg cagagtgaga    600
accaccaacc g                                                         611
```

<210> SEQ ID NO 12
<211> LENGTH: 344
<212> TYPE: DNA
<213> ORGANISM: Homo sapiens

<400> SEQUENCE: 12

```
cgggccaggt gtgcgccctc ctcgctgcga gggggagcgg gcggctgcgg ggagcgattt     60
tccagcccgg tttgtgctct gtgtgtttgt ctgcctctgg agggctgggt cctccttatt    120
cacaggtgag tcacaccctg aaacacaggc tctcttcctg tcaggactga gtcaggtaga    180
agagtccaac tcccggcaca ccccgcgccg cccgcctct actcccagaa ggccgcgggg    240
ggtggaccgc ctaagagggc gtgcgctccc gacatgcccc gcggcgcgcc attaaccgcc    300
agatttgaat cgcgggaccc gttggcagag gtggcggcgg cggc                    344
```

<210> SEQ ID NO 13
<211> LENGTH: 348
<212> TYPE: DNA
<213> ORGANISM: Homo sapiens

<400> SEQUENCE: 13

```
cggtcgggcc aggtgtgcgc cctcctcgct gcgaggggga gcggcggct gcggggagcg     60 attttccagc ccggtttgtg ctctgtgtgt tgtctgcct ctggagggct gggtcctcct    120
tattcacagg tgagtcacac cctgaaacac aggctctctt cctgtcagga ctgagtcagg    180
tagaagagtc caactcccgg cacaccccgc cgccccgc ctctactccc agaaggccgc    240 gggggggtgga ccgcctaaga gggcgtgcgc tcccgacatg ccccgcggcg cgccattaac    300
cgccagattt gaatcgcggg acccgttggc agaggtggcg gcggcggc                348
```

<210> SEQ ID NO 14
<211> LENGTH: 362
<212> TYPE: DNA
<213> ORGANISM: Homo sapiens

<400> SEQUENCE: 14

```
actagtaccg gtcaactccc ggcacacccc gcgccgcccc gcctctactc ccagaaggcc     60
gcggggggtg gaccgcctaa gagggcgtgc gctcccgaca tgccccgcgg cgcgccatta    120
accgccagat ttgaatcgcg ggaccgttg gcagaggtgg cggcggcggc cgggccaggt    180
gtgcgccctc ctcgctgcga gggggagcgg gcggctgcgg ggagcgattt tccagcccgg    240
tttgtgctct gtgtgtttgt ctgcctctgg agggctgggt cctccttatt cacaggtgag    300
tcacaccctg aaacacaggc tctcttcctg tcaggactga gtcaggtaga agagtcaagc    360
tt                                                                   362
```

<210> SEQ ID NO 15
<211> LENGTH: 354
<212> TYPE: DNA
<213> ORGANISM: Homo sapiens

<400> SEQUENCE: 15

```
cggtcaactc ccggcacacc ccgcgccgcc ccgcctctac tcccagaagg ccgcgggggg      60
tggaccgcct aagagggcgt gcgctcccga catgccccgc ggcgcgccat taaccgccag     120
atttgaatcg cgggacccgt tggcagaggt ggcggcggcg gccgggccag gtgtgcgccc     180
tcctcgctgc gaggggagc  gggcggctgc ggggagcgat tttccagccc ggtttgtgct     240
ctgtgtgttt gtctgcctct ggagggctgg gtcctcctta ttcacaggtg agtcacaccc     300
tgaaacacag gctctcttcc tgtcaggact gagtcaggta aagagtcaa  gctt            354
```

<210> SEQ ID NO 16
<211> LENGTH: 9
<212> TYPE: DNA
<213> ORGANISM: Homo sapiens

<400> SEQUENCE: 16

```
gagggggcg                                                              9
```

<210> SEQ ID NO 17
<211> LENGTH: 23
<212> TYPE: DNA
<213> ORGANISM: Homo sapiens

<400> SEQUENCE: 17

```
gggcgtgcgc tcccgacatg ccc                                             23
```

<210> SEQ ID NO 18
<211> LENGTH: 328
<212> TYPE: DNA
<213> ORGANISM: Homo sapiens

<400> SEQUENCE: 18

```
cctgcctagg cctctcaaag tgttgggatt acaggcgtga gccactgcac ccggcctgca      60
cgcgttcttt gaaagcagtc gagggggcgc taggtgtggg cagggacgag ctggcgcggc     120
gtcgctgggt gcaccgcgac cacgggcaga gccacgcggc gggaggacta caactcccgg     180
cacaccccgc gccgccccgc ctctactccc agaaggccgc gggggtgga  ccgcctaaga     240 gggcgtgcgc tcccgacatg ccccgcggcg cgccattaac cgccagattt gaatcgcggg     300
acccgttggc agaggtggcg gcggcggc                                        328
```

<210> SEQ ID NO 19
<211> LENGTH: 162
<212> TYPE: DNA
<213> ORGANISM: Homo sapiens

<400> SEQUENCE: 19

```
cggtcaactc ccggcacacc ccgcgccgcc ccgcctctac tcccagaagg ccgcgggggg      60
tggaccgcct aagagggcgt gcgctcccga catgccccgc ggcgcgccat taaccgccag     120
atttgaatcg cgggacccgt tggcagaggt ggcggcggcg gc                        162
```

<210> SEQ ID NO 20
<211> LENGTH: 130
<212> TYPE: DNA
<213> ORGANISM: Homo sapiens

<400> SEQUENCE: 20

```
atgggtgccc cgacgttgcc ccctgcctgg cagccctttc tcaaggacca ccgcatctct      60
acattcaaga actggcccct tcttggaggg ctgcgcctgca ccccggagcg ggtgagactg     120
cccggcctcc                                                            130
```

```
<210> SEQ ID NO 21
<211> LENGTH: 186
<212> TYPE: DNA
<213> ORGANISM: Homo sapiens

<400> SEQUENCE: 21
cgggccaggt gtgcgccctc ctcgctgcga gggggagcgg gcggctgcgg ggagcgattt      60
tccagcccgg tttgtgctct gtgtgtttgt ctgcctctgg agggctgggt cctccttatt     120
cacaggtgag tcacaccctg aaacacaggc tctcttcctg tcaggactga gtcaggtaga     180
agagtc                                                                186

<210> SEQ ID NO 22
<211> LENGTH: 33
<212> TYPE: DNA
<213> ORGANISM: Homo sapiens

<400> SEQUENCE: 22
gataaaacca cctgatcaag gaaaaggaag gca                                   33

<210> SEQ ID NO 23
<211> LENGTH: 34
<212> TYPE: DNA
<213> ORGANISM: Homo sapiens

<400> SEQUENCE: 23
ggacccgttg gcagaggtgg cggcggcggc atgg                                  34

<210> SEQ ID NO 24
<211> LENGTH: 405
<212> TYPE: DNA
<213> ORGANISM: Homo sapiens

<400> SEQUENCE: 24 attttagta gagacaaggt ttcaccgtga tggccaggct ggtcttgaac tccaggactc       60
aagtgatgct cctgcctagg cctctcaaag tgttgggatt acaggcgtga gccactgcac     120
ccggcctgca cgcgttcttt gaaagcagtc gaggggggcgc taggtgtggg cagggacgag    180
ctggcgcggc gtcgctgggt gcaccgcgac cacgggcaga gccacgcggc gggaggacta    240
caactcccgg cacaccccgc gccgccccgc ctctactccc agaaggccgc ggggggtgga    300
ccgcctaaga gggcgtgcgc tcccgacatg ccccgcggcg cgccattaac cgccagattt    360
gaatcgcggg acccgttggc agaggtggcg gcggcggcat gggtg                    405
```

SYNTHETIC PROMOTERS FOR HIGH THROUGHPUT SCREENING AND GENE MODULATION

CROSS-REFERENCE TO RELATED APPLICATIONS

This application claims priority under Section 119(e) from U.S. Provisional Application Ser. No. 62/350,584, filed Jun. 15, 2016, entitled "SYNTHETIC PROMOTERS FOR HIGH THROUGHPUT SCREENING AND GENE MODULATION" by Francis C. Brunicardi et al., the contents of which are incorporated herein by reference.

SEQUENCE LISTING

The instant application contains a Sequence Listing which has been submitted electronically in ASCII format and is hereby incorporated by reference in its entirety. Said ASCII copy, created on May 11, 2017, is named 30435_288-US-U1_SL.txt and is 18,574 bytes in size.

TECHNICAL FIELD

The present invention relates generally to compositions and methods for modulating gene expression and/or the activity of novel, synthetic gene promoters.

BACKGROUND OF THE INVENTION

Expression vectors have been used for decades to express genes encoding polypeptides of interest in host cells. With such vectors, viral or cellular promoters are typically used to express a gene of interest in selected host cells. For example, by using tissue specific promoters, one can selectively turn on genes in specific cell lineages, an important goal in gene therapy. A number of illustrative promoter systems known in the art are described below.

U.S. Pat. No. 7,592,320 discloses a cancer gene therapy based on translational control of a suicide gene that does not require specific knowledge of the cancer cells, but instead targets a general characteristic that distinguishes cancer cells from normal cells, i.e., elevated eIF4E expression. The expression of a toxin or conditional toxin such as HTK is translationally repressed in normal cells by placing a complex 5' UTR in front of its reading frame. In prototype experiments, this HTK mRNA, a transcriptional product of the BK-viralTK vector, was translationally regulated so as to largely inhibit its production in normal murine and human cells, while cancer cells efficiently translated the protein, resulting in increased sensitivity to ganciclovir (GCV). Synthesis of the HTK protein from the BK-viralTK vector (containing the 5' UTR of Fibroblast growth factor-2 ("FGF-2") readily occurred in a panel of murine and human breast carcinoma lines, but not in normal cell lines. Subcutaneous tumors and experimental lung metastases of the breast carcinoma line MM2MT in BALB/c mice were greatly reduced by transfection with the BK-viralTK vector, followed by GCV administration. Both the BK-viralTK and the BK-TK (control) vectors were effective in reducing lung metastasis following systemic delivery of the vectors and subsequent GCV administration. However, the BK-TK vector was highly toxic to mice while little to no toxicity was seen in mice treated with the BK-viralTK vector.

U.S. Pat. No. 7,453,022 discloses a method of increasing the content of selected transgene-coded proteins or peptides in plants and includes a method of increasing the content of one or more transgene-coded proteins or peptides in a plant. The increase is an effect of a decrease in the concentration of an ATP/ADP transporter in the plant. The method depends on transformation with and expression of a cDNA encoding an ATP/ADP transporter operably linked in antisense orientation to a promoter active in the plant.

U.S. Pat. No. 7,125,902 discloses methods, compounds, and diagnostics for cancer treatment and includes methods of treating cancer employing isoxazole derivatives. Compounds and methods of using these compounds for isolating and/or detecting binding proteins, which may be indicative of a disease, are also described.

U.S. Pat. No. 6,977,244 discloses the inhibition of Bcl-2 protein expression by liposomal antisense oligodeoxynucleotides and provides compositions and methods for use in the treatment of Bcl-2-associated diseases like cancer, specifically, in the treatment of follicular lymphoma (FL). The compositions contain antisense oligonucleotides that hybridize to Bcl-2 nucleic acids, the gene products of which are known to interact with the tumorigenic protein Bcl-2. Used alone, or in conjunction with other antisense oligonucleotides, these compositions inhibit the proliferation of FL cancer cells.

While a large variety of promoter systems are known in the art such as those noted above, there is a need for additional promoter systems that are optimized for specific applications, for example to identify agents that can modulate the expression of genes whose expression is controlled by a specific constellation of promoter elements, especially for genes whose products are involved in pathological conditions such as cancer. The invention disclosed herein provides a number of examples of such optimized promoter systems.

SUMMARY OF THE INVENTION

The invention disclosed herein provides synthetic promoters having a number of highly desirable characteristics, as well as methods for making and using these promoters. Embodiments of the invention include, for example, nucleic acid constructs comprising a synthetic promoter operably linked a heterologous nucleic acid (e.g. a nucleic acid encoding a therapeutic gene such as a growth factor or a reporter gene such as luciferase). Embodiments of the invention include using expression vectors having the synthetic promoters disclosed herein to observe the effects of agents on gene expression, and/or to modulate the expression of genes in human cells such as human cancer cells. As disclosed below, embodiments of the invention provide powerful tools for use in a variety of diagnostic and therapeutic contexts.

The synthetic promoter systems that are disclosed herein have a number of exciting applications, including their use in "Actionable Genomics Platforms", that is protocols designed to identify agents that can modulate the expression of genes involved in pathological conditions such as cancer. As described in detail below, these platforms allow artisans to screen libraries of agents (e.g. libraries of FDA-approved agents) to identify compounds that can modulate the expression genes having a role in various disease states. The powerful synthetic promoters designed for each actionable gene as described herein can be used in high throughput screening protocols for FDA approved drugs and novel drugs for liver and pancreas cancer therapy; precision gene therapy for screening, imaging and therapy of liver and pancreas cancer; and basic science research to understand the molecular biology and signaling pathways of liver and pancreas cancer. Such embodiments of the invention have an enormous commercial and scientific potential for precision cancer care.

Embodiments of the invention include methods for regulating expression of an exogenous protein in one or more cells by providing an expression vector comprising a synthetic promoter and an exogenous nucleic acid operably linked to the synthetic promoter, wherein the synthetic promoter regulates the expression of an exogenous nucleic acid; transforming one or more cells with the expression vector; and expressing the exogenous nucleic acid. The present invention also provides a method for selectively expressing a toxin within a cell by administering an expression vector comprising a synthetic promoter and an exogenous nucleic acid fragment operably linked to the synthetic promoter, wherein the synthetic promoter regulates the expression of an exogenous nucleic acid fragment; transforming one or more cells with the expression vector; and expressing the exogenous nucleic acid fragment. In one aspect, the heterologous protein is transiently over-expressed. In another aspect, the synthetic promoter is a BL-2 synthetic promoter, a BL-3 synthetic promoter or both.

Other embodiments of the invention include nucleic acid constructs having selected transcriptional motifs such as a BL-2 promoter comprising at least one of a EGR1 binding site motif GAGGGGGCG (SEQ ID NO: 16) and a P53 binding site motif GGGCGTGCGCTCCCGACATGCCC (SEQ ID NO: 17). In certain instances, the transcriptional motifs are separated by 0 to 41. In other instances, the transcriptional motifs are separated by 0 to 151 nucleotides. In one aspect, the BL-2 promoter comprises at least two, at least three, or at least four repeats of a nucleotide sequence spanning positions −327 to −1 of the human BIRC5/survivin promoter gene (SEQ ID NO: 18). The coordinates are relative to the first transcription initiation point (+1). In one embodiment, the BL-2 promoter comprises 2 repeats of a nucleotide sequence spanning positions −327 to −1 of the human BIRC5/survivin promoter gene (SEQ ID NO: 5). In certain instances, the BL-2 promoter further includes an ATG motif. In other instances, the BL-2 promoter further includes a nucleotide sequence spanning positions +1 to +128 of the human BIRC5/survivin promoter gene (SEQ ID NO: 20).

In another aspect, the BL-3 promoter comprises a nucleotide sequence spanning positions −218 to −32 of the human LAMC2 promoter gene (SEQ ID NO: 21). In one preferred embodiment, the BL-3 promoter comprises at least three repeats of a nucleotide sequence spanning positions −218 to −32 of the human LAMC2 promoter gene (SEQ ID NO: 12). In certain instances, the BL-3 promoter further includes a nucleotide sequence spanning positions −32 to +1 of the human LAMC2 promoter gene (SEQ ID NO: 22). In one or more embodiments, the BL-3 promoter comprises a nucleotide sequence spanning positions −218 to −32 of the human LAMC2 promoter gene (SEQ ID NO: 21) and a nucleotide sequence spanning positions −99 to +59 of the BIRC5/survivin promoter gene (SEQ ID NO: 19). In one instance, the BL-3 promoter further includes a nucleotide sequence spanning positions −32 to +1 of the human LAMC2 promoter gene (SEQ ID NO: 22) or an E4 TATA motif.

Yet another embodiment of the invention includes a method for regulating expression of an exogenous protein in one or more cells comprising the steps of: providing an expression vector comprising a synthetic promoter and an exogenous nucleic acid fragment operably linked to the synthetic promoter, wherein the synthetic promoter regulates the expression of an exogenous nucleic acid fragment; transforming one or more cells with the expression vector; and expressing the exogenous nucleic acid fragment. In one aspect, the heterologous protein is transiently over-expressed. In another aspect, the synthetic promoter is a BL-2 promoter, a BL-3 promoter or both.

Yet another embodiment of the present invention includes a method for selectively expressing a toxin within a cell comprising the steps of combining the cell with an expression vector comprising a synthetic promoter and an exogenous nucleic acid fragment operably linked to the synthetic promoter. In such embodiments of the invention, the cell is selected to be one where the synthetic promoter regulates the expression of an exogenous nucleic acid fragment to which it is operably linked. Such methods can include transforming one or more cells with the expression vector; and expressing the exogenous nucleic acid fragment with the synthetic promoter. In one aspect, the step of administering an expression vector is defined further as providing a cell with an amount of the exogenous nucleic acid fragment effective to inhibit cellular metabolism or growth.

The present invention also provides a method of treatment for a cancer by providing a patient in need of cancer treatment; administering a therapeutically effective amount of an expression vector to the patient, wherein the expression vector comprises a synthetic promoter and an exogenous nucleic acid fragment operably linked to the synthetic promoter, wherein the synthetic promoter regulates the expression of an exogenous nucleic acid fragment; transforming one or more cells of the patient with the expression vector; and expressing the exogenous nucleic acid fragment in the one or more cells of the patient, wherein the exogenous nucleic acid fragment is transcribed under conditions that exist within tumor cells to produce a messenger RNA sequence that comprises a translatable sequence encoding a protein.

Yet another embodiment of the present invention includes a method of treatment for a cancer comprising the steps of: providing a patient in need of cancer treatment; administering an therapeutically effective amount of an expression vector to the patient, wherein the expression vector comprises a synthetic promoter and an exogenous nucleic acid fragment operably linked to the synthetic promoter, wherein the synthetic promoter regulates the expression of an exogenous nucleic acid fragment into a protein; transforming one or more cells of the patient with the expression vector; and expressing the exogenous nucleic acid fragment in the one or more cells of the patient, wherein the exogenous nucleic acid fragment is transcribed under conditions that exist within tumor cells to produces a messenger RNA sequence that comprises a translatable sequence encoding a protein. In one aspect, the protein is survivin (baculoviral inhibitor of apoptosis repeat-containing 5 or BIRC5) or laminin subunit gamma-2 (LAMC2). In another aspect, the cancer is a metastatic tumor, a solid tumor or both. In another aspect, the cancer is a metastatic tumor selected from the group consisting of bladder, breast, cervical, colon, lung, prostate, and head and neck.

BRIEF DESCRIPTION OF THE DRAWINGS

For a more complete understanding of the features and advantages of the present invention, reference is now made to the detailed description of the invention along with the accompanying figures and in which:

FIG. 1A shows a partial portion of the BIRC5 5' regulatory sequence (SEQ ID NO: 1);

FIG. 1B shows a partial portion of the BIRC5 5' regulatory sequence comprising various promoter elements (SEQ ID NO: 2);

FIG. 2A shows a BIRC5-S0 promoter sequence (SEQ ID NO: 3), in accordance with one or more embodiments of the invention;

FIG. 2B shows a BIRC5-S1 promoter sequence (SEQ ID NO: 4), in accordance with one or more embodiments of the invention;

FIG. 2C shows a BIRC5-S2 (BIRC5-SP) or BL-2 promoter sequence (SEQ ID NO: 5), in accordance with one or more embodiments of the invention;

FIG. 2D shows a BIRC5-S3 promoter sequence (SEQ ID NO: 6), in accordance with one or more embodiments of the invention;

FIG. 2E shows a BIRC5-S3E promoter sequence (SEQ ID NO: 7), in accordance with one or more embodiments of the invention;

FIG. 2F shows a BIRC5-S4 promoter sequence (SEQ ID NO: 8), in accordance with one or more embodiments of the invention;

FIG. 3 shows a LAMC2 promoter sequence (SEQ ID NO: 9);

FIG. 4A shows a LamS1 promoter sequence (SEQ ID NO: 10), in accordance with one or more embodiments of the invention;

FIG. 4B shows a LamS1 promoter sequence (SEQ ID NO: 11), in accordance with one or more embodiments of the invention;

FIG. 4C shows a LamS2 promoter sequence (SEQ ID NO: 12), in accordance with one or more embodiments of the invention;

FIG. 4D shows a LamS2 promoter sequence (SEQ ID NO: 13), in accordance with one or more embodiments of the invention;

FIG. 4E shows a LamS3 promoter sequence (SEQ ID NO: 14), in accordance with one or more embodiments of the invention;

FIG. 4F shows a LamS3 promoter sequence (SEQ ID NO: 15), in accordance with one or more embodiments of the invention;

FIG. 7A shows the location of the CpG island relative to the two known transcription initiation sites marked with bent arrows and the location of potential regulatory sequences (A, B, C, and D). D1 is a non-translated region of the first exon, D2 is a translated part of the first exon, and D3 is a part of the first intron. PsurV is a BIRC5 gene promoter. The nucleotide sequence of the D1 fragment (SEQ ID NO: 23) is shown as bordered by dotted lines. Two putative CDE regulatory elements are marked. The ATG translation initiation codon of BIRC5 is marked in bold. The coordinates are relative to the first transcription initiation point.

FIG. 11 shows general compositions of various synthetic survivin promoters comprising repeated cell cycle regulatory elements (i.e. SurM and SurS1), in accordance with one or more embodiments of the invention;

FIG. 12 shows general compositions of various synthetic survivin promoters comprising multiple repeated core promoter regions (i.e. SurS2/BL-2, SurS3, SurS4, and SurS3E), in accordance with one or more embodiments of the invention;

DETAILED DESCRIPTION OF THE INVENTION

Figure 5:
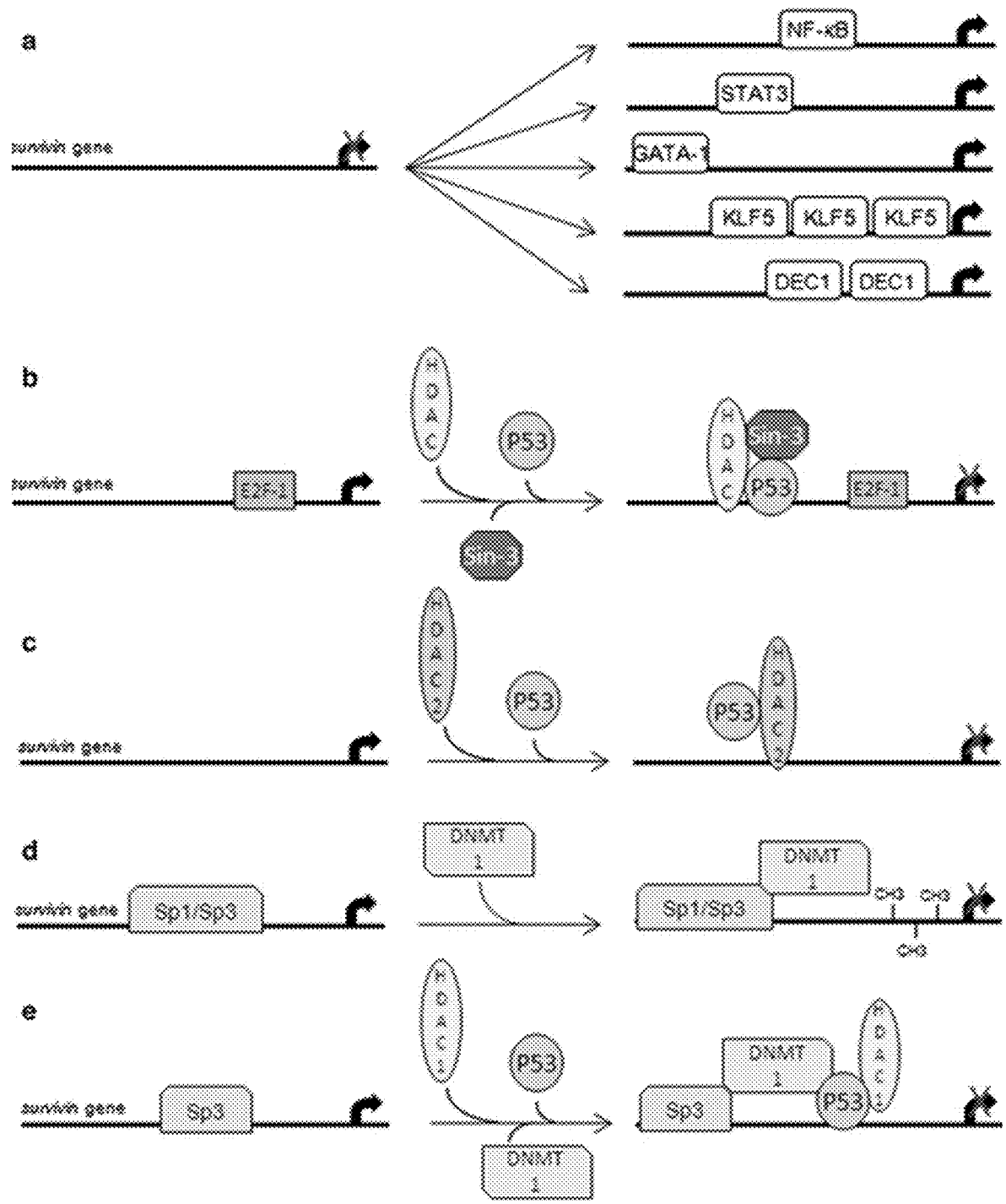
FIGS. 5A-E illustrate signaling pathways and various relationships between transcription factors and proteins that influence transcription of the survivin/BIRC5 gene.
Figure 6:
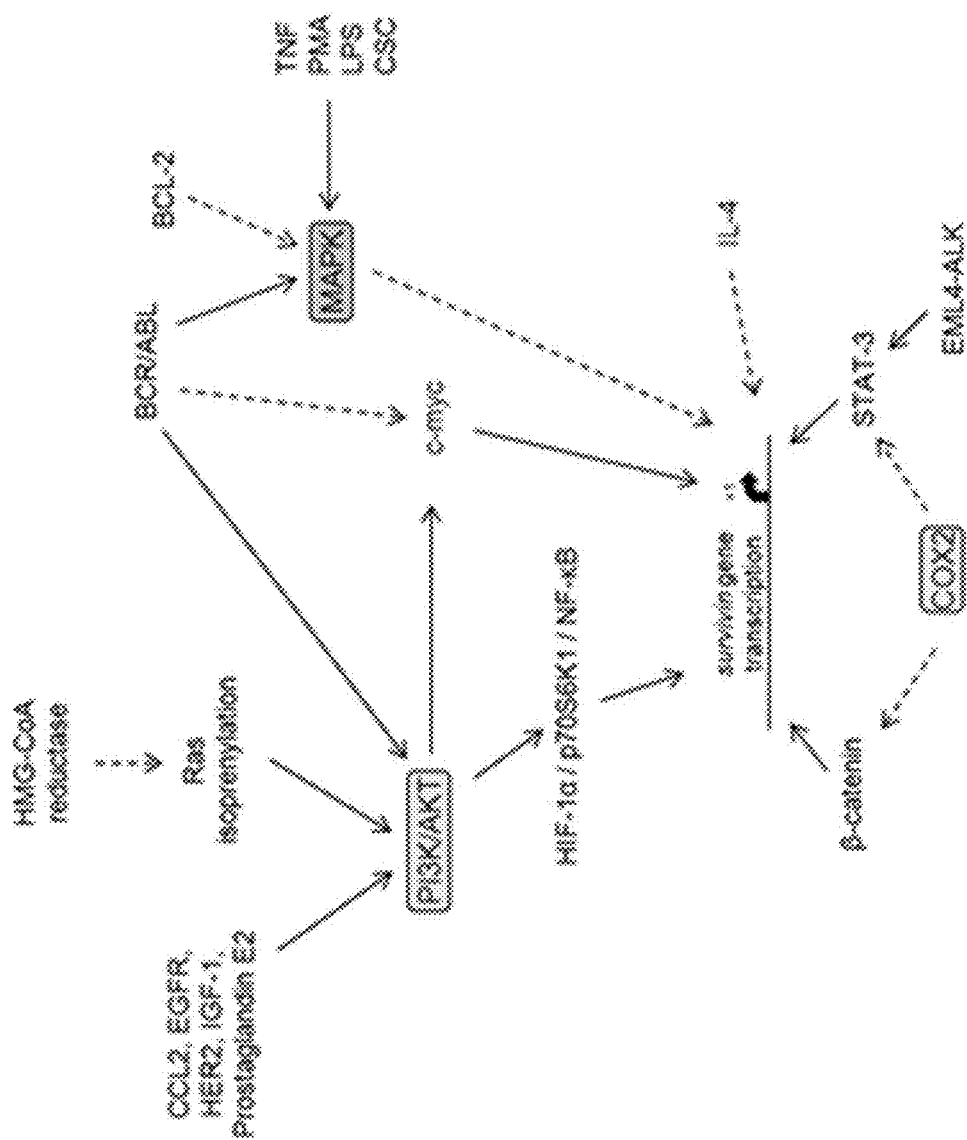
FIG. 6 illustrates elements and pathways that influence transcription of the survivin/BIRC5 gene.
Figure 7A:
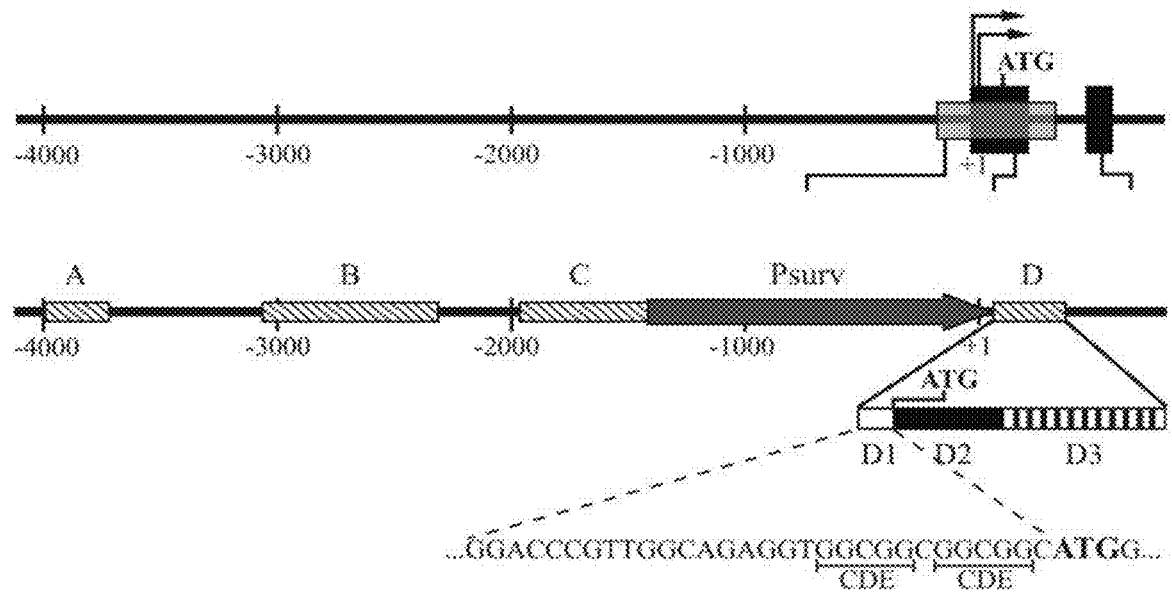
FIG. 7A shows the structure of the human survivin (BIRC5) gene promoter region. Specifically.
Figure 7B:
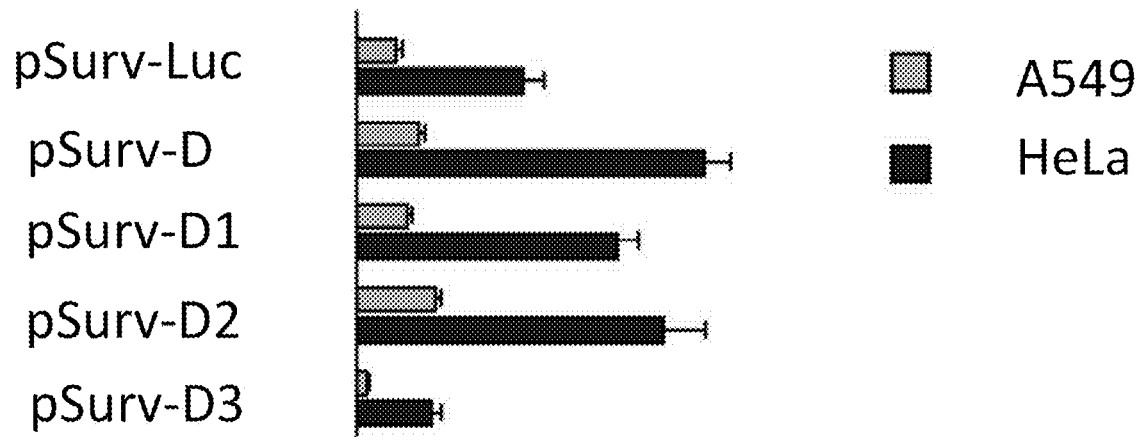
FIG. 7B shows the effect of DNA sequences from the transcribed region of the BIRC5 gene on the activity of a survivin promoter (Psurv) and a SV40 early promoter. The cells were transfected with reporter plasmids that harbored the luciferase gene under the control of either the 1498-bp survivin gene promoter (Psurv) or the SV40 early promoter. Y axis, names of the reporter constructs used for transfection. X axis, promoter activity in the A549 and HeLa cells measured as relative luciferase activity. One unit of the luciferase activity was defined as the activity in extracts of cells transfected with plasmid pGL3-BV.

Personalized medicine holds tremendous promise—promise that today remains largely unrealized. Although genomic sequencing has become significantly more affordable and accessible, its influence on patient health care has been negligible. The key to successful personalized medicine is targeted therapy guided by genomic profiles. Consequently, sequencing of patient genomes has progressed exponentially—but its influence on health care has been negligible as actionable targets are not easily identified in the many thousands of random mutations in the genome of an individual.

Thus, a highly novel and transformational GIFT (Genomics, Imaging, Function, Therapy) platform of personalized medicine has been developed using chemical genomics coupled to synthetic promoters to give genomic information meaning and generate targeted hybrid therapies. Genomic profiling begins with procurement and processing of cancer specimens and matching normal tissue from the operating room, followed by deep sequencing of DNA, mRNA and microRNA as well as chemical genomics on dissociated cells from these tissues. The information from this high throughput next-generation sequencing technology is then matched with the results from the chemical genomics using state-of-the-art computational databases to provide potential target gene(s). When a target gene has been identified, the expression of its corresponding protein in the cancer specimen is determined to see whether the protein is cancer-specific and oncogenic using in vitro cancer cell assays. If the protein is overexpressed, cancer-specific, and proves to promote oncogenesis, a synthetic promoter of the related target gene is constructed for three purposes: 1) the generation of synthetic promoter high-throughput screening assays to identify cancer-specific inhibitory FDA approved small molecules, 2) the generation of cancer-specific synthetic promoter-driven gene therapy and imaging and 3) interrogation of other related signaling pathways using RNAi and cDNA screening platforms, chemical genomics and signaling pathway technologies to learn about the biological context of the target.

For example, through the analysis of resected PNET specimens, the GIFT platform can use a synthetic insulin promoter (SHIP) for: 1) SHIP high throughput screening to identify a panel of PNET drugs, including metformin, that may be combined as a novel hybrid therapies for PNETs; 2) SHIP driven gene therapy constructs allowing the activation of therapeutic pro-drugs and $Ga^{68}$-DOTATAC and $F^{18}$ FHBG imaging; and 3) interrogation of related insulin signaling pathways using functional genomics screening to find other synergistically therapeutic targets in PNETs. Leading-edge computer modeling is typically used to test and develop life-saving, personalized hybrid therapies. Combined cancer-specific small molecules, gene therapies and RNAi therapies from these analyses may be tested in human PNET specimens, as well as genetically engineered PNET cell lines and mouse models because combined modalities have better curative chances than any alone. This platform enables highly personalized medicine delivered to the right patient at the right time in the right dose.

Many of the techniques and procedures described or referenced herein are well understood and commonly employed using conventional methodology by those skilled in the art. In the description of the preferred embodiment, reference may be made to the accompanying drawings which form a part hereof, and in which is shown by way of illustration a specific embodiment in which the invention may be practiced. It is to be understood that other embodiments may be utilized and structural changes may be made without departing from the scope of the present invention.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "tumor" in its broadest sense refers to neoplastic growth of cells of various types, illustratively including, but not restricted to squamous cell carcinoma; basal cell carcinoma; transitional cell carcinoma; adenocarcinoma; gastrinoma; cholangiocellular carcinoma; hepatocellular adenoma; hepatocellular carcinoma; renal cell carcinoma; melanoma; fibrosarcoma; myxosarcoma; liposarcoma; leiomyosarcoma; rhabdomyosarcoma; teratoma; hemangiosarcoma; Kaposi sarcoma; lymphangiosarcoma; bone osteoma; osteosarcoma; osteogenic sarcoma; chondrosarcoma; meningioma; non-Hodgkin lymphoma; Hodgkin lymphoma; and leukemia.

As used herein, the term "nucleotide" refers to individual nucleotides or varieties of nucleotides as opposed to a nucleotide sequence. The term "nucleic acid" refers to RNA or DNA molecules having more than one nucleotide in any form including single-stranded, double-stranded, oligonucleotide or polynucleotide. The term "nucleotide sequence" is used to refer to the ordering of nucleotides in an oligonucleotide or polynucleotide in a single-stranded form of nucleic acid. Illustrative examples of nucleic acid-based agents include antisense molecules such as antisense oligonucleotides and polynucleotides; catalytic nucleic acid-based agents, such as ribozymes; and nucleic acid-based aptamers.

As used herein, the terms "duplex" and "double-stranded" refer to nucleic acids characterized by binding interaction of complementary nucleotide sequences. A duplex includes a "sense" strand and an "antisense" strand. Such duplexes include RNA/RNA, DNA/DNA or RNA/DNA types of duplexes. A duplex may be formed from two nucleotide sequences which are otherwise unconnected. Alternatively, a duplex may be formed by a single-stranded nucleic acid where the single-stranded nucleic acid has substantially complementary sense and antisense regions. Such a nucleic acid forms a "hairpin" conformation when the substantially complementary sense and antisense regions are hybridized to form a duplex.

As used herein, the term "complementary" refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'. It will be recognized by one of skill in the art that two complementary nucleotide sequences include a sense strand and an antisense strand. The degree of complementarity, also called homology, between nucleic acid strands significantly affects binding of the strands to each other. An antisense strand which is substantially complementary to a sense strand hybridizes to the sense strand under high stringency hybridization conditions.

As used herein, the term "hybridization" refers to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols, 5th Ed., 2002. High stringency hybridization conditions are those that only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize. The term "specific hybridization" refers to hybridization of a particular nucleic acid to a target nucleic acid without substantial hybridization to nucleic acids other than the target nucleic acid in a cell, tissue or subject.

As used herein, the terms "expression construct" and "expression cassette" refer to a double-stranded recombinant DNA molecule containing a desired nucleic acid coding sequence encoding an DNA, RNA, siRNA or shRNA and containing appropriate regulatory elements necessary or desirable for the transcription of the operably linked coding sequence in vitro or in vivo.

As used herein, the term "regulatory element" refers to a nucleotide sequence which controls some aspect of the expression of nucleic acid sequences. Exemplary regulatory elements illustratively include an enhancer, an internal ribosome entry site, an origin of replication, a polyadenylation signal, a promoter, a transcription termination sequence, and an upstream regulatory domain, which contribute to the replication, transcription, post-transcriptional processing of a nucleic acid sequence.

As used herein, the term "operably linked" refers to connection of two or more nucleic acid molecules, including an oligonucleotide or polynucleotide to be transcribed and a regulatory element such as a promoter or an enhancer element, which allows transcription of the oligonucleotide or polynucleotide to be transcribed.

As used herein, the term "promoter" refers to a DNA sequence that can be operably linked to another nucleic acid sequence so that this other sequence is transcribed. A promoter is generally positioned upstream of a nucleic acid sequence to be transcribed and provides a site for specific binding by RNA polymerase and other transcription factors. In specific embodiments, a promoter is generally positioned upstream of the nucleic acid sequence transcribed to produce DNA, RNA, siRNA or shRNA, and provides a site for specific binding by RNA polymerase and other transcription factors.

As used herein, the term "recombinant" denotes a nucleic acid construct in which two or more nucleic acids are linked and which are not found linked in nature.

The present invention provides a synthetic DNA promoter sequence which can be operably linked to a nucleic acid sequence so that this nucleic acid sequence is transcribed in a cell. In specific embodiments, the DNA promoter sequence of the present invention is generally positioned upstream of the nucleic acid sequence transcribed to produce DNA, RNA, mRNA, siRNA or shRNA, and provides a site for specific binding by RNA polymerase and other transcription factors. This application is related to U.S. patent application Ser. No. 14/396,967, filed Oct. 24, 2014 and entitled "SYNTHETIC PROMOTER FOR MODULATING GENE EXPRESSION", the contents of which are incorporated herein by reference.

The present invention also relates to a method of gene targeting or homologous recombination in cells and the resulting primary, secondary, or immortalized cells. The present invention is particularly useful for turning on the expression of genes, which comprise native transcription units which are sufficiently large that they are difficult to isolate and express, or for turning on genes for which the entire protein coding region is unavailable or has not been cloned. The present invention also describes a method by which homologous recombination is used to convert a gene into a cDNA copy, devoid of introns, for transfer into yeast or bacteria for in vitro protein production.

The synthetic promoters are cancer-specific and based upon the individual's actionable genomic analysis. Therefore, in various embodiments, the promoters may be used, for example, to: diagnose the presence of cancer for screening and recurrence; localize the cancer using PET CT imaging and Molecular Contrast™, effectively target cancer therapies for each individual; develop high throughput chemical library assays to identify optimal combinations of U.S. Food and Drug Administration (FDA)-approved small molecule cancer drugs for therapy in a clinically relevant time frame; develop high throughput chemical library assays to identify novel small molecule cancer therapies; reduce toxicity caused by current therapies for each patient; and track response to therapy.

There are unique and practical clinical applications for a synthetic promoter of a target gene identified through actionable genomic analysis to generate hybrid therapies. In illustrative experiments, the promoters have been shown to result in the identification of FDA-approved therapies for cancer, as well as the ability to screen for the presence of cancer, localize cancer via molecular PET-CT imaging, and ablate cancer in a targeted manner by using a single vector ignited by the target gene synthetic promoter.

In various illustrative implementations, the synthetic promoter provides for synthetic promoter high-throughput screening assays to identify the target gene-specific inhibitory FDA-approved, repurposed small molecules and novel small molecules. The BL promoter may also be used for target gene-specific synthetic promoter-driven synthetic biomarkers for screening and diagnosis of cancer. The BL promoter may also be used for target gene-specific synthetic promoter-driven gene therapy for cancer. The synthetic promoter may also be used for the interrogation of other related signaling pathways using RNAi and cDNA screening platforms, chemical genomics and other signaling pathway elucidation technologies to learn about the biological context of the target. Any gene/RNAi therapy can be delivered using the platform comprising, e.g., a pUMVC3 backbone, microRNA 30 backbone delivered by decorated, reversibly masked liposomes. The platform can be used for ex vivo treatment of cancer cells and islets, as well as multiple cycles of intravenous therapy in patients.

This invention disclosed herein has a number of synthetic (i.e. non-naturally occurring) nucleic acid embodiments derived from the BIRC5 and LAMC2 promoter that are discussed in detail in the sections below. BIRC5 related embodiments of the invention include a nucleic acid comprising a synthetic BIRC5 promoter having two or more nucleotide sites (e.g. transcription factor binding sequence motifs) shown in FIGS. 1 and 2 such as a site at which mRNA transcription is initiated comprising GGC (of SEQ ID NO: 1); and/or a SP1 motif comprising GGC (residues 1410-1412 of SEQ ID NO: 1); and/or a CDE motif comprising GCC (residues 1300-1302 of SEQ ID NO: 1); and/or an EGR1 motif comprising GGG (residues 1223-1225 of SEQ ID NO: 1); and/or a p53 motif comprising TCC (residues 1391-1393 of SEQ ID NO: 1); and/or an E2F/Rb motif comprising CCC (residues 1401-1403 of SEQ ID NO: 1). Typically the nucleotide sequence motifs are separated by 0 to 50 or 100 nucleotides; and the BIRC5 promoter transcribes a heterologous nucleic acid sequence operatively linked to the BIRC5 promoter (i.e. actively transcribes the heterologous sequences). Embodiments of the invention include a nucleic acid comprising a BIRC5 promoter as shown in SEQ ID NO: 1 linked to a heterologous nucleic acid sequence.

Embodiments of the invention include a synthetic BIRC5 promoter further comprising a heterologous nucleic acid sequence operatively linked to the synthetic BIRC5 promoter. Optionally the heterologous nucleic acid encodes a naturally occurring polypeptide such as a growth factor or a factor which induces apoptosis, and the synthetic BIRC5 promoter transcribes the gene to a greater level than the naturally occurring BIRC5 promoter. In certain embodiments of the invention, the synthetic BIRC5 promoter comprises less than 1000, 750, 500 or 250 nucleotides; and/or exhibits at least an 80% sequence identity to the 100, 200, 300, 400 or 500 nucleotides immediately upstream of the transcription start site of the BIRC5 sequence of SEQ ID NO: 1. An expression vector comprising a synthetic BIRC5 promoter and a host cell (e.g. *Escherichia coli*, yeast or human cancer cell) comprising this vector. Embodiments of the invention include a composition of matter comprising the synthetic BIRC5 promoter and a pharmaceutically acceptable carrier. In an illustrative working embodiment of this invention, we show that the systemic delivery of AAV2 vectors with a reporter gene coupled to a BIRC5 promoter into PANC-1 xenograft model results in strong tumor signal in tumor and reduced non-specific signals in AAV2RGD-GLuc group (4.5 mm tumor) (A) vs large non-specific signal but no signals in tumor in AAV2WT CMV-GLuc vector group (B).

LAMC2 related embodiments of the invention include a nucleic acid comprising a synthetic LAMC2 promoter having two or more nucleotide sites (e.g. transcription factor binding sequence motifs) shown in FIGS. 3 and 4 such as a site at which mRNA transcription is initiated comprising CAC (residues 1228-1230 of SEQ ID NO: 9); an SP1 binding sequence comprising AGG (residues 1133-1135 of SEQ ID NO: 9); an AP1 binding sequence comprising TCA (residues 1182-1185 of SEQ ID NO: 9); a NFκB binding sequence comprising ACT (residues of SEQ ID NO: 9); and/or a CREB binding sequence comprising CGT (residues of SEQ ID NO: 9). Typically the nucleotide sequence motifs are separated by 0 to 50 or 100 nucleotides; and the LAMC2 promoter transcribes a heterologous nucleic acid sequence operatively linked to the LAMC2 promoter (i.e. actively transcribes the heterologous sequences). Embodiments of the invention include a nucleic acid comprising a LAMC2 promoter as shown in SEQ ID NO: 9 linked to a heterologous nucleic acid sequence.

Embodiments of the invention include a synthetic LAMC2 promoter further comprising a heterologous nucleic acid sequence operatively linked to the synthetic LAMC2 promoter. Optionally the heterologous nucleic acid encodes a naturally occurring polypeptide such as a growth factor or a factor which induces apoptosis, and the synthetic LAMC2 promoter transcribes the gene to a greater level than the naturally occurring LAMC2 promoter. In certain embodiments of the invention, the synthetic LAMC2 promoter comprises less than 1000, 750, 500 or 250 nucleotides; and/or exhibits at least a 80% sequence identity to the 100, 200, 300, 400 or 500 nucleotides immediately upstream of the transcription start site of the LAMC2 sequence of SEQ ID NO: 9. An expression vector comprising a synthetic LAMC2 promoter and a host cell (e.g. *Escherichia coli*, yeast or human cancer cell) comprising this vector. Embodiments of the invention include a composition of matter comprising the synthetic LAMC2 promoter and a pharmaceutically acceptable carrier.

Further aspects of the BIRC5 and LAMC2 promoters are discussed below.

BL-2 (survivin/BIRC5) Promoter

BIRC5 or survivin, is a member of the inhibitor of apoptosis (IAP) family of proteins. BIRC5 is a key oncologic regulator of apoptosis that is over-expressed/upregulated in most cancers, including pancreatic cancer, but not in normal cells. 77-94% of pancreatic ductal adenocarcinoma cells (PDAC) have BIRC5 overexpression, which is rarely seen in benign tissues. Elevated BIRC5 expression has been commonly associated with enhanced proliferation, reduced levels of apoptosis, resistance to chemotherapy, and increased rates of tumor recurrence.

In one aspect of the invention, a BIRC5 synthetic promoter (BL-2) generated from the endogenous promoter of BIRC5 is provided that is 1000× more powerful than the endogenous promoter and also more powerful than the cytomegalovirus (CMV) promoter in stimulating gene expression. The BL-2 promoter is cancer specific and does not get activated in normal cells whereas the CMV promoter that is frequently used to drive gene therapy vectors is ubiquitous and is activated in all cells. The BL-2 synthetic promoter is more highly specific for cancer, especially pancreatic cancer, since it is not expressed in normal cells, including islets of Langerhans, and therefore is less toxic. This represents personalized medicine that can target cancer. The technique to generate the BIRC5 synthetic promoter (BL-2) and its uses are similar to U.S. patent application Ser. No. 14/396,967, which describes a synthetic BL-1 promoter for the insulin gene. The BL-2 promoter described herein is just as powerful as this synthetic BL-1 promoter, however it is cancer specific and does not get activated in normal cells whereas the BL-1 promoter is activated in normal islet cells which therefore can lead to hyperglycemia and diabetes as a toxic effect.

The BL-2 promoter may be used to drive reporter genes for high throughput screening of FDA approved chemicals libraries and for novel chemical libraries. In doing so, small molecules and FDA approved drugs specific for the BL-2 promoter and cancer may be identified that can be used for cancer therapy, as well as cancer specific gene therapy and imaging using theranostic (combined term for imaging and therapy) genes and diagnosis of cancer using synthetic biomarkers. Commercial applications include its use in toxicity assays for pharmaceutical companies and basic research programs for cancer.

More specifically, the synthetic promoter may be used in various embodiments, including cancer-specific gene therapy, cancer specific RNAi therapy, and high throughput screening to identify drugs that will inhibit BIRC5 and cancer proliferation. The importance of this promoter is that it is highly specific for cancer cells, especially pancreatic cancer, and is not expressed in normal cells. For example in one embodiment, BL-2 is used to drive a Gaussia luciferase-2A-thymidine kinase vector for screening and localization for early detection of pancreatic cancer.

BL-3 (LAMC2) Promoter

LAMC2 is a key oncologic regulator of apoptosis that is also over-expressed in most cancers, including pancreatic cancer, but not in normal cells. In one aspect of the invention, a LAMC2 synthetic promoter (BL-3) generated from the endogenous promoter of LAMC2 is provided that is 1000× more powerful than the endogenous promoter and also more powerful than the cytomegalovirus (CMV) promoter in stimulating gene expression. The promoter competes with the CMV promoter, which is non-specific for cancer. The BL-3 synthetic promoter is more highly specific for cancer, especially pancreatic cancer, since it is not expressed in normal cells, including islets of Langerhans, and therefore is less toxic. The technique to generate the LAMC2 synthetic promoter (BL-3) and its uses are similar to U.S. patent application Ser. No. 14/396,967, which describes a synthetic BL-1 promoter for the insulin gene. However, the synthetic BL-1 promoter is expressed in islets of Langerhans, which therefore can lead to hyperglycemia and diabetes as a toxic effect.

The synthetic promoter may be used in various embodiments, including cancer-specific gene therapy, cancer specific RNAi therapy, and high throughput screening to identify drugs that will inhibit LAMC2 and cancer proliferation. The importance of this promoter is that it is highly specific for cancer cells, especially pancreatic cancer, and is not expressed in normal cells. For example in one embodiment, BL-3 is used to drive a Gaussia luciferase-2A-thymidine kinase vector for screening and localization for early detection of pancreatic cancer.

Illustrative Embodiments of the Invention

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not limit the scope of the invention.

Illustrative embodiments of the invention provide a synthetic promoter or nucleic acid construct having selected transcriptional motifs. In such embodiments of the invention, the synthetic promoter modulates transcription of an exogenous nucleic acid operatively linked to this promoter.

In one embodiment, the synthetic promoter is a BL-2 promoter comprising at least one of an EGR1 binding site motif GAGGGGGCG (SEQ ID NO: 16) and a P53 binding site motif GGGCGTGCGCTCCCGACATGCCC (SEQ ID NO: 17) (see, e.g. FIGS. 1A-B). In certain instances, the transcriptional motifs are separated by 0 to 41. In other instances, the transcriptional motifs are separated by 0 to 151 nucleotides. In one aspect, the BL-2 promoter comprises at least two, at least three, or at least four repeats of a nucleotide sequence spanning positions −327 to −1 of the human BIRC5/survivin promoter gene (SEQ ID NO: 18) (see, e.g. FIGS. 11-12). In one embodiment, the BL-2 promoter comprises 2 repeats of the nucleotide sequence spanning positions −327 to −1 of the human BIRC5/survivin promoter gene (SEQ ID NO: 5). In certain instances, the BL-2 promoter further includes an ATG motif. In other instances, the BL-2 promoter includes a nucleotide sequence spanning positions +1 to +128 of the human BIRC5/survivin promoter gene (SEQ ID NO: 20).

Figure 20:
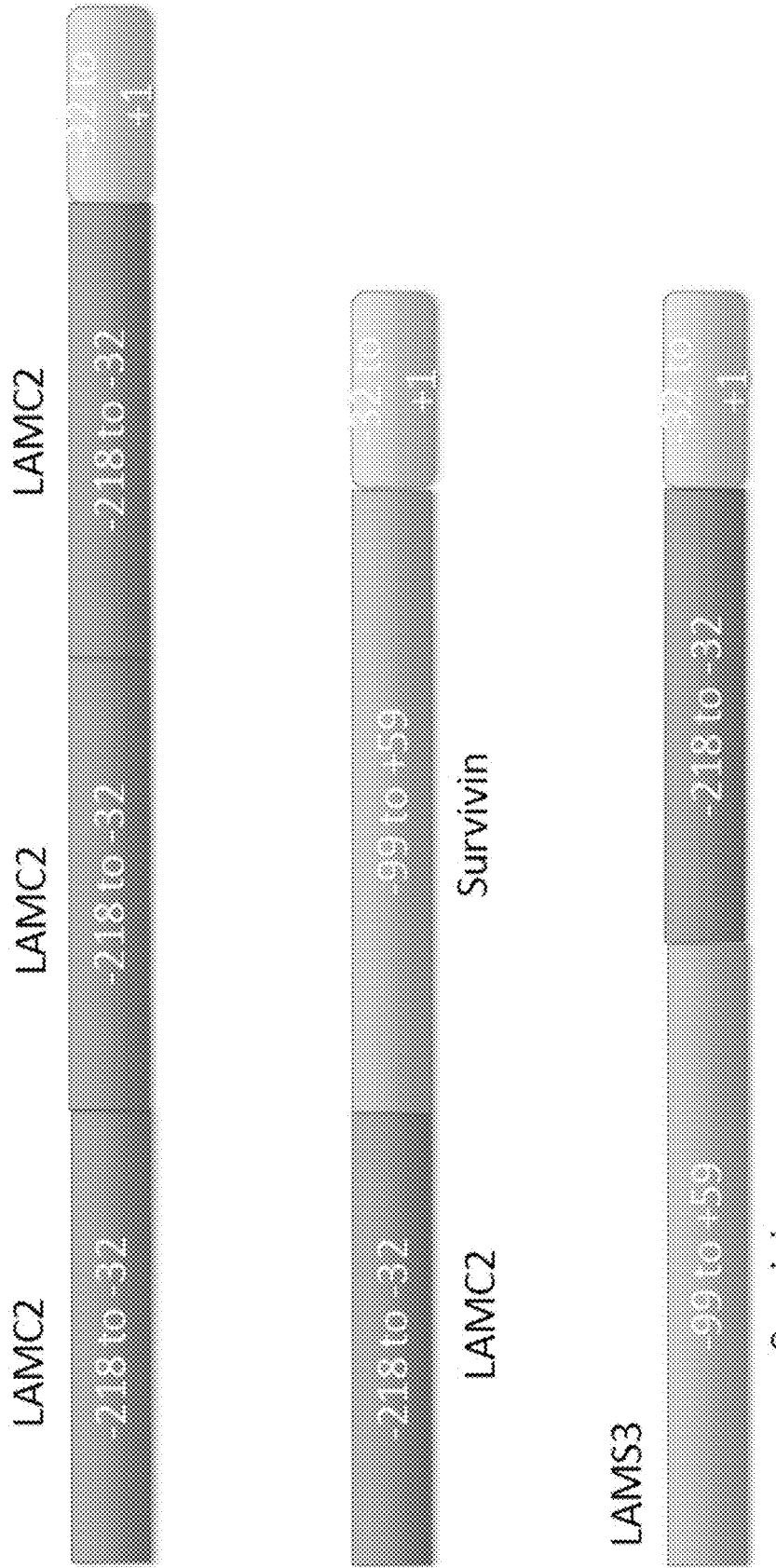
FIG. 20 shows general compositions of various synthetic LAMC2 promoters (i.e. LAMS1 and LAMS3), in accordance with one or more embodiments of the invention.
Figure 21:
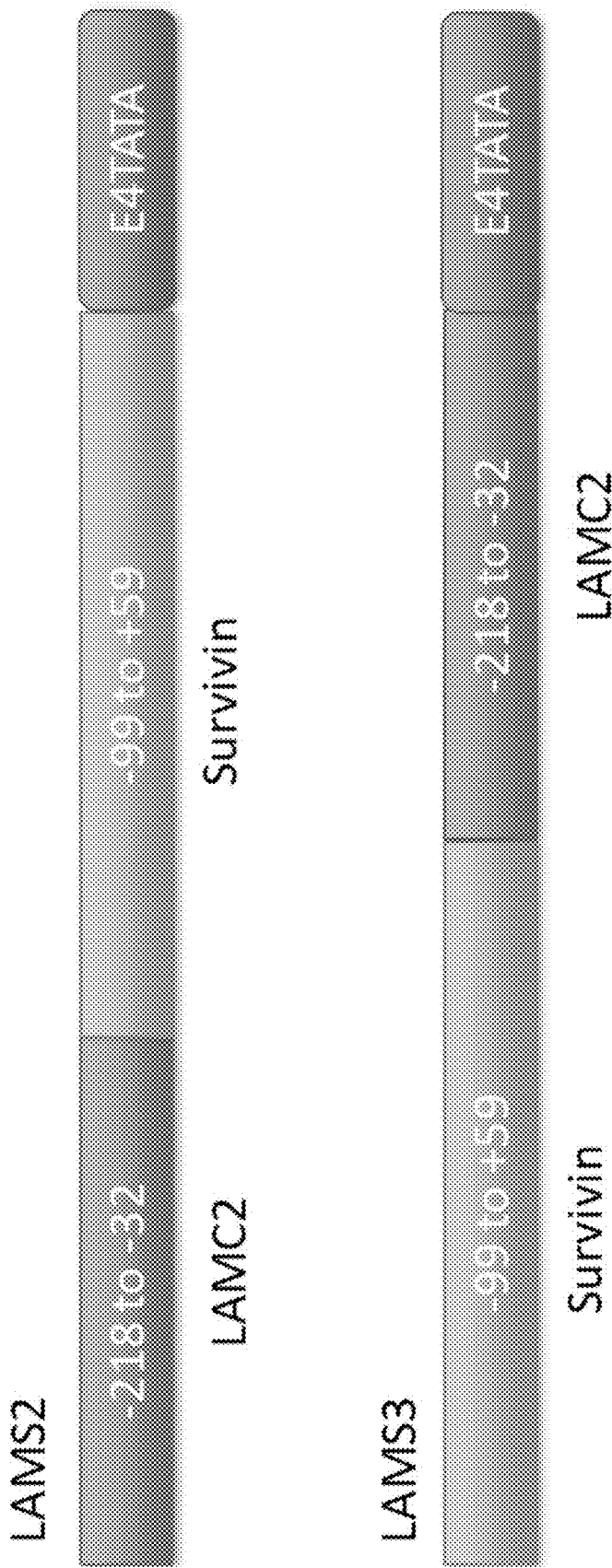
FIG. 21 shows general compositions of various synthetic LAMC2 promoters (i.e. LAMS2 and LAMS3), in accordance with one or more embodiments of the invention.
Figure 22:
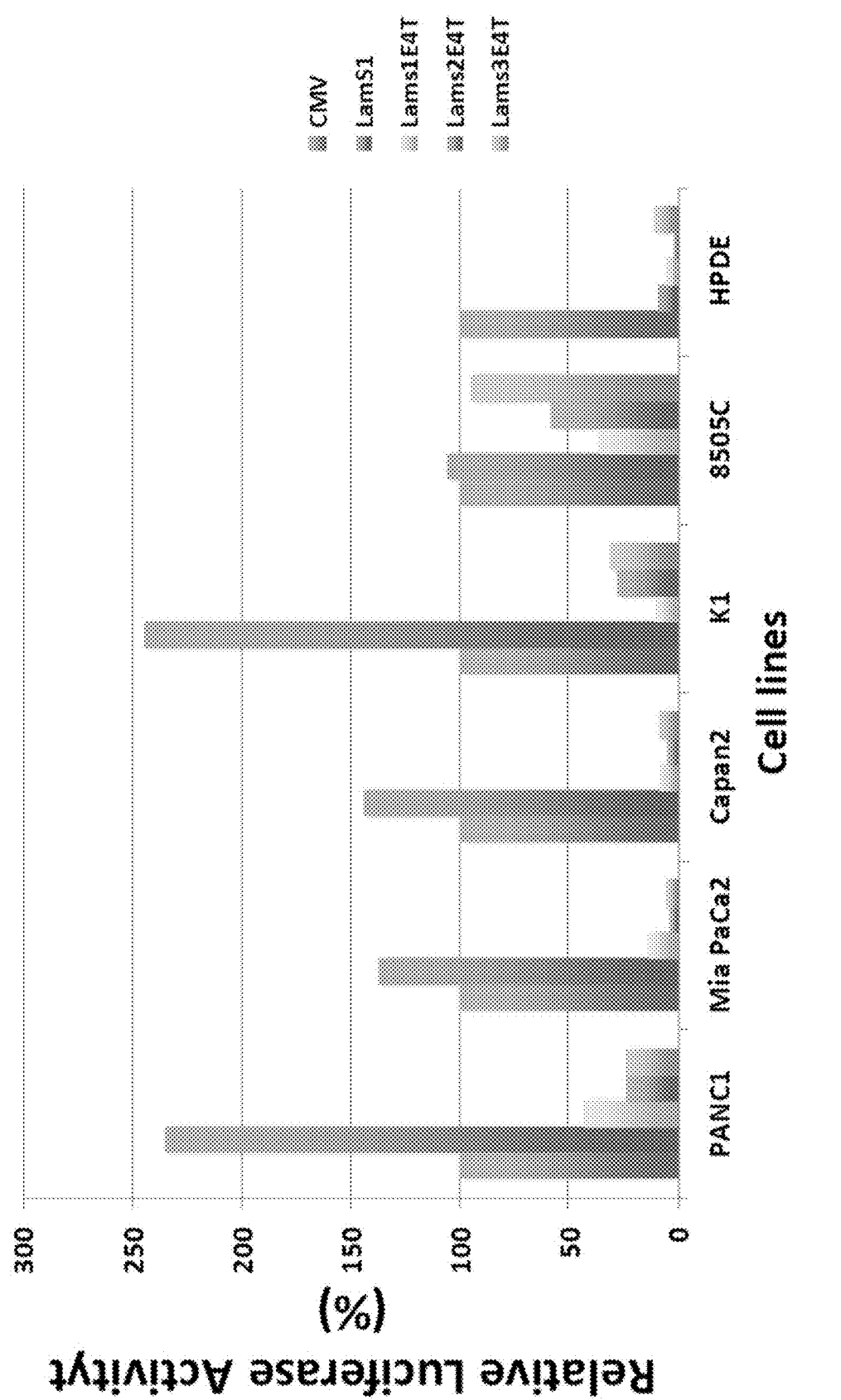
FIG. 22 is a graph showing the relative luciferase activity of various synthetic LAMC2 promoters (i.e. LamS1, Lams1E4T, Lams2E4T, and Lams3E4T) and CMV in various cell lines, in accordance with one or more embodiments of the invention. LamS1 (BL-3) is shown to result in the greatest amount of luciferase activity.
Figure 23:
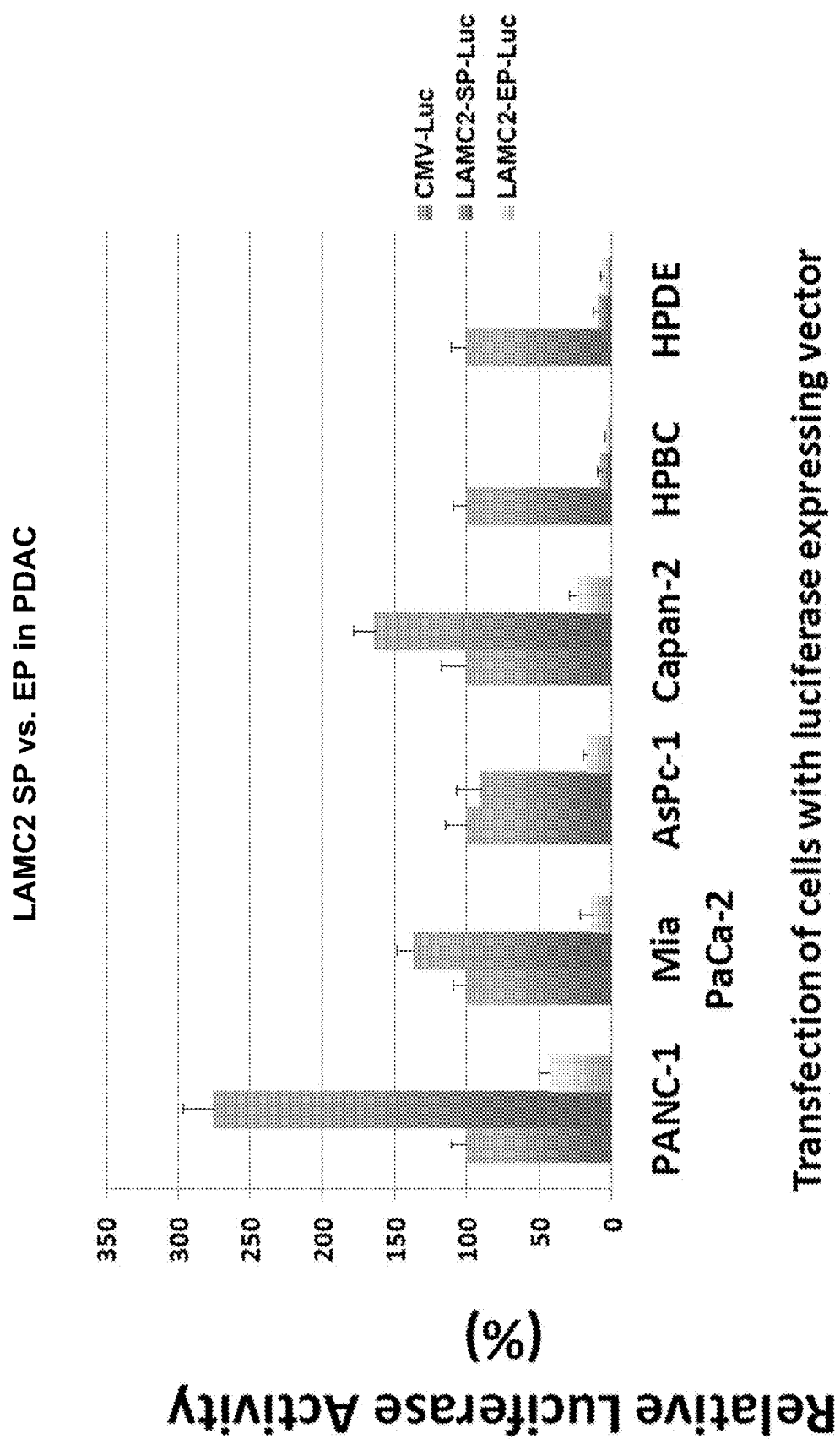
FIG. 23 is a graph showing the relative luciferase activity of an endogenous LAMC2 promoter (LAMC2-EP-Luc), a synthetic LAMC2 promoter (LAMC2-SP-Luc), and CMV in various cell lines, in accordance with one or more embodiments of the invention. LAMC2-SP-Luc (BL-3) is shown to result in the greatest amount of activity in comparison to an endogenous LAMC2 promoter and a CMV promoter in pancreatic ductal adenocarcinoma cells (PANC-1, MIA PaPc2, AsPc-1, and Capan-2) but no activity in human primary pancreatic epithelial cells (HPPE) and human pancreatic duct epithelial cells (HPPE)
Figure 24:
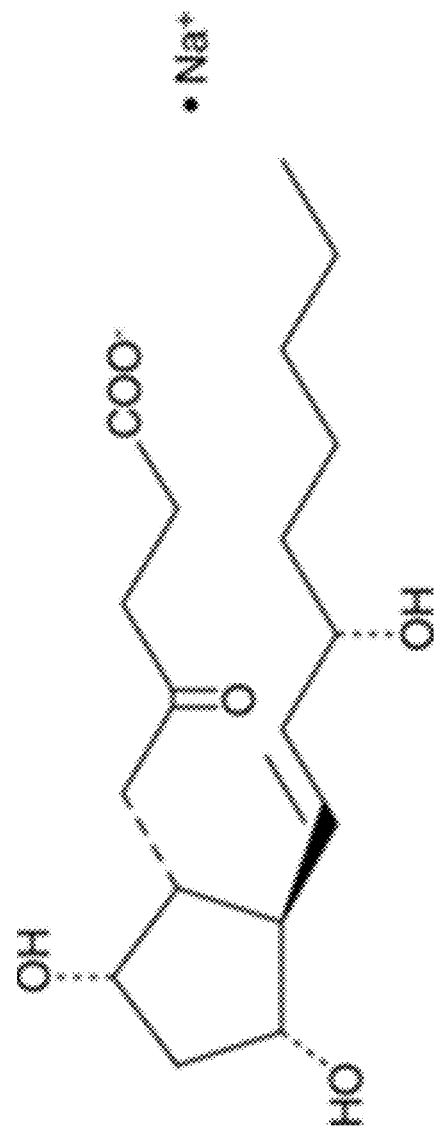
FIG. 24 illustrates the chemical structure of 2,3-dinor-6-keto Prostaglandin $F_{1\alpha}$ (PFG1a)
Figure 25:
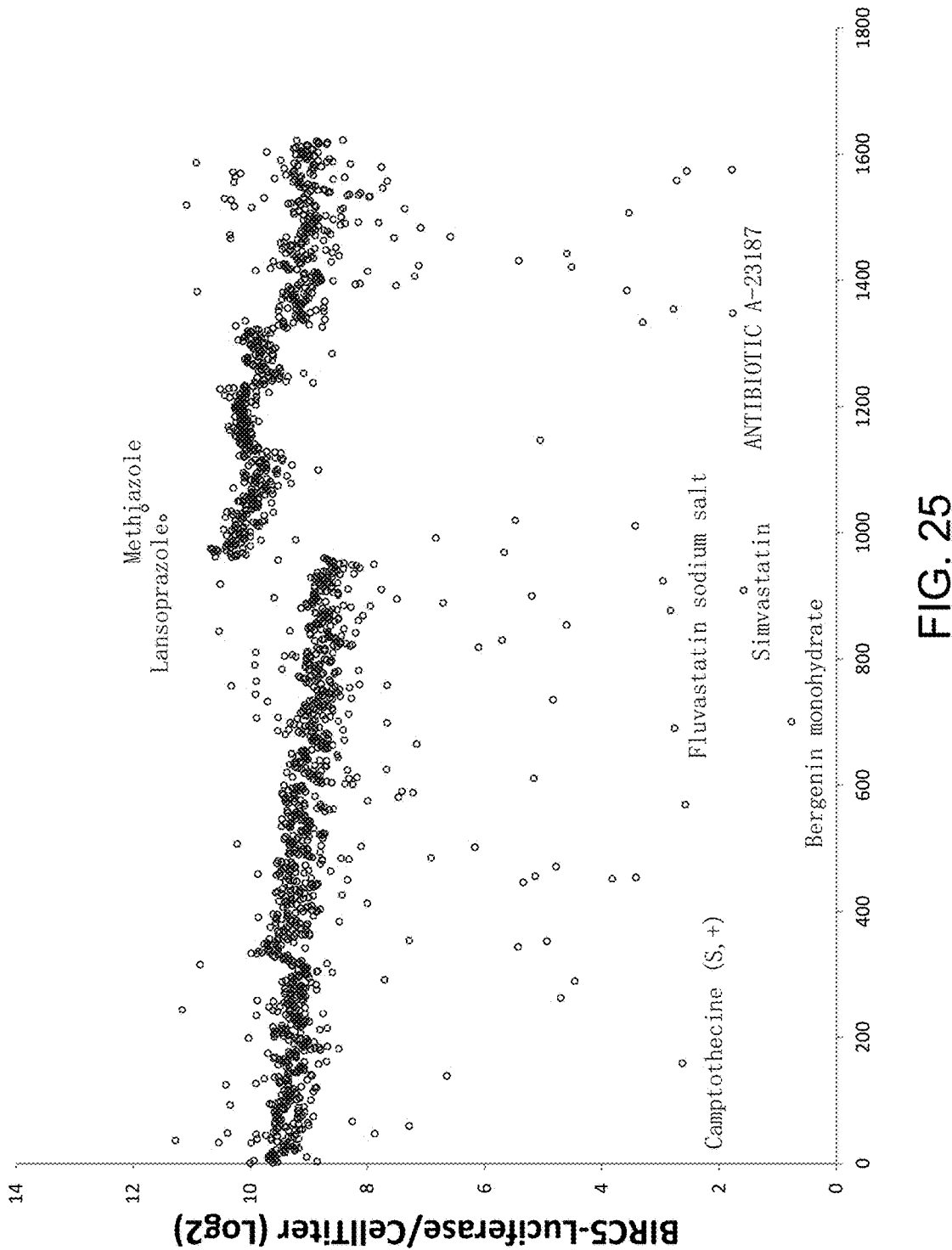
FIG. 25 is a graph showing the results from a BIRC5-luciferase FDA-approved drug screening assay, in accordance with one or more embodiments of the invention.
Figure 26:
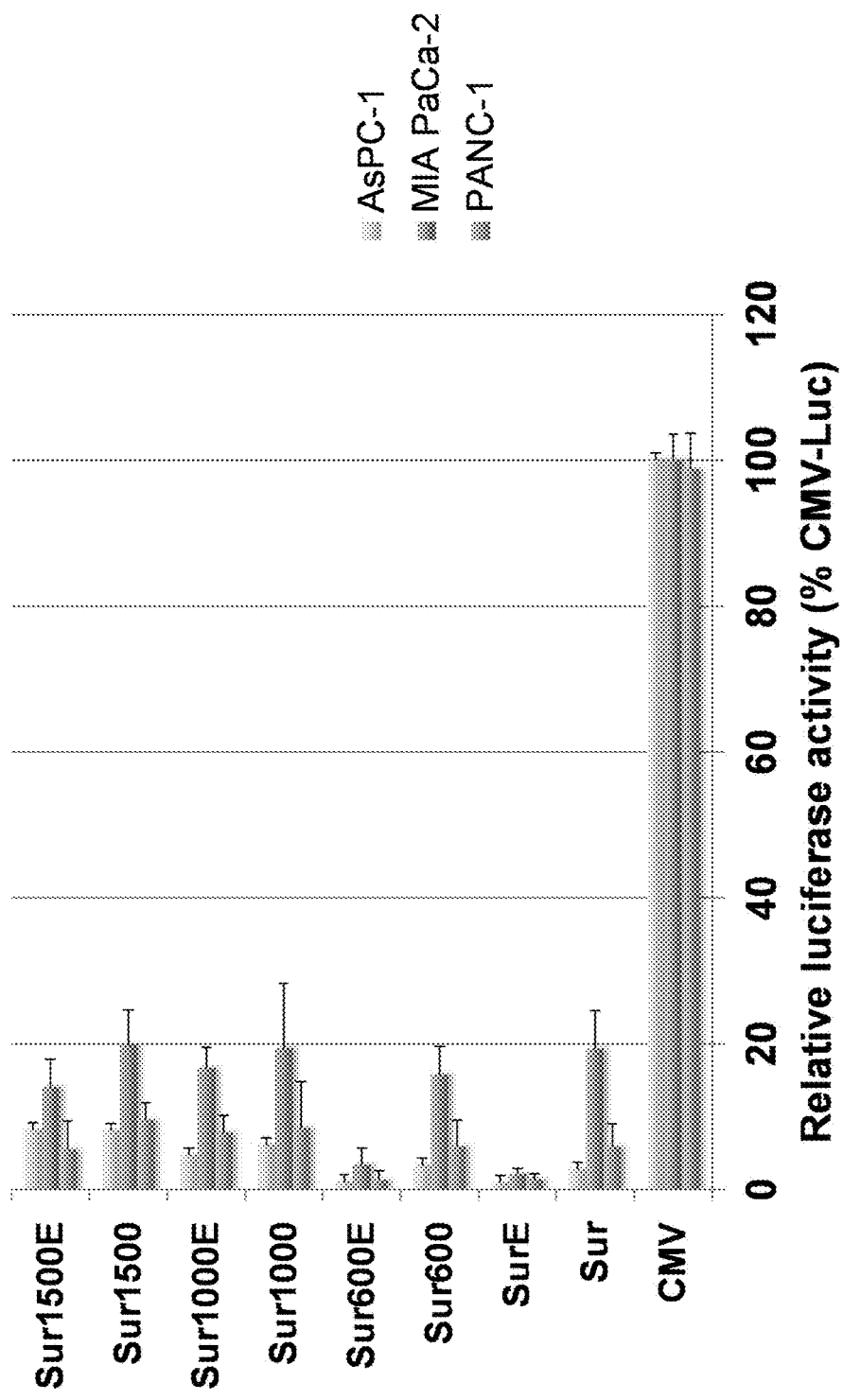
FIG. 26 is a graph showing the activities of survivin promoter fragments produced by extension of translational region (1st exon sequence), in accordance with one or more embodiments of the invention.
Figure 27:
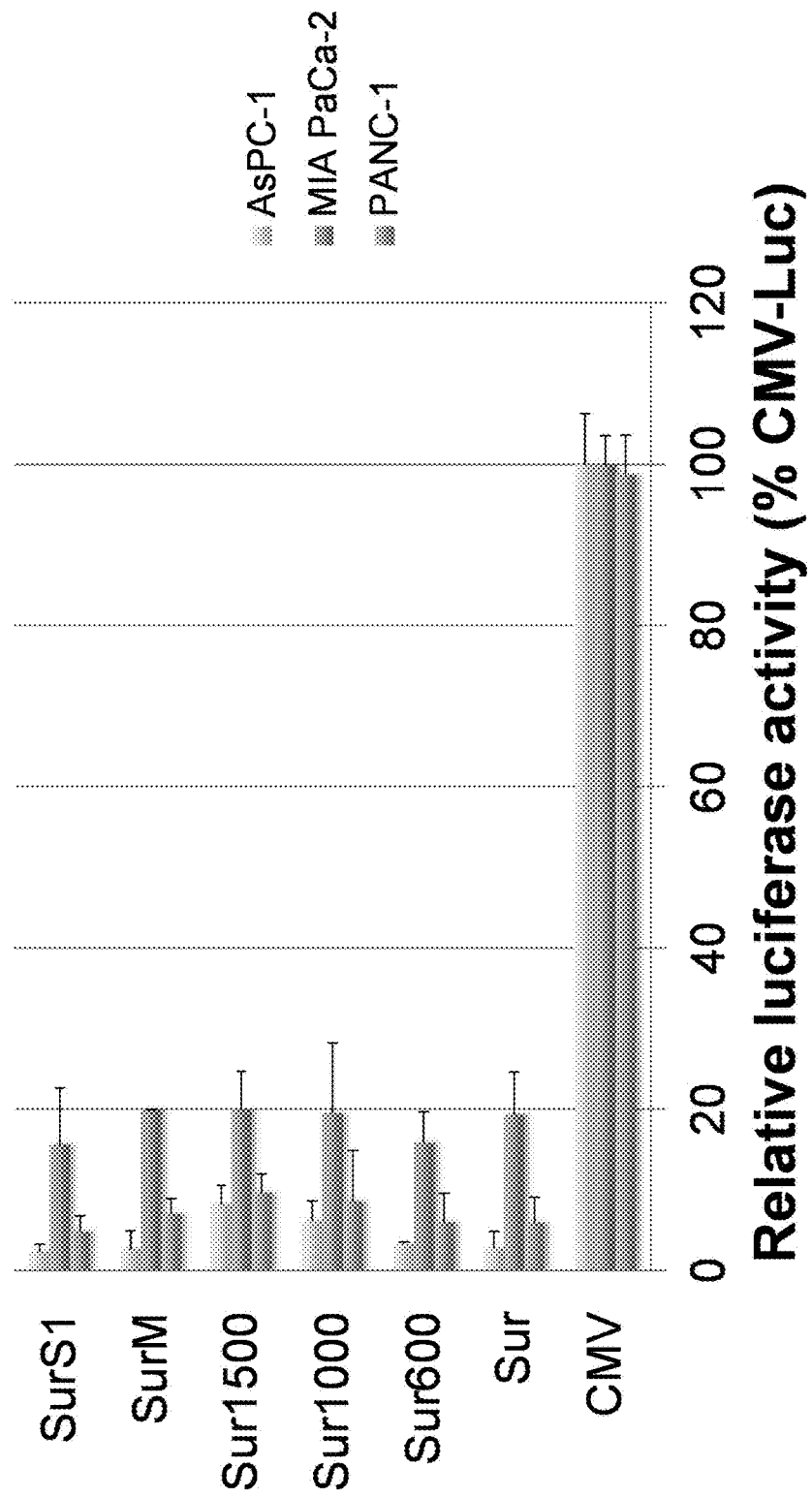
FIG. 27 is a graph showing the activities of survivin promoter fragments produced by repeated transcriptional regulatory elements, in accordance with one or more embodiments of the invention.
Figure 28:
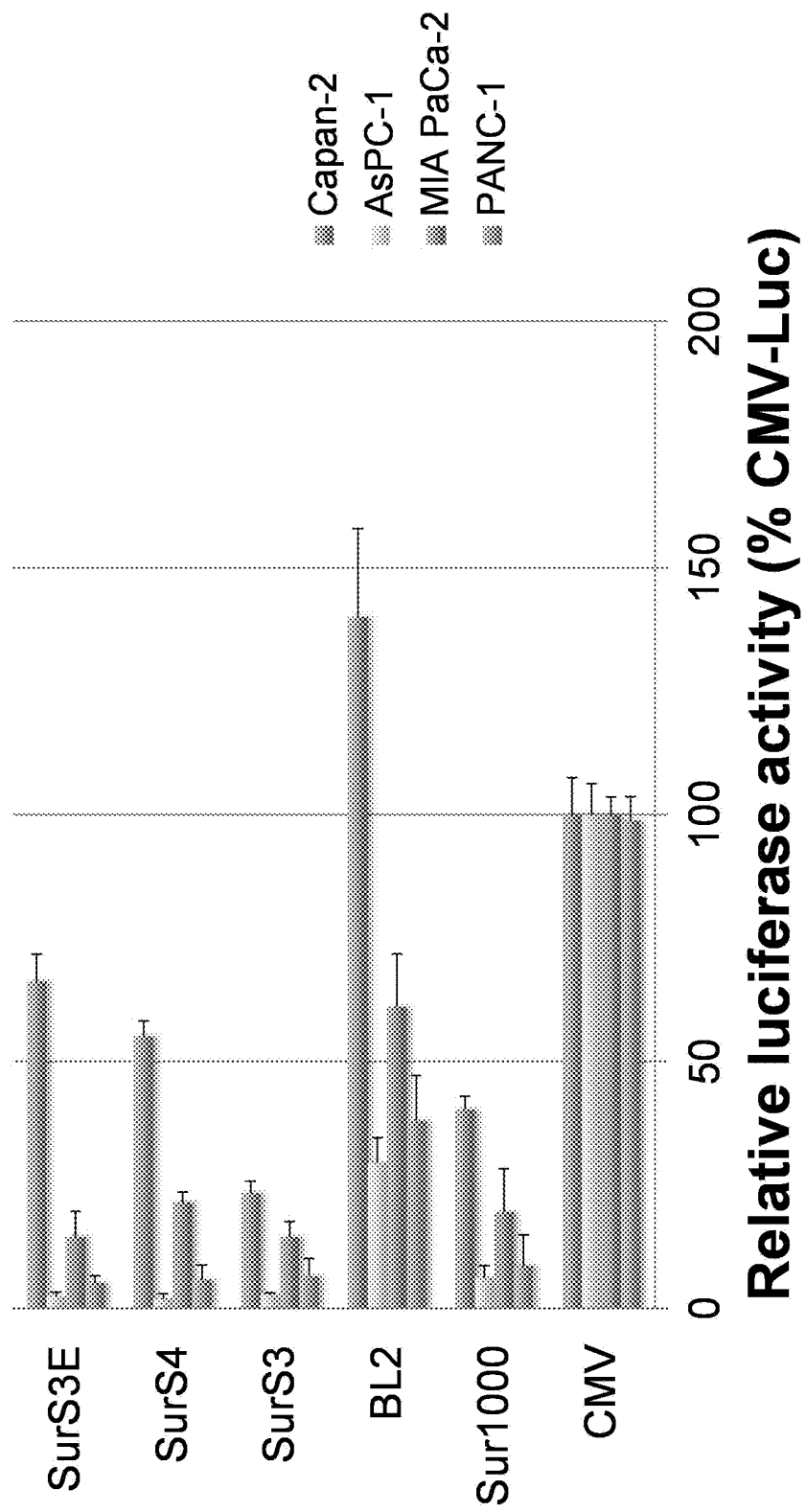
FIG. 28 is a graph showing the activities of synthetic BL-2 promoter produced by multiply repeated core promoter region, in accordance with one or more embodiments of the invention.
Figure 29:
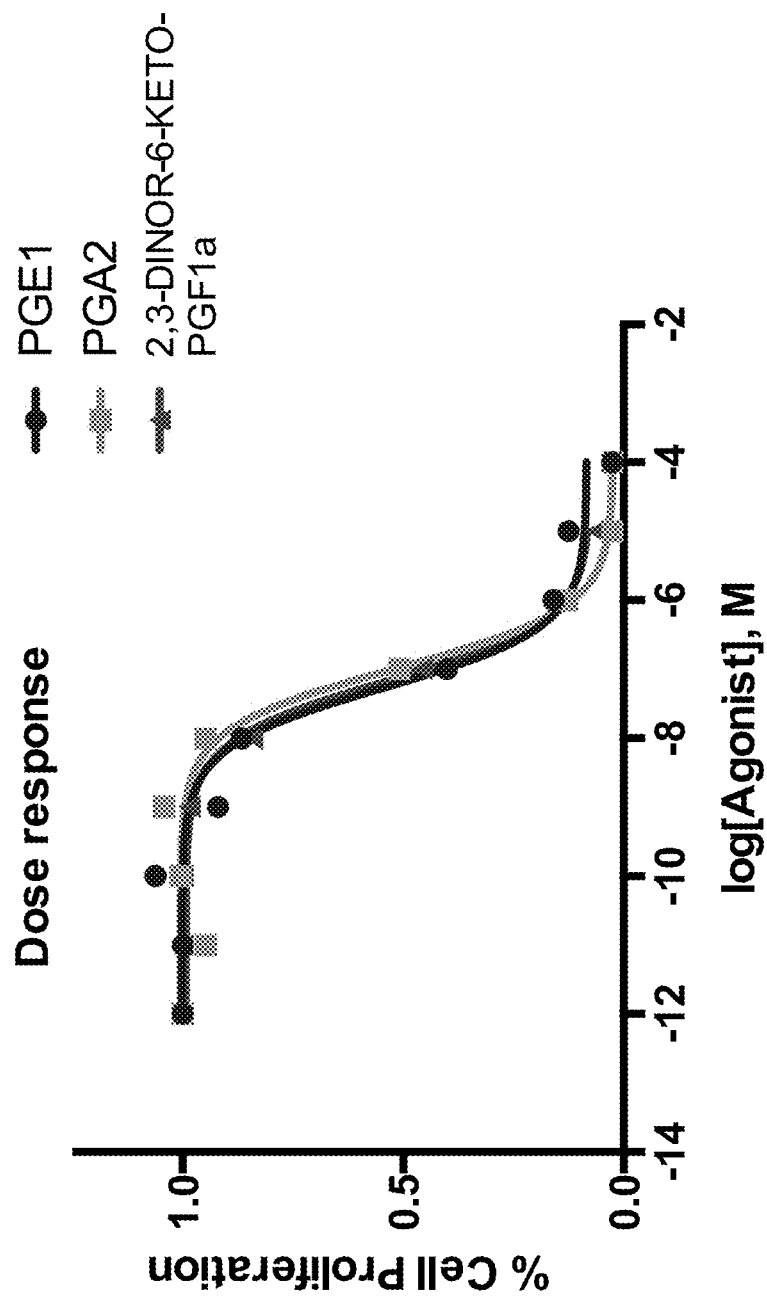
FIG. 29 is a graph showing the dose response of 2,3-dinor-6-keto Prostaglandin $F_{1\alpha}$, in accordance with one or more embodiments of the invention.
Figure 30:
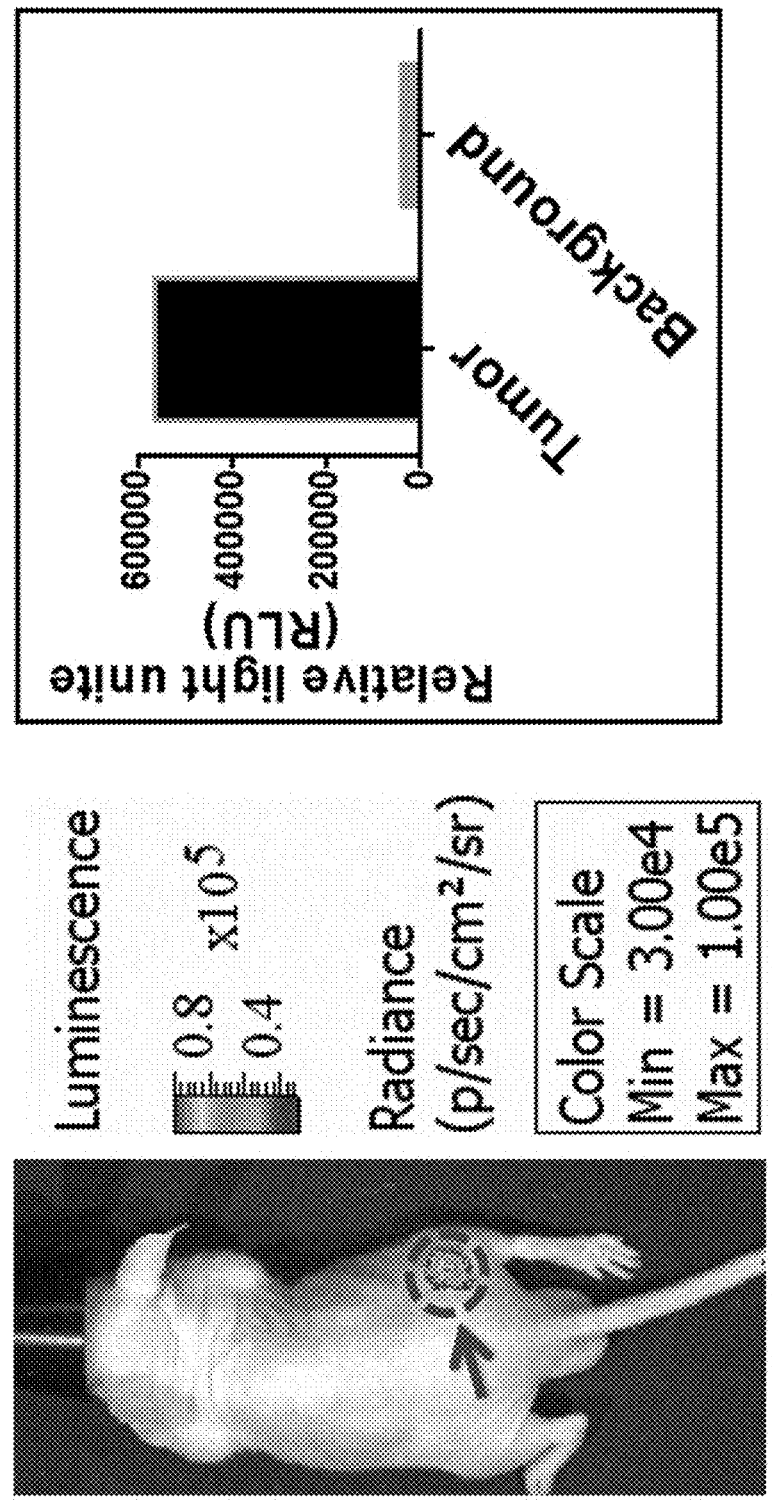
FIG. 30 Provides data showing that the systemic delivery of AAV2 vectors into PANC-1 xenograft model results in strong tumor signal in tumor and reduced non-specific signals in AAV2RGD-GLuc group (4.5 mm tumor) (A) vs large non-specific signal but no signals in tumor in AAV2WT CMV-GLuc vector group (B).

In another aspect, the synthetic promoter or nucleic acid construct is a BL-3 promoter comprising at least three repeats a nucleotide sequence spanning positions −218 to −32 of the human LAMC2 promoter gene (SEQ ID NO: 12) (see, e.g. FIG. 20). In certain instances, the BL-3 promoter further includes a nucleotide sequence spanning positions −32 to +1 of the human LAMC2 promoter gene (SEQ ID NO: 22). In one or more embodiments, the BL-3 promoter comprises a nucleotide sequence spanning positions −218 to −32 of the human LAMC2 promoter gene (SEQ ID NO: 21) and a nucleotide sequence spanning positions −99 to +59 of the BIRC5/survivin promoter gene (SEQ ID NO: 19) (see, e.g. FIGS. 20-21). In one instance, the BL-3 promoter further includes a nucleotide sequence spanning positions −32 to +1 of the human LAMC2 promoter gene (SEQ ID NO: 22) or an E4 TATA motif.

The positions as described herein are the relative positions to the transcription initiation site, which is defined as the +1 position. Furthermore, in various embodiments, the nucleotide sequences described include truncates and mutations thereof which comprise at least 80%, at least 90%, at least 95%, or at least 99% of the nucleotides of the original sequence.

In aspects of the invention, a heterologous nucleic acid is operatively linked to the synthetic promoter. Optionally, the heterologous nucleic acid encodes a polypeptide having an ability to modulate growth of a cell expressing said polypeptide. A variety of genes can be linked to the synthetic promoter.

Embodiments of the invention include sequences, vectors and methods that are designed to inhibit the expression of an endogenous gene, for example by using a synthetic promoter driven shRNA. In addition, certain embodiments of the invention include combination vectors, in which multiple gene targets are either delivered and/or knocked down using embodiments of the synthetic promoter.

In certain embodiments of the invention, the synthetic promoter is operatively coupled to a suicide gene such as thymidine kinase. In this context, transfection of the herpes simplex virus type-1 thymidine kinase gene (HTK), given in combination with the drug ganciclovir (GCV), is the most commonly used cancer gene therapy system to date, both in experimental models and clinical trials. See J. Gomez-Navarro et al., "Gene therapy for cancer," European Journal of Cancer, vol. 35, pp. 867-885 (1999). HTK, whose substrate specificity is distinct from that of cellular thymidine kinases, can convert GCV to the toxic phosphorylated form, specifically killing the cells that express HTK. Since the concept of an HTK/GCV system was first described, it has shown good success as a tumor ablation strategy in a variety of experimental models. In addition, over two dozen clinical gene therapy trials based on this model have been initiated in the last seven years. See J. A. Roth et al., "Gene therapy for cancer: what have we done and where are we going?" Journal of the National Cancer Institute, vol. 89(1), pp. 21-39 (1997); D. Klatzmann et al., "A Phase I/II dose-escalation study of herpes simplex virus type 1 thymidine kinase "suicide" gene therapy for recurrent metastatic melanoma," Human Gene Therapy, vol. 9, pp. 2585-2894 (1998); and J. R. Herman et al., "In situ gene therapy for adenocarcinoma of the prostate: A phase I clinical trial," Human Gene Therapy, vol. 10, pp. 1239-1249 (1999).

The present invention and the methods described in the applications incorporated herein by reference relate to cells transfected with exogenous genetic material (DNA or RNA) which encodes a clinically useful product that includes proteins, enzymes, hormones, cytokines, antigens, antibodies, enzymes, clotting factors, transport proteins, receptors, regulatory proteins, structural proteins, transcription factors, or anti-sense RNA. Additionally, the methods of the present invention can be used to produce cells, which produce non-naturally occurring ribozymes, proteins, or nucleic acids. The present invention also relates to a method of activating a gene, which is present in cells, but is not normally expressed in the cells or is not expressed at significant levels in the cells. The present invention can be used in homologous recombination or targeting to replace or disable the regulatory region normally associated with the gene with a regulatory sequence which causes the gene to be expressed at levels higher than evident in the corresponding non-transfected cell, or causes the gene to display a pattern of regulation or induction that is different than evident in the corresponding non-transfected cell.

In certain embodiments of the invention, this synthetic promoter embodiment modulates transcription of an exogenous nucleic acid operatively linked to the synthetic promoter by increasing transcription by at least 10%, 25%, or 50% as compared to an endogenous BIRC5 or LAMC2 promoter. In certain embodiments of the invention, the promoter has a minimal size and is at least 200, 300, 400, 500 or 600 nucleotides. In other embodiments of the invention, the promoter has a maximal size and is less than 300, 400, 500, 600 or 700 nucleotides.

Exogenous DNA incorporated into cells by the present method is: DNA which encodes a translation or transcription product whose expression in cells is desired, or a portion of a translation or transcription product, such as a protein product or RNA product useful to treat an existing condition or prevent it from occurring; or DNA which does not encode a gene product but is itself useful, such as a transcriptional regulatory sequence or DNA useful to treat an existing condition or prevent it from occurring. Exogenous DNA can be, for example, a hormone, a cytokine, an antigen, an antibody, an enzyme, a clotting factor, a transport protein, a receptor, a regulatory protein, a structural protein, a transcription factor, an anti-sense RNA, or a ribozyme. Additionally, the product can be a protein or a nucleic acid which does not occur in nature (i.e., a novel protein or novel nucleic acid). The DNA can be obtained from a source in which it occurs in nature or can be produced, using genetic engineering techniques or synthetic processes. The DNA can encode one or more therapeutic products.

DNA constructs (alternatively, nucleic acid constructs), which include exogenous DNA and, optionally, DNA encoding a selectable marker, along with additional sequences necessary for expression of the exogenous DNA in recipient cells, are used to transfect cells in which the encoded product is to be produced. The DNA construct can also include targeting sequences for homologous recombination with host cell DNA. DNA constructs which include exogenous DNA sequences, which do not encode a gene product and, optionally, include DNA encoding a selectable marker. The DNA constructs may be introduced into cells by a variety of methods, including electroporation, microinjection, calcium phosphate precipitation, and liposome- polybrene- or DEAE dextran-mediated transfection, infectious vectors, e.g., retroviral, herpes, adenovirus, adenovirus-associated, mumps and poliovirus vectors, can be used to introduce the DNA. The cells produced by the present invention are useful for in vitro production of therapeutic products, which can be purified and delivered by conventional pharmaceutical routes.

The present invention also provides a delivery system for treating an individual with an abnormal or undesirable condition which responds to delivery of a therapeutic product, which is either: a therapeutic protein (e.g., a protein which is absent, underproduced relative to the individual's physiologic needs, and/or a protein that is defective or inefficiently or inappropriately utilized in the individual, and/or a protein with novel functions, such as enzymatic or transport functions) or a therapeutic nucleic acid (e.g., DNA which binds to or sequesters a regulatory protein, RNA which inhibits gene expression or has intrinsic enzymatic activity).

A nucleic acid construct is directed to a specified target sequence of a nucleic acid molecule encoding a nucleic acid sequence. The nucleic acid sequence may also be directed to a nucleic acid sequence encoding a variant of the protein shown. Variants include naturally occurring allelic variants or non-naturally occurring allelic variants. Such naturally occurring and non-naturally occurring variants include proteins having amino acid deletions, substitutions and additions, as well as fragments, derivatives or analogs.

The present invention includes a nucleic acid construct having a regulatory element or promoter region operably linked to an exogenous DNA or RNA segment. Alternatively, the nucleic acid construct may have a regulatory element operably linked to an exogenous DNA insertion point.

The nucleic acid construct of the present invention may be of any construct known to the skilled artisan that can be introduced into a cell by any of various methods known in the art. For example, a nucleic acid is introduced into a cell via calcium phosphate or calcium chloride co-precipitation-mediated transfection, DEAE-dextran-mediated transfection, liposome-mediated transfection, electroporation and microinjection.

In one embodiment, a method according to the present invention includes a tumor cell with an effective amount of an agent introduced into the tumor cell by the exogenous nucleic acid fragment of the nucleic acid construct controlled by the synthetic promoter. The exogenous nucleic acid fragment can be any exogenous nucleic acid fragment. For example, the exogenous nucleic acid fragment may code for a peptide and protein such as antibodies and peptide aptamers, as well as inhibitory compounds which are not peptides or proteins.

Exogenous nucleic acid fragment may include fragments for RNA interference for inhibiting a selected gene. RNA interference has been characterized in numerous organisms and is known to be mediated by a double-stranded RNA, also termed herein a double-stranded RNA compound.

Briefly described, RNA interference involves a mechanism triggered by the presence of small interfering RNA, siRNA, resulting in degradation of a target complementary mRNA. siRNA is a double-stranded RNA which includes a nucleic acid sequence complementary to a target sequence in the gene to be silenced. The double-stranded RNA may be provided as a long double-stranded RNA compound, in which case it is subject to cleavage by the endogenous endonuclease Dicer in a cell. Cleavage by Dicer results in siRNA duplexes having about 21-23 complementary nucleotides in each of the sense strand and the antisense strand, and optionally 1-2 nucleotides 3' overhangs on each of the two strands. As noted above, further details of siRNA compounds are described in Engelke, D. R., RNA Interference (RNAi): Nuts and Bolts of RNAi Technology, DNA Press LLC, Eagleville, PA, 2003. Additional description of siRNA length and composition is found in Elbashir, S. M. et al., Genes and Devel., 15:188-200, 2001; and O'Toole, A. S. et al., RNA, 11:512-516, 2005.

Embodiments of the invention include expression vectors comprising the promoters disclosed herein. Optionally, the expression vector includes a gene operably linked to control sequences recognized by one or more non-human host cells that can be transformed with the vector (e.g. a Shine-Dalgarno sequence). Related embodiments of the invention include a host cell comprising the expression vectors disclosed herein. Typically, the host cell is an *Escherichia coli*, yeast or human cell. Embodiments of the invention also include methods for expressing an exogenous nucleic acid in one or more cells using an expression vector comprising a synthetic promoter and an exogenous nucleic acid operably linked to the synthetic promoter.

Typically in such embodiments, the synthetic promoter includes at least two copies/repeats of a nucleotide sequence spanning positions −327 to −1 of the human BIRC5/survivin promoter gene (SEQ ID NO: 18) or a nucleotide sequence spanning positions −218 to −32 of the human LAMC2 promoter gene (SEQ ID NO: 21). These methods comprise transforming one or more cells with an expression vector disclosed herein so that this cell expresses an exogenous nucleic acid fragment (e.g. by growing the cell under conditions selected so that the cell transcribes and translates a protein such as thymidine kinase). Optionally, the synthetic promoter further includes at least one of an ATG motif, a nucleotide sequence spanning positions +1 to +128 of the human BIRC5/survivin promoter gene (SEQ ID NO: 20), a nucleotide sequence spanning positions −32 to +1 of the human LAMC2 promoter gene (SEQ ID NO: 22) or an E4 TATA motif. A related embodiment of the invention is a method of transforming a cell by combining the cell with an expression vector comprising a polynucleotide regulatory sequence operably linked to an exogenous nucleic acid sequence so that the cell is transformed with the vector and expresses the exogenous nucleic acid sequence. In illustrative embodiments of the invention, the cell is a mammalian cancer cell, a mammalian stem cell or a cell present in the islets of Langerhans.

In certain embodiments of the invention, the polynucleotide regulatory sequence regulates the expression of the exogenous nucleic acid sequence. Expression of the exogenous nucleic acid sequence is selected to enhance a process for imaging the cell and/or to alter a metabolic process in the cell. In an illustrative embodiment of the invention, the expression vector expresses a gene that facilities a positron emission tomography (PET) or magnetic resonance imaging (MRI) process. In another illustrative working embodiment of the invention, the expression vector encodes a suicide gene under the control of the synthetic promoter which alters the metabolism of the cell.

The present invention provides a pharmaceutical composition that includes a nucleic acid construct according to the present invention and a pharmaceutically acceptable carrier. The term "pharmaceutically acceptable" refers to a material which can be administered to a subject along with a nucleic acid construct composition without causing significant undesirable biological effects and without interacting in a deleterious manner with any other component of the pharmaceutical composition. Pharmaceutical compositions suitable for administration illustratively include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers; diluents; solvents; or vehicles include water, ethanol, polyols such as propylene glycol, polyethylene glycol, glycerol, and the like, and suitable mixtures thereof; vegetable oils such as olive oil; and injectable organic esters such as ethyloleate. Proper fluidity of liquids can be maintained, for example, by the use of a coating such as lecithin, by the maintenance of the required particle size in the case of dispersions, and by the use of surfactants.

Compositions suitable for injection optionally include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity of injectables can be maintained, for example, by the use of a coating such as lecithin, by the maintenance of the required particle size in the case of dispersions and by the use of surfactants.

Pharmaceutical compositions according to the present invention may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of an injectable pharmaceutical form can be brought about by the use of agents delaying absorption, for example, aluminum monostearate and gelatin.

Further exemplary adjuvants include immunostimulating adjuvants such as Freund's complete adjuvant; Freund's incomplete adjuvant; aluminum hydroxide such as commercially available as Alhydrogel, Accurate Chemical & Scientific Co., Westbury, N.Y.; and Gerbu adjuvant, available from C-C Biotech, Poway, Calif.

Solid dosage forms for oral administration include capsules, tablets, pills, powders, and granules. In such solid dosage forms, a nucleic acid construct is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol, and glycerol monostearate; h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like. Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Microencapsulated formulations of a nucleic acid construct are also contemplated.

Liquid dosage forms for oral administration include pharmaceutically acceptable emulsions, solutions, suspensions, syrups, and elixirs. In addition to a nucleic acid construct according to the present invention, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, a pharmaceutical composition according to the present invention can also include adjuvants, such as wetting agents, emulsifying and suspending agents, sweetening, flavoring, and perfuming agents. Suspensions, in addition to a nucleic acid construct, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Further, specific details of pharmaceutical formulation can be found in Pharmaceutical Dosage Forms Tablets, eds. H. A. Lieberman et al. (New York: Marcel Dekker, Inc., 1989), Remington: The Science and Practice of Pharmacy, Lippincott Williams & Wilkins, 21st Ed., 2006; and in L. V. Allen, Jr. et al., Ansel's Pharmaceutical Dosage Forms and Drug Delivery Systems, 8th Ed. (Philadelphia, Pa.: Lippincott, Williams & Wilkins, 2004).

A composition including a nucleic acid construct is optionally delivered in conjunction with a second therapeutic and/or diagnostic agent in one embodiment. An effective amount of a therapeutic and/or diagnostic agent is administered to achieve a therapeutic and/or diagnostic goal, illustratively including amelioration of pain, inflammation, or other signs or symptoms of a particular condition of the subject. A therapeutic and/or diagnostic agent suitable in this regard illustratively includes an analgesic, an antibiotic, an antibody, an antigen, an anti-inflammatory, an anti-tumor agent, an antiviral, a gamma or beta radiation emitting species, an enzyme, and a hormone. The nucleic acid construct composition and second therapeutic and/or diagnostic agent may be administered together in one composition, or separately.

A conjugate of the present invention can be administered to a subject alone or as part of a pharmaceutical composition. Inventive conjugate compositions are suitable for administration to patients by a variety of systemic and local routes illustratively including intravenous, oral, parenteral, intramuscular, topical, subcutaneous and mucosal.

The dosage of an inventive pharmaceutical composition will vary based on factors such as the route of administration; the age, health, and weight of the subject to whom the composition is to be administered; the nature and extent of the subject's symptoms, if any; and the effect desired. Usually a daily dosage of an inventive conjugate is in the range of about 0.001 to 100 milligrams per kilogram of a subject's body weight. A daily dose may be administered as two or more divided doses to obtain the desired effect. An inventive pharmaceutical composition may also be formulated for sustained release to obtain desired results.

It is contemplated that any embodiment discussed in this specification can be implemented with respect to any method, kit, reagent, or composition of the invention, and vice versa. Furthermore, compositions of the invention can be used to achieve methods of the invention.

It will be understood to those of skill in the art that the unique characteristics of the synthetic promoter associated sequences disclosed herein allow them to be adapted for a wide variety of uses. In illustrative embodiments of the invention, the synthetic promoter associated sequences are used for theranostics (combined term for imaging and therapy) for cancer, for diabetes and disorders of glucose regulation, for cell sorting, and for veterinary theranostics.

For example, imaging is an enormous field of healthcare for both human and animals. In this context, the synthetic promoter associated sequences disclosed herein can be used in methods for imaging a number different cell types, for example by driving expression of imaging genes, such as viral thymidine kinase (vTK) and luciferase, the expression of which can be imaged using PET-CT scans, MM, optical imaging etc. In certain embodiments of the invention, the synthetic associated sequences are used in pancreatic cancer and insulinoma tumor cells to drive optical imaging genes, vTK genes, and/or luciferase genes. Gaussia luciferase (GLuc) is a secreted reporter, and its expression in living animals can be assessed by in vivo bioluminescence imaging (BLI) or blood assays. The GLuc levels in the blood can be used to detect tumor growth, metastasis and monitor response to therapy. The combination of a blood assay and in vivo BLI using GLuc may be used for quantifying and localizing the tumors.

EXAMPLES

Example 1: Early Detection of PanIN and PDAC Cells

Pancreatic ductal adenocarcinoma (PDAC) has the poorest survival rate of the common cancers because a lack of efficient early-detection approaches means that most patients are at advanced stages of disease at diagnosis. Present early-detection strategies have insufficient sensitivity/specificity for accurate detection of the precursor lesions like pancreatic intraepithelial neoplasia (PanIN) and early PDAC.

An innovative early detection of PDAC strategy was developed by: 1) identification of early actionable genes (EAGs) from genetically engineered PanIN and early PDAC cell and organoid models, which are unique responders to initial genetic lesions (driver mutations) occurrence in the early onset PDAC; 2) taking advantage of EAGs to generate powerful synthetic promoters (SPs) to drive the expression of unique synthetic blood biomarker—Gaussia Luciferase (GLuc) and imaging biomarkers-sr39 thymidine kinase (sr39TK) only in PanIN and early PDAC; 3) utilizing two steps transcriptional application (TSTA) system to further enhance reporter gene expression; and 4) using potent genetically-engineered $AAV_2$ ($scAAV_2^{GE}$) delivery system to ensure targeting delivery of transgene into PanIN and PDAC cells. This novel detection system is unique and represents a new concept aimed to detect the early genetic lesions (driver mutation) initially presence in the early stage of PDAC by EAG platform. It is more sensitive/specific/precision than existing early detection approaches. The two-step transcriptional activation (TSTA) mechanism in gene therapy amplifies cell type-specific promoter activity, allowing for increased levels of gene expression in target tissues.

Early detection of PanIN and PDAC cells is achieved by detection of synthetic biomarkers that precisely assess the initial genetic events (driver mutations) in early onset PanIN and PDAC. Identification of EAGs in PanIN and early PDAC is reached by: 1) the development of in vitro cell and organoid model to show early-stage PanIN and PDAC by CRISPR/Cas9 engineering human primary pancreatic epithelial cells (HPPE) and pancreatic ductal organoid (ORG); 2) identification of early actionable genes by RNAseq analysis of gene expression profiles; 3) validation of EAGs; and 4) confirmation of the relationship between expression alteration of EAGs and initial oncogenic events (driver mutations).

Generation of unique synthetic blood and imaging biomarkers only in PanIN and early PDAC by multi-layers of enhancing and selecting of reporter gene expression is achieved by: 1) generation of powerful SPs for each EAG (ASP) to ensure highly active and specific in PanIN and early PDAC. BIRC5-SP is one of them to be validated; 2) taking advantage of TSTA system ($ASP^{TSTA}$) to boost the SPs activity without loss of SP's specificity in PanIN and early PDAC; 3) equipment with dual reporter gene GLuc-2A-sr39TK under the control of $ASP^{TSTA}$ enables only PanIN and early PDAC to release synthetic biomarker GLuc and express of sr39TK simultaneously; and 4) establishment of $scAAV_2^{GE}$ delivery system ensures precisely deliver reporter transgenes only in the PanIN and early PDAC cells.

Validation of early detection of PanIN and early PDAC by synthetic biomarker strategies in vivo was performed with animal models used to validate the feasibility of synthetic biomarker strategies including: 1) systemic delivery of $scAAV_2^{GE}$-$ASP^{TSTA}$-GLuc-2a-sr39TK viral particles into $HPPEs^{GE}$ and $ORGs^{GE}$ xenograft mice; and 2) systemic delivery of $scAAV_2^{GE}$-$ASP^{TSTA}$-GLuc-2a-sr39TK viral particles into genetically engineered mouse ($Kras^{G12D}$ and $Kras^{G12D}$/TP53) via tail vein injection. Blood synthetic biomarker GLuc is used to evaluated the sensitivity and specificity of early detection of PanIN and early PDAC. Molecular imaging marker sr39TK provides precise localization of PanIN and PDAC by PET-CT imaging.

These studies provide reliable and precise methods for identifying early actionable genes based on the initial oncogenic events that occur in PanIN and early PDAC cells. Powerful SPs of the EAGs, such as BL-2, coordinated with TSTA system boosted the promoter activity to drive synthetic biomarker expression, GLuc and sr39TK, resulting in enhanced expression and secretion levels that increase sensitivity of detection. SPs of the EAGs, such as BL-2, and scAAV$_2^{GE}$ delivery system ensure synthetic biomarkers are only expressed in the PanIN and early PDAC cells. This platform reveals formerly undetectable initial molecular events by the SPs of early actionable genes. The combination of a multi-stage bio-signal amplification system with a multi-layer barrier selection system ensure highly sensitive and specific detection. This novel detection system benefits high-risk patients and patients with early PDAC.

Early detection of PanIN and early PDAC cells through a platform linking initial genetic molecular changes, related to the early onset of PanIN and PDAC, to early actionable genes is innovative and life-saving. This information may be used to generate powerful synthetic promoters and a transcriptional boosting system to drive screening and localizing dual reporter expression as well as a PanIN and early PDAC targeted delivery system for screening and localization of PanIN and early PDAC lesions.

Figure 8:
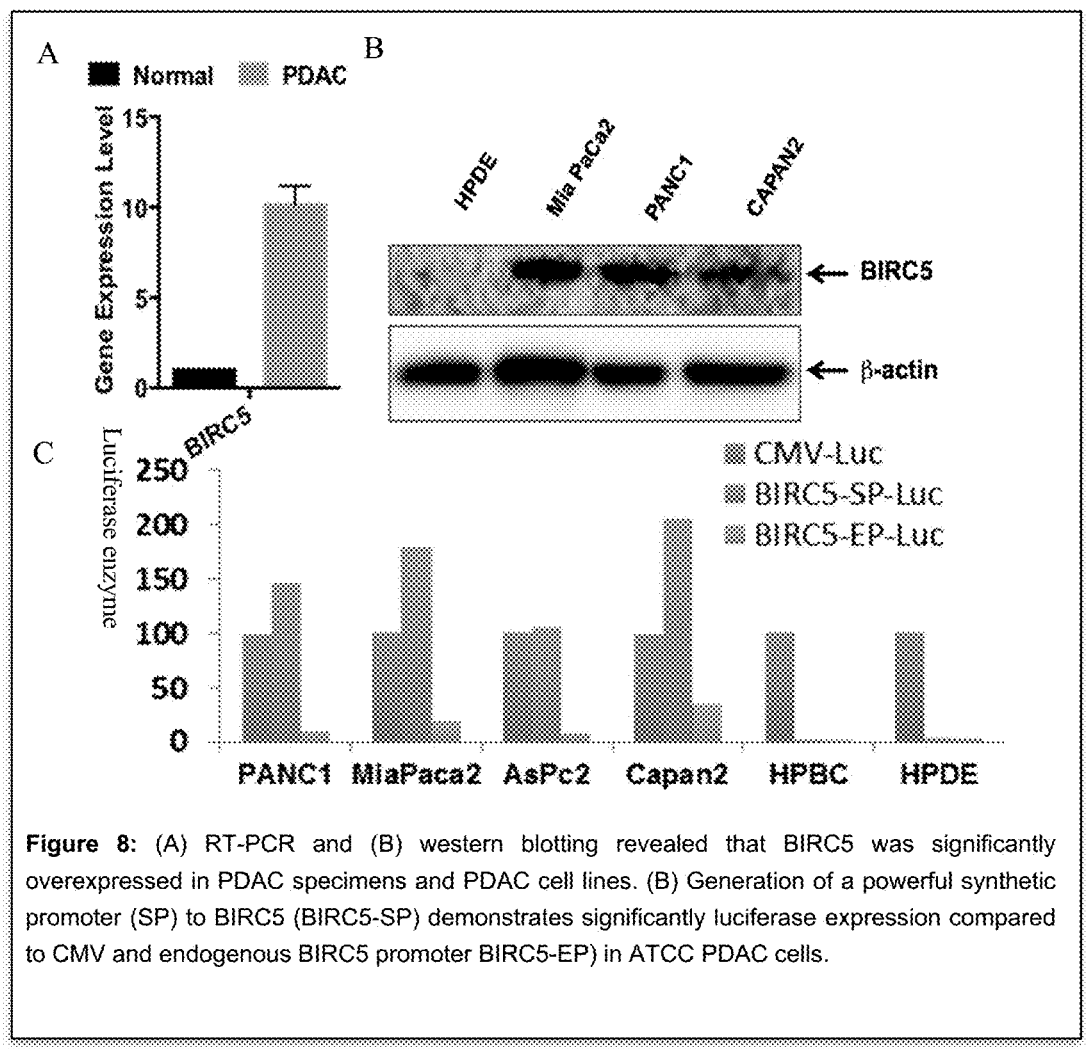
FIGS. 8A-B show RT-PCT (A) and western blotting (B) results revealing that BIRC5 was significantly overexpressed in pancreatic ductal adenocarcinoma (PDAC) specimens and PDAC cell lines.
FIG. 8C is a graph showing the generation of a synthetic promoter to BIRC5 (BIRC5-SP) demonstrates significant luciferase expression compared to a cytomegalovirus (CMV) promoter and an endogenous BIRC5 promoter (BIRC5-EP) in ATCC™ PDAC cells.
Figure 9:
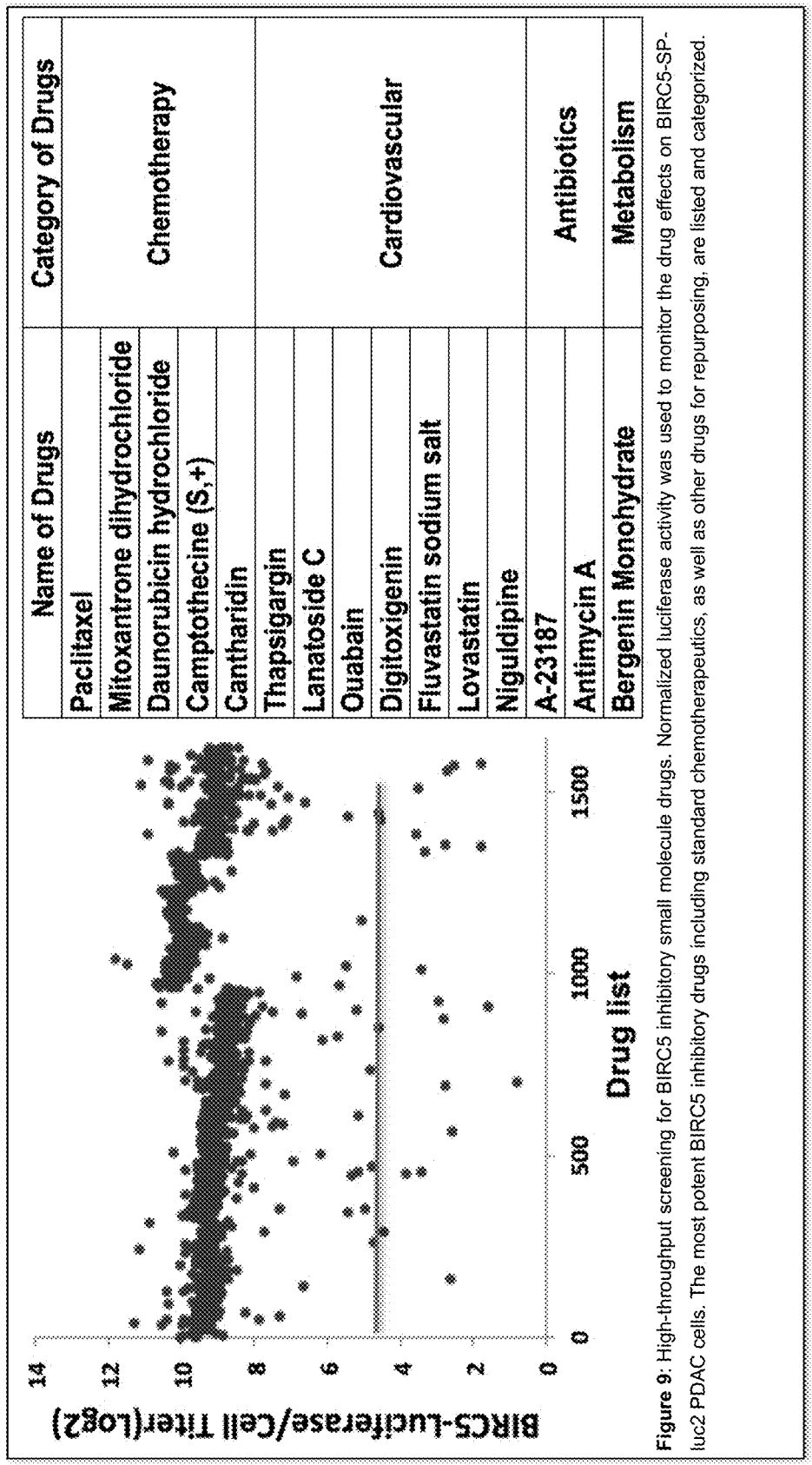
FIG. 9 shows the results of a high-throughput screening for BIRC5 inhibitory small molecule drugs. Normalized luciferase activity was used to monitor the drug effects on BIRC5-SPluc2 PDAC cells. The most potent BIRC5 inhibitory drugs including standard chemotherapeutics, as well as other drugs for repurposing, are listed and categorized.
Figure 10:
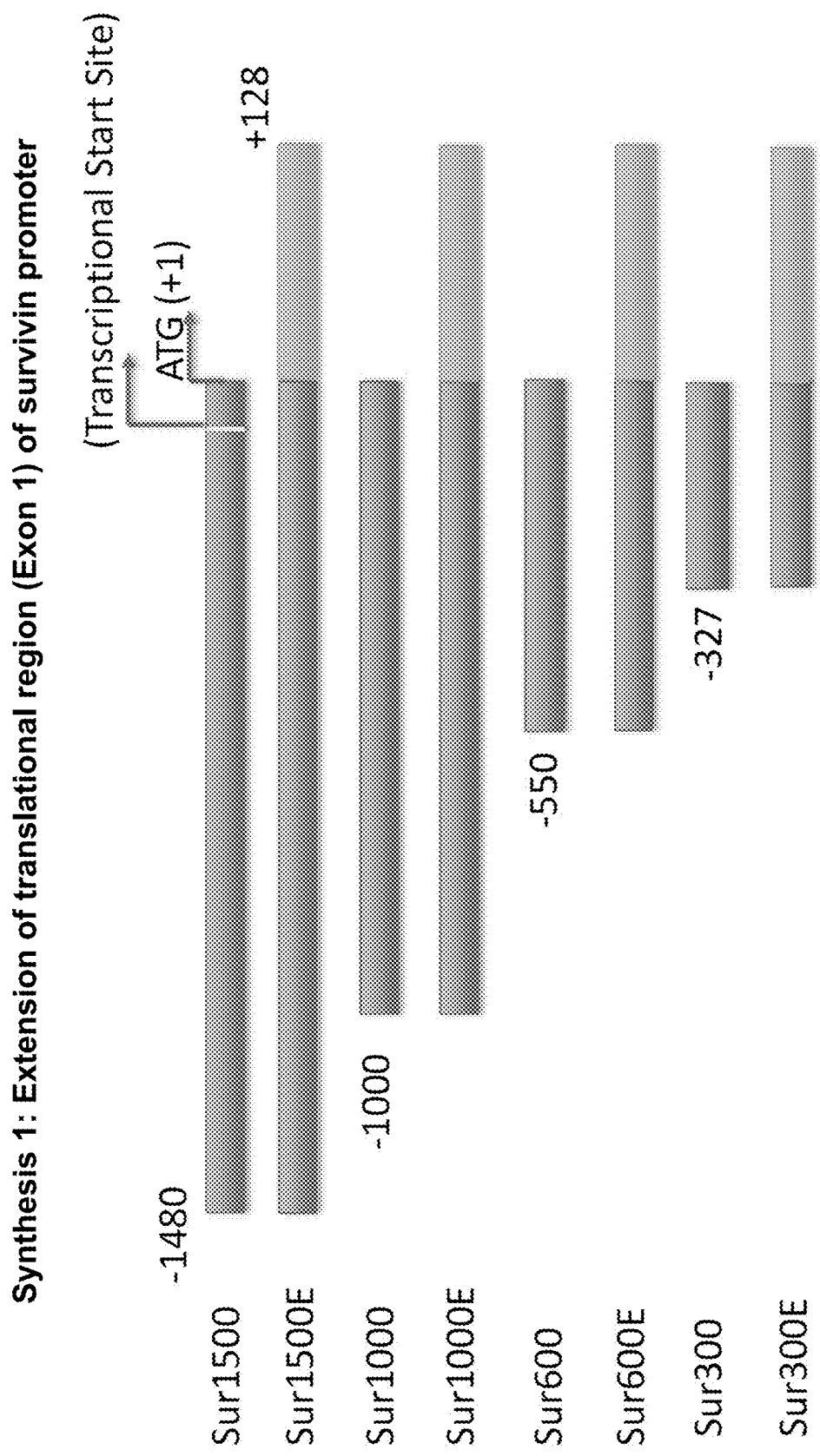
FIG. 10 shows general compositions of different extension variants of the translational region (exon 1) of the survivin promoter, in accordance with one or more embodiments of the invention.
Figure 13:
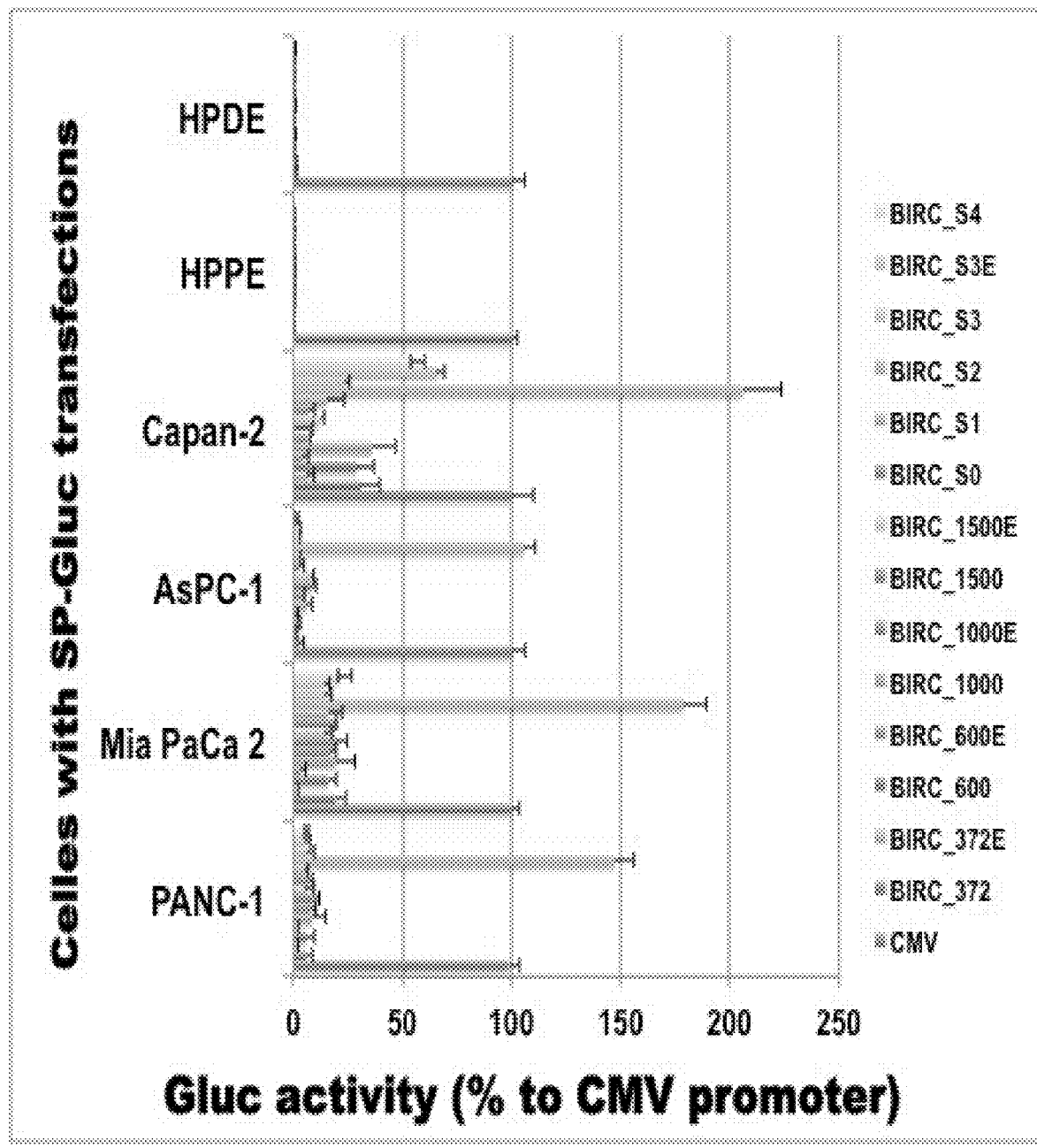
FIG. 13 is a graph showing the results of a BIRC5-SP reporter assay using Gaussia Luciferase (GLuc) on various cell lines, in accordance with one or more embodiments of the invention. BIRC_S2 (BL-2) is shown to result in the greatest amount of GLuc activity in comparison to a CMV promoter.
Figure 14:
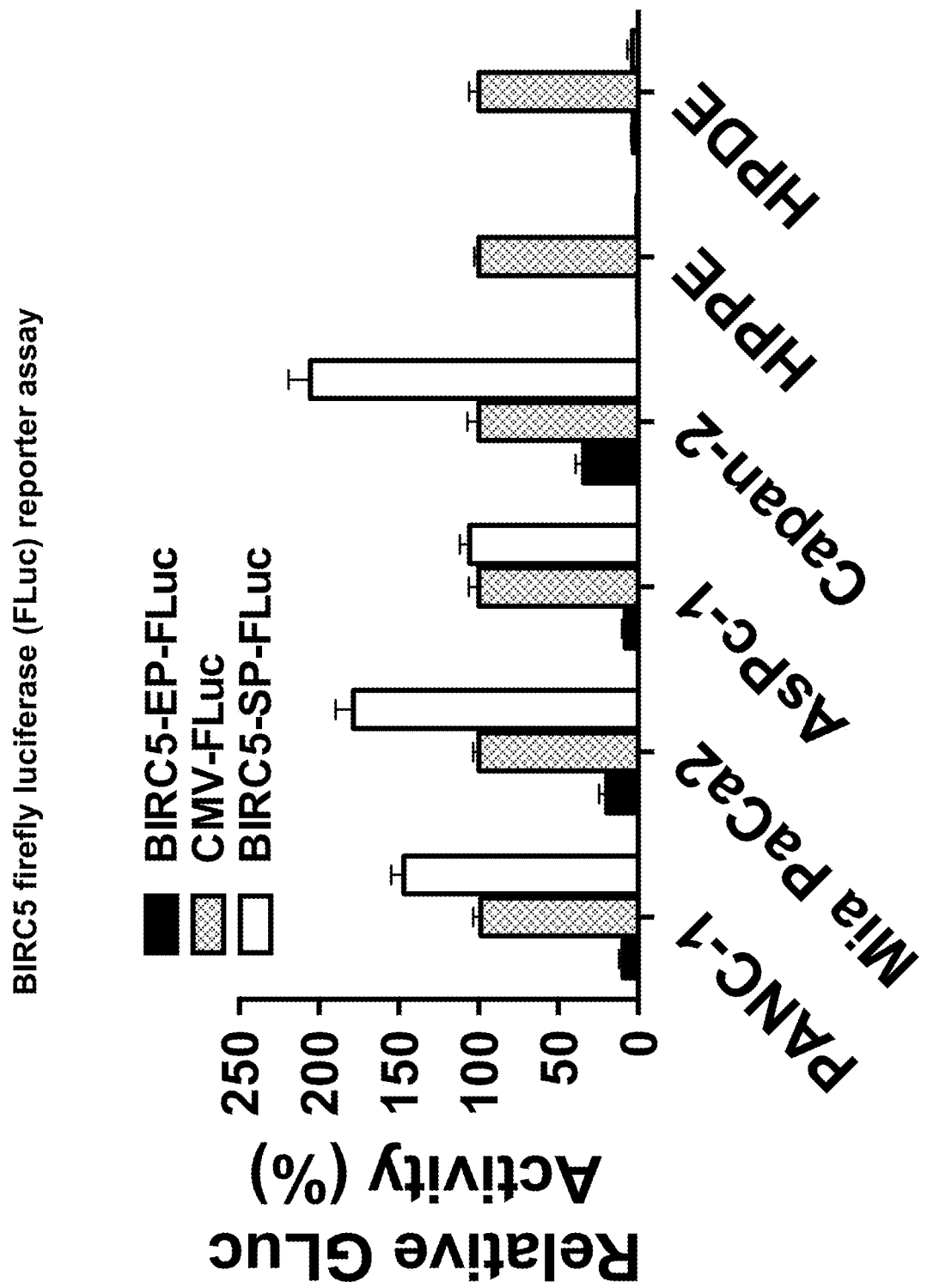
FIG. 14 is a graph showing the results of a BIRC5 firefly luciferase (FLuc) reporter assay on various cell lines, in accordance with one or more embodiments of the invention. BIRC5-SP-FLuc (BL-2) is shown to result in the greatest amount of activity in comparison to an endogenous BIRC5 promoter and a CMV promoter in pancreatic ductal adenocarcinoma cells (PANC-1, MIA PaPc2, AsPc-1, and Capan-2) but no activity in human primary pancreatic epithelial cells (HPPE) and human pancreatic duct epithelial cells (HPPE)
Figure 15:
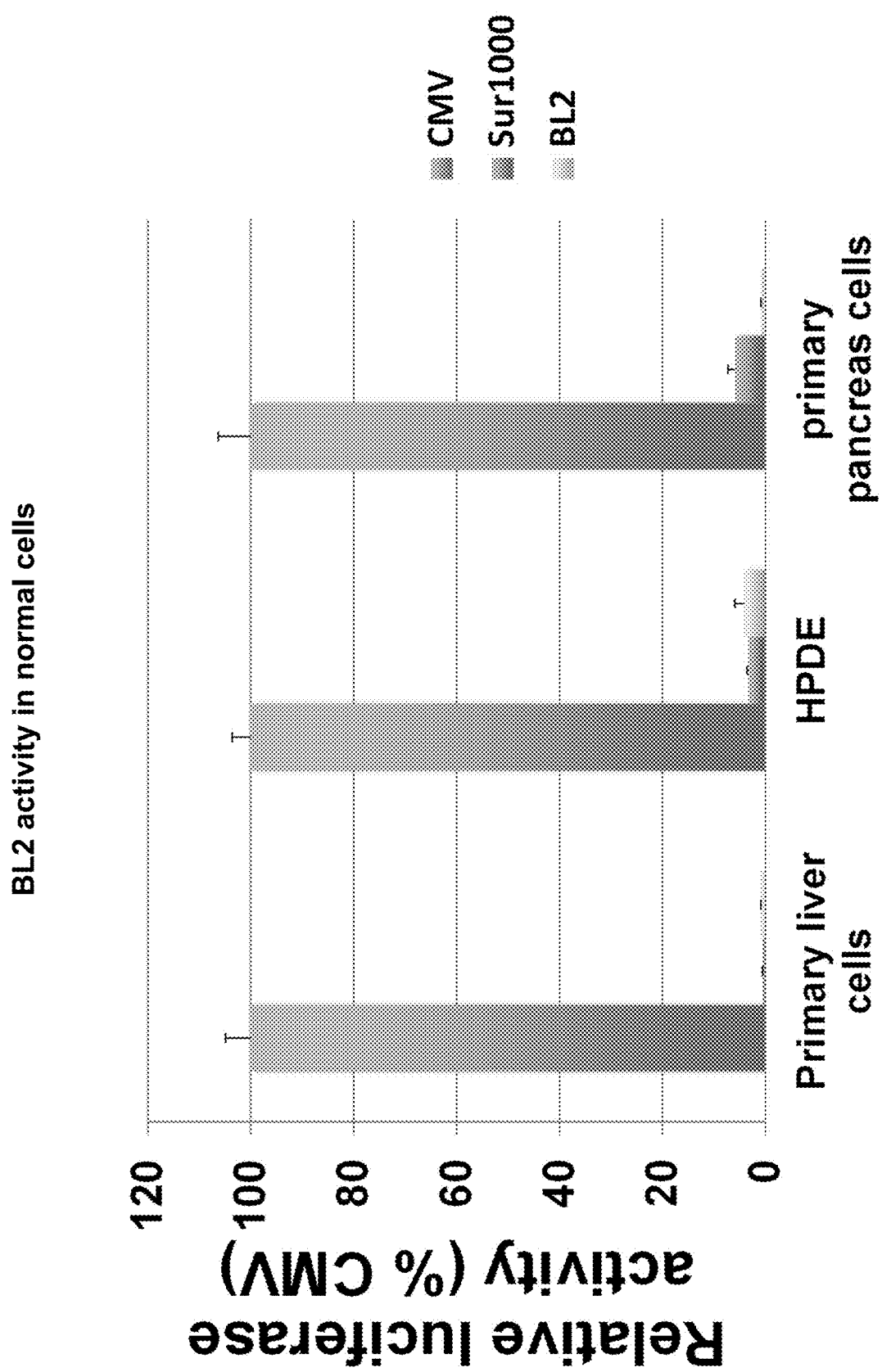
FIG. 15 is a graph showing BL-2 activity in normal cells, in accordance with one or more embodiments of the invention. BL-2 is shown to have very low luciferase activity in normal cells in comparison to a CMV promoter.
Figure 16:
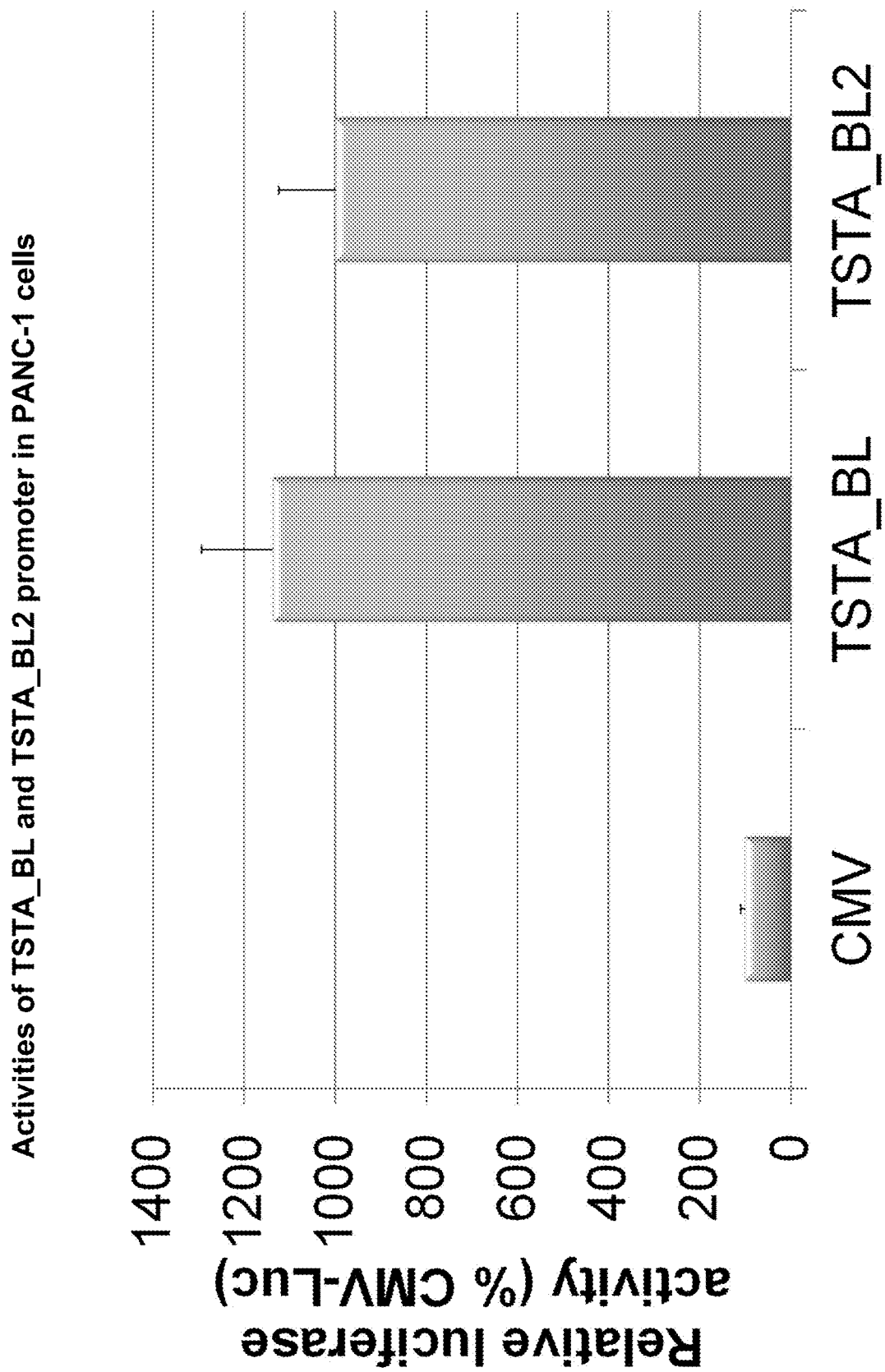
FIG. 16 is a graph showing the activities of synthetic promoters (TSTA_BL and TSTA_BL2) in PANC-1 cells after a two steps transcriptional application (TSTA) system has been applied to further enhance reporter gene expression, in accordance with one or more embodiments of the invention. Compared to a CMV promoter, the synthetic promoters are shown to have very high luciferase activity in PANC-1 cells.
Figure 17:
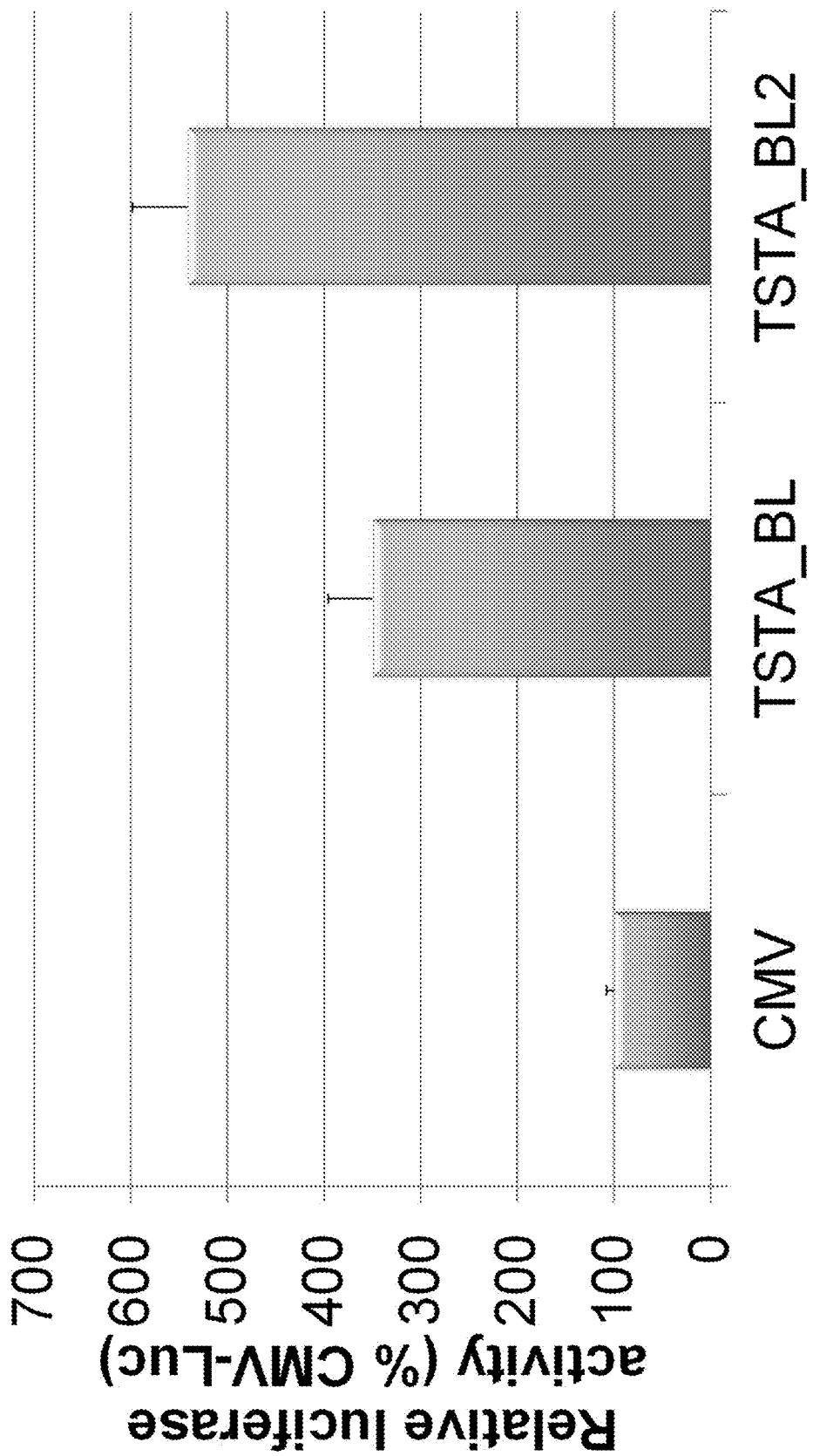
FIG. 17 is a graph showing the activities of synthetic promoters (TSTA_BL and TSTA_BL2) in MIA PaCa-2 cells after a two steps transcriptional application (TSTA) system has been applied to further enhance reporter gene expression, in accordance with one or more embodiments of the invention. Compared to a CMV promoter, the synthetic promoters are shown to have very high luciferase activity in MIA PaCa-2 cells.
Figure 18:
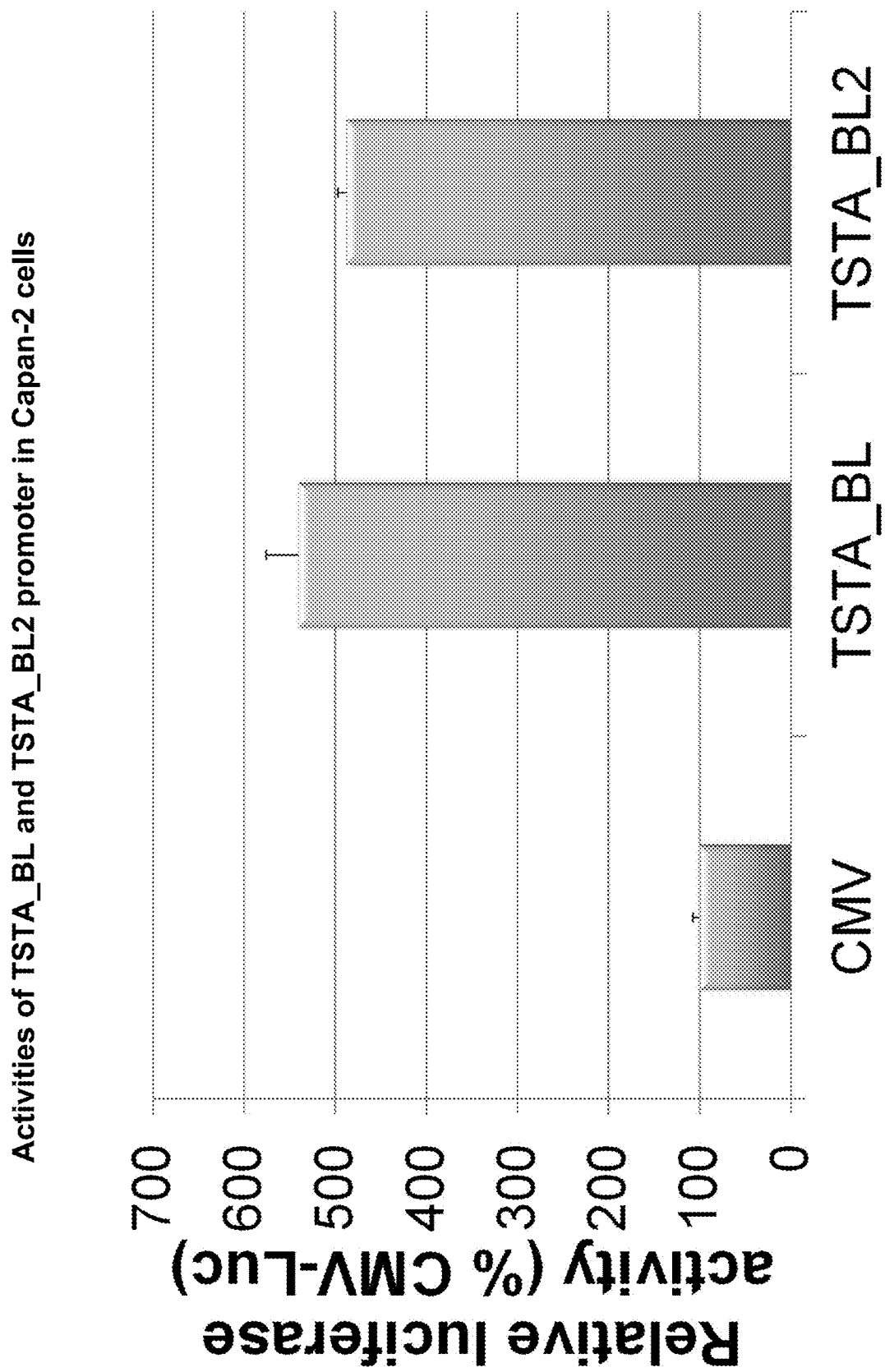
FIG. 18 is a graph showing the activities of synthetic promoters (TSTA_BL and TSTA_BL2) in Capan-2 cells after a two steps transcriptional application (TSTA) system has been applied to further enhance reporter gene expression, in accordance with one or more embodiments of the invention. Compared to a CMV promoter, the synthetic promoters are shown to have very high luciferase activity in Capan-2 cells.
Figure 19:
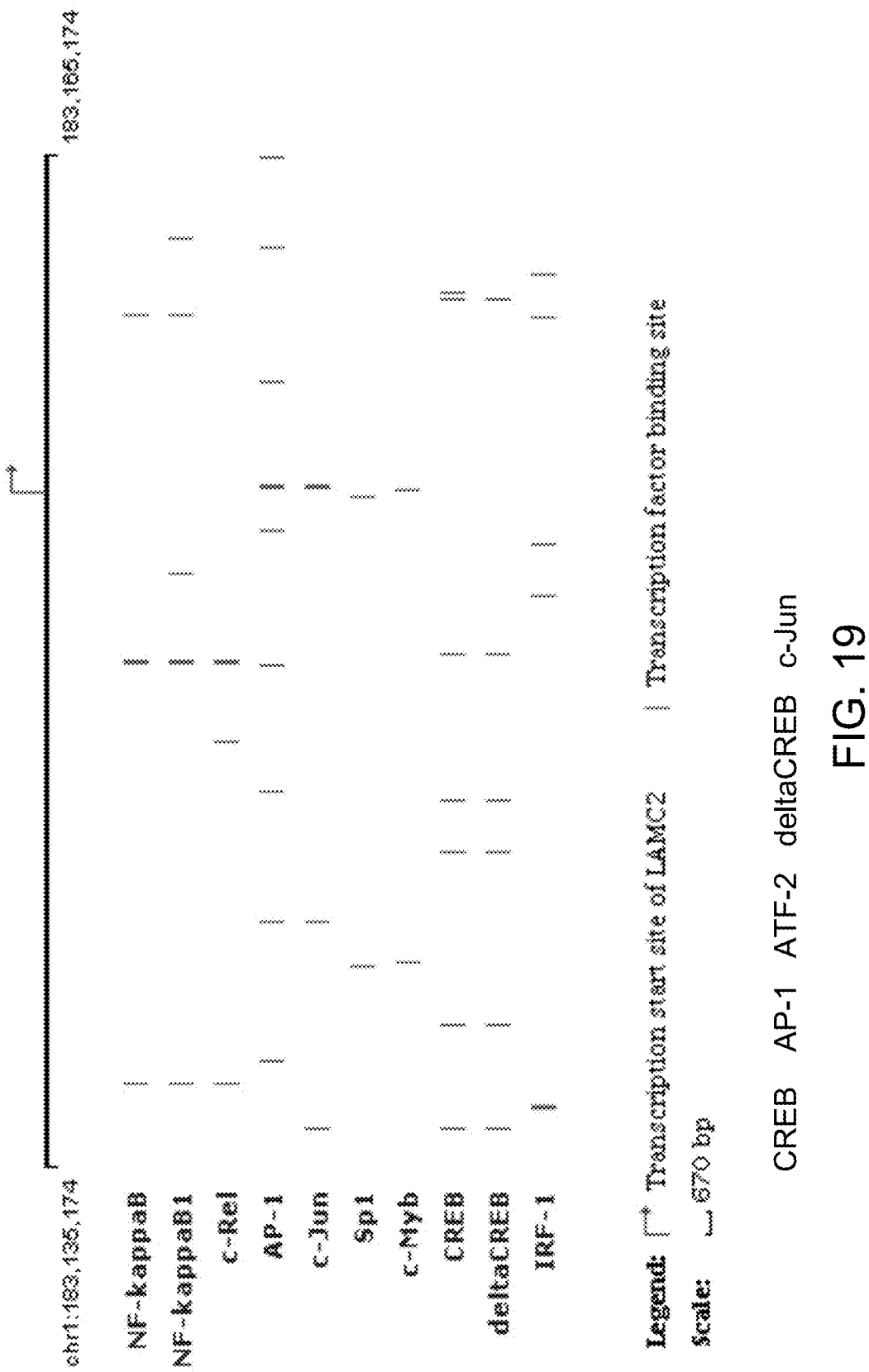
FIG. 19 illustrates the position of various LAMC2 regulatory elements, in accordance with one or more embodiments of the invention.

Example 2: Identification of Novel FDA-Approved Drugs Targeting Actionable Gene (AG) BIRC5 Using BIRC5 Synthetic Promoter-Driven Luciferase in PDAC Cell Lines BIRC5 (survivin) was identified as an rPDAC actionable gene via weighted gene co-expression network analysis (WGCNA) (see, e.g. Langfelder, P. and Horvath, S. (2008) WGCNA: an R package for weighted correlation network analysis. BMC bioinformatics, 9, 559), therefore BIRC5 was chosen as a novel actionable gene (AG) to demonstrate feasibility of the platform. Differentially over-expressed BIRC5 was validated using RT-PCR in rPDAC versus matching non-tumor pancreas (FIG. 8A), as well as western blot assay of ATCC™ PDAC cell lines (FIG. 8B). These preliminary data support the WGCNA that BIRC5 is an actionable gene (AG) for rPDAC. A powerful synthetic promoter for BIRC5, BIRC5-SP (BL-2), was generated (FIG. 8C) and used for BIRC5$^{SP}$-Luc2-Puro stable transfection into MiaPaca2 cells, which in turn were used for high-throughput small molecule screening (HTS) of the FDA-approved drug library. BIRC5$^{SP}$-Luc2-Puro PDAC cells were plated on 384-well plates and 2100 FDA-approved drugs were applied to cells with a pin plate automatic system. Luciferase expression was measured in a plate reader 48 hours after drug administration using Bright-Glo™. Cell viability of treated cells was measured using CellTiter-Glo™. BIRC5-luciferase signal read outs were normalized using cell viability measurements. Inhibitory drugs include daunorubicin and paclitaxel (Kusukawa N, Ishida H, Tanase K, Ito H, Aoki Y, Ooyama N, et al. [Successful treatment with docetaxel and prednisolone for paxlitaxel and carboplatin-resistant prostate cancer]. Hinyokika kiyo Acta urologica *Japonica*. 2013; 59(5):301-4. PubMed PMID: 23719139), as well as other novel rPDAC drugs such as bergenin, simvastatin, fluvastatin (Garwood E R, Kumar A S, Baehner F L, Moore D H, Au A, Hylton N, et al. Fluvastatin reduces proliferation and increases apoptosis in women with high grade breast cancer. Breast cancer research and treatment. 2010; 119(1):137-44. doi: 10.1007/s10549-009-0507-x. PubMed PMID: 19728082; PubMed Central PMCID: PMC4087110; Bocci G, Fioravanti A, Orlandi P, Bernardini N, Collecchi P, Del Tacca M, et al. Fluvastatin synergistically enhances the antiproliferative effect of gemcitabine in human pancreatic cancer MIAPaCa-2 cells. British journal of cancer. 2005; 93(3): 319-30. doi: 10.1038/sj.bjc.6602720. PubMed PMID: 16052215; PubMed Central PMCID: PMC2361561; Zhang J, Nishimoto Y, Tokuda H, Suzuki N, Yasukawa K, Kitdamrongtham W, et al. Cancer chemopreventive effect of bergenin from Peltophorum pterocarpum wood. Chemistry & biodiversity. 2013; 10(10):1866-75. doi: 10.1002/cbdv.201300182. PubMed PMID: 24130029; Fendrich V, Sparn M, Lauth M, Knoop R, Plassmeier L, Bartsch D K, et al. Simvastatin delay progression of pancreatic intraepithelial neoplasia and cancer formation in a genetically engineered mouse model of pancreatic cancer. Pancreatology: official journal of the International Association of Pancreatology. 2013; 13(5):502-7. doi: 10.1016/j.pan.2013.08.002. PubMed PMID: 24075515; Vickers S, Duncan C A, Chen I W, Rosegay A, Duggan D E. Metabolic disposition studies on simvastatin, a cholesterol-lowering prodrug. Drug metabolism and disposition: the biological fate of chemicals. 1990; 18(2):138-45. PubMed PMID: 1971563; Nagata Y, Hidaka Y, Ishida F, Kamei T. Effect of simvastatin (MK-733) on the regulation of cholesterol synthesis in Hep G2 cells. Biochemical pharmacology. 1990; 40(4):843-50. PubMed PMID: 2167097) (FIG. 9). These preliminary data demonstrate that novel PDAC AGs identified by RNA Seq can be matched with AG inhibitory FDA-approved drugs using synthetic promoter-reporter genes for HTS. In summary, the preliminary data presented demonstrate feasibility of the actionable genomics platform.

Example 3: Using Synthetic Promoters for Gene Therapy for Screening, Localization and Therapy of PDAC 83 actionable genes (AGs) have been identified for pancreatic cancer (PDAC) with 12 Hub genes, which are believed to be the most important genes in PDAC. The genes are differentially over expressed proteins in the PDAC tumor compared to the normal matched pancreas. Of the 12 Hub genes, powerful synthetic promoters were created to 2 AGs: BIRC5 (BL-2) and LAMC2 (BL-3). Stably transfected MIA PaCa2 cells were then generated expressing these synthetic promoters driving luciferase and high throughput screening of ~2000 FDA approved drugs was conducted. Stably transfected PANC-1 cells expressing SHIP-luciferase were generated and repeated the high throughput screening to compare the high throughput screening in a second human PDAC cell line.

A weighted gene co-expression network analysis (WGCNA) was performed from the GEO database for 9 major solid cancers and AGs for the 9 cancers were identified. Comparing the AGs for all nine cancers, it was found that 30 AGs that cross all 9 cancers. What is remarkable is that BIRC5 is one of the 30 AGs that cross all 9 cancers.

BIRC5 SP-Gaussia luciferase-2A-sr39thymidine kinase and LAMC2-Gaussia luciferase-2A-sr39thymidine kinase were made and delivered using a designer AAV delivery system. In brief, the Gaussia luciferase and thymidine kinase genes will only be expressed in PDAC cells and secrete Gaussia luciferase into the blood stream and urine. If the Gaussia luciferase is detected in the blood stream or urine, then the patient has to have a pancreas cancer or preclinical PanIn. F-18 FHBG is then used to localize the cancer using PET-CT, since the PDAC cells are expressing thymidine kinase. Ganciclovir or valtrex can then be used to treat the patient since their PDAC are expressing thymidine kinase.

AAV vectors are now considered one of the leading platforms for gene delivery. Recombinant AAV vectors (rAAV) transduce a wide variety of tissues in vivo and provide long-term gene expression with minimal immune responses and no pathological responses in the host. A successful screening system for targeted AAV vectors was developed by displaying peptide ligands directly on the viral capsid, which allows for the selection of improved gene therapy vectors even without prior knowledge of the potential binding receptor and corresponding ligands.

Example 4

Patients with islet neoplasia (INeo) suffer from intractable hypoglycemia. Surgery is the only effective therapy, but is not applicable in many INeo patients and is fraught with complications, therefore effective adjuvant therapy is urgently needed. Somatostatin analogues (SAs) are peptides that have been well described for treatment of INeo, which is often refractory to SAs for unknown reasons; ~20% of INeo patients have a complete response, ~60% have partial response and 20% have no response to SAs. 7-20% of INeo specimens have no expression of somatostatin receptors (SSTR), which might account for the lack of response. We recently demonstrated that SAs/SSTR5 suppresses pancreatic and duodenal homeobox1 (PDX1), which is a regulator of insulin and INeo, suggesting the presence of an SSTR5-PDX1 pathway in INeo. The purposes of this study are to examine the mechanisms of the SSTR5-PDX1 pathway in INeo and to develop adjuvant therapies targeting SSTR5-PDX1 that potentiate the INeo response to SAs.

The following are key findings in this field: 1. Cloning of the mouse Sstr5 gene leading to generation of $Sstr5^{-/-}$ and $Sstr1/5^{-/-}$ mice, which exhibit INeo associated with hyperinsulinemia, hypoglycemia and marked islet PDX1 overexpression, supporting the hypothesis of an SSTR5-PDX1 pathway; 2. the germline human SSTR5 SNP with a proline to leucine substitution at position 335 (SSTR5 P335L) is presented in 35-69% of human INeo specimens, depending on race, and is associated with diminished response to SAs in INeo cells and PDX1 overexpression, suggesting disruption of the SSTR5-PDX1 pathway; and 3. PDX1 regulates INeo and knockdown of PDX1 expression using systemic bifunctional PDX1-shRNA prevents lethal hypoglycemia in INeo mouse models, suggesting that PDX1 is a molecular target for INeo. Exciting preliminary data suggest that 1. our novel synthetic human insulin promoter (SHIP)-SSTR5 gene therapy potentiates the INeo response to SAs, 2. a SHIP-luciferase reporter assay for high throughput screening identified a panel of INeo inhibitory small molecules, including metformin, which potentiate the INeo response to SAs via augmented inhibition of PDX1 and 3. a SSTR5 small molecule agonist potentiates the INeo response to SAs.

Hypotheses:
a) SAs regulate INeo via an SSTR5-PDX1 pathway, b) genomic and expression profiles of SSTR5, $SSTR5^{L335}$ and PDX1 predict response to SAs and c) SSTR5-PDX1 targeted therapies significantly potentiate the INeo response to SAs.

Specific Aim 1:
a) SAs regulate INeo via an SSTR5-PDX1 pathway in INeo cells; b) the pathway is disrupted by $SSTR5^{L335}$ and/or absence of SSTR5 expression with diminished response to SAs in genetically-engineered INeo cells expressing $SSTR5^{L335}$ and/or lacking expression of SSTR5 c) genetic and expression variations of SSTR5 exist in cohorts of INeo specimens and inversely correlate with PDX1 expression levels.

Specific Aim 2:
a) SSTR5 profile predicts INeo response to SAs in i. βTC6 xenograft nude mice, ii. $Sstr1/5^{-/-}$ mice, and/or iii. Pdx1-Cre;Men1$^{flox/flox}$ mice; b) targeted expression of SSTR5 using iv SHIP-SSTR5 in these mouse models significantly potentiates the response to SAs, c) TK expression using SHIP-TK can image response to therapy using $^{18}$F-FHBG microPET imaging in genetically-engineered INeo cells in vitro and in vivo in xenograft nude mice.

Specific Aim 3:
The INeo response to peptide SAs in genetically engineered INeo cells and mouse models is significantly potentiated by a) metformin via augmented inhibition of PDX1, b) bifunctional PDX1 shRNA and/or c) SSTR5 small molecule agonist, L817,818, acting as an SSTR5 binding positive allosteric modulator of SAs.

Expected Outcomes and Impact:
These studies will enhance our understanding of mechanisms of action of SAs in INeo, that SAs regulate INeo via a novel SSTR5-PDX1 pathway and that $SSTR5^{L335}$ or absence of SSTR5 alter responses to SAs. Thus, focused genomic and expression profiles of SSTR5, $SSTR5^{335}$ and PDX1 in INeo will be critically important for the design and evaluation of clinical SAs trials. Selective combination adjuvant therapies targeting the SSTR5-PDX1 pathway via differing molecular mechanisms will significantly potentiate the INeo response to SAs by augmenting the inhibition of PDX1, including metformin and an SSTR5 small molecule, acting as an SSTR5 binding positive allosteric modulator of SAs, which are readily translatable, as well as SHIP-SSTR5 gene therapy and bifunctional PDX1 shRNA. SHIP-TK/$^{18}$F-FHBG microPET imaging can be used as a non-invasive means to image the INeo response to SAs. The information gained from these vertically integrated, translational studies represent personalized medicine and will have important clinical implications for patients suffering with INeo.

SEQUENCE LISTINGS

```
Human BIRC5/survivin Regulatory Sequence (SEQ ID NO: 1)
AAATTGACAT CGGGCCGGGC GCAGTGGCTC ACATCTGTAA TCCCAGCACT
TTGGGAGGCC GAGGCAGGCA GATCACTTGA GGTCAGGAGT TTGAGACCAG
CCTGGCAAAC ATGGTGAAAC CCCATCTCTA CTAAAAATAC AAAAATTAGC
CTGGTGTGGT GGTGCATGCC TTTAATCTCA GCTACTCGGG AGGCTGAGGC
AGGAGAATCG CTTGAACCCG TGGCGGGGAG GAGGTTGCAG TGAGCTGAGA
TCATGCCACT GCACTCCAGC CTGGGCGATA GAGCGAGACT CAGTTTCAAA
TAAATAAATA AACATCAAAA TAAAAAGTTA CTGTATTAAA GAATGGGGGC
GGGGTGGGAG GGGTGGGGAG AGGTTGCAAA AATAAATAAA TAAATAAATA
AACCCCAAAA TGAAAAAGAC AGTGGAGGCA CCAGGCCTGC GTGGGGCTGG
AGGGCTAATA AGGCCAGGCC TCTTATCTCT GGCCATAGAA CCAGAGAAGT
GAGTGGATGT GATGCCCAGC TCCAGAAGTG ACTCCAGAAC ACCCTGTTCC
AAAGCAGAGG ACACACTGAT TTTTTTTTTA ATAGGCTGCA GGACTTACTG
TTGGTGGGAC GCCCTGCTTT GCGAAGGGAA AGGAGGAGTT TGCCCTGAGC
ACAGGCCCCC ACCCTCCACT GGGCTTTCCC CAGCTCCCTT GTCTTCTTAT
CACGGTAGTG GCCCAGTCCC TGGCCCCTGA CTCCAGAAGG TGGCCCTCCT
```

SEQUENCE LISTINGS

```
GGAAACCCAG GTCGTGCAGT CAACGATGTA CTCGCCGGGA CAGCGATGTC
TGCTGCACTC CATCCCTCCC CTGTTCATTT GTCCTTCATG CCCGTCTGGA
GTAGATGCTT TTTGCAGAGG TGGCACCCTG TAAAGCTCTC CTGTCTGACT
TTTTTTTTTT TTTTAGACTG AGTTTTGCTC TTGTTGCCTA GGCTGGAGTG
CAATGGCACA ATCTCAGCTC ACTGCACCCT CTGCCTCCCG GGTTCAAGCG
ATTCTCCTGC CTCAGCCTCC CGAGTAGTTG GGATTACAGG CATGCACCAC
CACGCCCAGC TAATTTTTGT ATTTTTAGTA GAGACAAGGT TTCACCGTGA
TGGCCAGGCT GGTCTTGAAC TCCAGGACTC AAGTGATGCT CCTGCCTAGG
CCTCTCAAAG TGTTGGGATT ACAGGCGTGA GCCACTGCAC CCGGCCTGCA
CGCGTTCTTT GAAAGCAGTC GAGGGGCGC TAGGTGTGGG CAGGGACGAG
CTGGCGCGGC GTCGCTGGGT GCACCGCGAC CACGGGCAGA GCCACGCGGC
GGGAGGACTA CAACTCCCGG CACACCCCGC GCCGCCCCGC CTCTACTCCC
AGAAGGCCGC GGGGGGTGGA CCGCCTAAGA GGGCGTGCGC TCCCGACATG
CCCCGCGGCG CGCCATTAAC CGCCAGATTT GAATCGCGGG ACCCGTTGGC
AGAGGTGGCG GCGGCGGCAT GGGTGCCCCG ACGTTGCCCC CTGCCTGCA
GCCCTTTCTC AAGGACCACC GCATCTCTAC ATTCAAGAAC TGGCCCTTCT
TGGAGGGCTG CGCCTGCACC CCGGAGCGGG TGAGACTGCC CGGCCTCC

Partial Human BIRC5/survivin Regulatory Sequence (SEQ ID NO: 24)
ATTTTTAGTA GAGACAAGGT TTCACCGTGA TGGCCAGGCT GGTCTTGAAC
TCCAGGACTC AAGTGATGCT CCTGCCTAGG CCTCTCAAAG TGTTGGGATT
ACAGGCGTGA GCCACTGCAC CCGGCCTGCA CGCGTTCTTT GAAAGCAGTC
GAGGGGCGC TAGGTGTGGG CAGGGACGAG CTGGCGCGGC GTCGCTGGGT
GCACCGCGAC CACGGGCAGA GCCACGCGGC GGGAGGACTA CAACTCCCGG
CACACCCCGC GCCGCCCCGC CTCTACTCCC AGAAGGCCGC GGGGGGTGGA
CCGCCTAAGA GGGCGTGCGC TCCCGACATG CCCCGCGGCG CGCCATTAAC
CGCCAGATTT GAATCGCGGG ACCCGTTGGC AGAGGTGGCG GCGGCGGCAT
GGGTG BIRC5-S0 (SEQ ID NO: 3)
CCTGCCTAGG CCTCTCAAAG TGTTGGGATT ACAGGCGTGA GCCACTGCAC
CCGGCCTGCA CGCGTTCTTT GAAAGCAGTC GAGGGGCGC TAGGTGTGGG
CAGGGACGAG CTGGCGCGGC GTCGCTGGGT GCACCGCGAC CACGGGCAGA
GCCACGCGGC GGGAGGACTA CAACTCCCGG CACACCCCGC GCCGCCCCGC
CTCTACTCCC AGAAGGCCGC GGGGGGTGGA CCGCCTAAGA GGGCGTGCGC
TCCCGACATG CCCCGCGGGC GTGCGCTCCC GACATGCCCC GCGGCGCGCC
ATTAACCGCC AGATTTGAAT CGCGGGACCC GTTGGCGGCG GCGGCGGCGG
CGGCGGC BIRC5-S1 (SEQ ID NO: 4)
CCTGCCTAGG CCTCTCAAAG TGTTGGGATT ACAGGCGTGA GCCACTGCAC
CCGGCCTGCA CGCGTTCTTT GAAAGCAGTC GAGGGGCGC TAGGTGTGGG
CAGGGACGAG CTGGCGCGGC GTCGCTGGGT GCACCGCGAC CACGGGCAGA
GCCACGCGGC GGGAGGACTA CAACTCCCGG CACACCCCGC GCCGCCCCGC
CTCTACTCCC AGAAGGCCGC GGGGGGTGGA CCGCCTAAGA GGGCGTGCGC
TCCCGACATG CCCCGCCCTG CCTAGGCCTC TCAAAGTGTT GGGATTACAG
GCGTGAGCCA CTGCACCCGG CCTGCACGCG TTCTTTGAAA GCAGTCGAGG
GGGCGCTAGG TGTGGGCAGG GACGAGCTGG CGCGGCGTCG CTGGGTGCAC
CGCGACCACG GGCAGAGCCA CGCGGCGGGA GGACTACAAC TCCCGGCACA
CCCCGCGCCG CCCCGCCTCT ACTCCCAGAA GGCCGCGGGG GGTGGACCGC
CTAAGAGGGC GTGCGCTCCC GACATGCCCC GCGGCGCGCC ATTAACCGCC
AGATTTGAAT CGCGGGACCC GTTGGCAGAG GTGGCGGCGG CGGC BIRC5-S2 (BIRC5-SP) (SEQ ID NO: 5)
CCTGCCTAGG CCTCTCAAAG TGTTGGGATT ACAGGCGTGA GCCACTGCAC
CCGGCCTGCA CGCGTTCTTT GAAAGCAGTC GAGGGGCGC TAGGTGTGGG
CAGGGACGAG CTGGCGCGGC GTCGCTGGGT GCACCGCGAC CACGGGCAGA
GCCACGCGGC GGGAGGACTA CAACTCCCGG CACACCCCGC GCCGCCCCGC
CTCTACTCCC AGAAGGCCGC GGGGGGTGGA CCGCCTAAGA GGGCGTGCGC
TCCCGACATG CCCCGCGGCG CGCCATTAAC CGCCAGATTT GAATCGCGGG
ACCCGTTGGC AGAGGTGGCG GCGGCGGCCC TGCCTAGGCC TCTCAAAGTG
TTGGGATTAC AGGCGTGAGC CACTGCACCC GGCCTGCACG CGTTCTTTGA
AAGCAGTCGA GGGGCGCTA GGTGTGGGCA GGGACGAGCT GGCGCGGCGT
CGCTGGGTGC ACCGCGACCA CGGGCAGAGC CACGCGGCGG GAGGACTACA
ACTCCCGGCA CACCCCGCGC CGCCCCGCCT ACTCCCAG AAGGCCGCGG
GGGTGGACC GCCTAAGAGG GCGTGCGCTC CCGACATGCC CCGCGGCGCG
CCATTAACCG CCAGATTTGA ATCGCGGGAC CGTTGGCAG AGGTGGCGGC
GGCGGC BIRC5-S3 (SEQ ID NO: 6)
CCTGCCTAGG CCTCTCAAAG TGTTGGGATT ACAGGCGTGA GCCACTGCAC
CCGGCCTGCA CGCGTTCTTT GAAAGCAGTC GAGGGGCGC TAGGTGTGGG
CAGGGACGAG CTGGCGCGGC GTCGCTGGGT GCACCGCGAC CACGGGCAGA
GCCACGCGGC GGGAGGACTA CAACTCCCGG CACACCCCGC GCCGCCCCGC
CTCTACTCCC AGAAGGCCGC GGGGGGTGGA CCGCCTAAGA GGGCGTGCGC
TCCCGACATG CCCCGCGGCG CGCCATTAAC CGCCAGATTT GAATCGCGGG
ACCCGTTGGC AGAGGTGGCG GCGGCGGCCC TGCCTAGGCC TCTCAAAGTG
```

TTGGGATTAC AGGCGTGAGC CACTGCACCC GGCCTGCACG CGTTCTTTGA
AAGCAGTCGA GGGGGCGCTA GGTGTGGGCA GGGACGAGCT GGCGCGGCGT
CGCTGGGTGC ACCGCGACCA CGGGCAGAGC CACGCGGCGG GAGGACTACA
ACTCCCGGCA CACCCCGCGC CGCCCCGCCT CTACTCCCAG AAGGCCGCGG
GGGGTGGACC GCCTAAGAGG GCGTGCGCTC CCGACATGCC CCGCGGCGCG
CCATTAACCG CCAGATTTGA ATCGCGGGAC CCGTTGGCAG AGGTGGCGGC
GGCGGCCCTG CCTAGGCCTC TCAAAGTGTT GGGATTACAG GCGTGAGCCA
CTGCACCCGG CCTGCACGCG TTCTTTGAAA GCAGTCGAGG GGCGCTAGG
TGTGGGCAGG GACGAGCTGG CGCGGCGTCG CTGGGTGCAC CGCGACCACG
GGCAGAGCCA CGCGGCGGGA GGACTACAAC TCCCGGCACA CCCCGCGCCG
CCCCGCCTCT ACTCCCAGAA GGCCGCGGGG GGTGGACCGC CTAAGAGGGC
GTGCGCTCCC GACATGCCCC GCGGCGCGCC ATTAACCGCC AGATTTGAAT
CGCGGGACCC GTTGGCAGAG GTGGCGGCGG CGGC

BIRC5-S3E (SEQ ID NO: 7)
CCTGCCTAGG CCTCTCAAAG TGTTGGGATT ACAGGCGTGA GCCACTGCAC
CCGGCCTGCA CGCGTTCTTT GAAAGCAGTC GAGGGGCGC TAGGTGTGGG
CAGGGACGAG CTGGCGCGGC GTCGCTGGGT GCACCGCGAC CACGGGCAGA
GCCACGCGGC GGGAGGACTA CAACTCCCGG CACACCCCGC GCCGCCCCGC
CTCTACTCCC AGAAGGCCGC GGGGGGTGGA CCGCCTAAGA GGGCGTGCGC
TCCCGACATG CCCCGCGGCG CGCCATTAAC CGCCAGATTT GAATCGCGGG
ACCCGTTGGC AGAGGTGGCG GCGGCGGCCC TGCCTAGGCC TCTCAAAGTG
TTGGGATTAC AGGCGTGAGC CACTGCACCC GGCCTGCACG CGTTCTTTGA
AAGCAGTCGA GGGGGCGCTA GGTGTGGGCA GGGACGAGCT GGCGCGGCGT
CGCTGGGTGC ACCGCGACCA CGGGCAGAGC CACGCGGCGG GAGGACTACA
ACTCCCGGCA CACCCCGCGC CGCCCCGCCT CTACTCCCAG AAGGCCGCGG
GGGGTGGACC GCCTAAGAGG GCGTGCGCTC CCGACATGCC CCGCGGCGCG
CCATTAACCG CCAGATTTGA ATCGCGGGAC CCGTTGGCAG AGGTGGCGGC
GGCGGCCCTG CCTAGGCCTC TCAAAGTGTT GGGATTACAG GCGTGAGCCA
CTGCACCCGG CCTGCACGCG TTCTTTGAAA GCAGTCGAGG GGCGCTAGG
TGTGGGCAGG GACGAGCTGG CGCGGCGTCG CTGGGTGCAC CGCGACCACG
GGCAGAGCCA CGCGGCGGGA GGACTACAAC TCCCGGCACA CCCCGCGCCG
CCCCGCCTCT ACTCCCAGAA GGCCGCGGGG GGTGGACCGC CTAAGAGGGC
GTGCGCTCCC GACATGCCCC GCGGCGCGCC ATTAACCGCC AGATTTGAAT
CGCGGGACCC GTTGGCAGAG GTGGCGGCGG CGGCGGTGCC CCGACGTTGC
CCCCTGCCTG GCAGCCCTTT CTCAAGGACC ACCGCATCTC TACATTCAAG
AACTGGCCCT TCTTGGAGGG CTGCGCCTGC ACCCCGGAGC GGGTGAGACT
GCCCGGCCTC C

BICR5-S4 (SEQ ID NO: 8)
CCTGCCTAGG CCTCTCAAAG TGTTGGGATT ACAGGCGTGA GCCACTGCAC
CCGGCCTGCA CGCGTTCTTT GAAAGCAGTC GAGGGGCGC TAGGTGTGGG
CAGGGACGAG CTGGCGCGGC GTCGCTGGGT GCACCGCGAC CACGGGCAGA
GCCACGCGGC GGGAGGACTA CAACTCCCGG CACACCCCGC GCCGCCCCGC
CTCTACTCCC AGAAGGCCGC GGGGGGTGGA CCGCCTAAGA GGGCGTGCGC
TCCCGACATG CCCCGCGGCG CGCCATTAAC CGCCAGATTT GAATCGCGGG
ACCCGTTGGC AGAGGTGGCG GCGGCGGCCC TGCCTAGGCC TCTCAAAGTG
TTGGGATTAC AGGCGTGAGC CACTGCACCC GGCCTGCACG CGTTCTTTGA
AAGCAGTCGA GGGGGCGCTA GGTGTGGGCA GGGACGAGCT GGCGCGGCGT
CGCTGGGTGC ACCGCGACCA CGGGCAGAGC CACGCGGCGG GAGGACTACA
ACTCCCGGCA CACCCCGCGC CGCCCCGCCT CTACTCCCAG AAGGCCGCGG
GGGGTGGACC GCCTAAGAGG GCGTGCGCTC CCGACATGCC CCGCGGCGCG
CCATTAACCG CCAGATTTGA ATCGCGGGAC CCGTTGGCAG AGGTGGCGGC
GGCGGCCCTG CCTAGGCCTC TCAAAGTGTT GGGATTACAG GCGTGAGCCA
CTGCACCCGG CCTGCACGCG TTCTTTGAAA GCAGTCGAGG GGCGCTAGG
TGTGGGCAGG GACGAGCTGG CGCGGCGTCG CTGGGTGCAC CGCGACCACG
GGCAGAGCCA CGCGGCGGGA GGACTACAAC TCCCGGCACA CCCCGCGCCG
CCCCGCCTCT ACTCCCAGAA GGCCGCGGGG GGTGGACCGC CTAAGAGGGC
GTGCGCTCCC GACATGCCCC GCGGCGCGCC ATTAACCGCC AGATTTGAAT
CGCGGGACCC GTTGGCAGAG GTGGCGGCGG CGGCCCTGCC TAGGCCTCTC
AAAGTGTTGG GATTACAGGC GTGAGCCACT GCACCCGGCC TGCACGCGTT
CTTTGAAAGC AGTCGAGGGG GCGCTAGGTG TGGGCAGGGA CGAGCTGGCG
CGGCGTCGCT GGGTGCACCG CGACCACGGG CAGAGCCACG CGGCGGGAGG
ACTACAACTC CCGGCACACC CCGCGCCGCC CCGCCTCTAC TCCCAGAAGG
CCGCGGGGGG TGGACCGCCT AAGAGGGCGT GCGCTCCCGA CATGCCCCGC
GGCGCGCCAT TAACCGCCAG ATTTGAATCG CGGGACCCGT TGGCAGAGGT
GGCGGCGGCG GC

LAMC2 (SEQ ID NO: 9)
CAAAGCCTTC TTGACAGCCA CCTCTCTGAA TTATTGTCAC TAGCCTCCTT
AGGAGAAGAG ACAATATAGT TTATACCAAG ATTTGCAGTT GTCTAGATAT
TACTCACTTC AGCTAGCACT GTGCTAGTAG ATAACATTCA AAGTTGGTCT
CAACAAATAT TTTCTCTAGT GCCCATGGAG AGTGGCTGAG AAATACACTC
TAAGATGTAA AAGAGTTTGG TATCTAGATC CTCTTTCTTA TTCATTTCAA
GCCAATATTT ATTAAGCACC AACTGCAAGC TAGATACTAT TATAGTTAGG
AATATAAAGT GGGCCAGGGA TGGTGTTTAT GCCTATAATC CCAGCACTTT
GGGAGGCCAA GGCAGGAGGA TTACTTGAGG CCAGGAATTC AAGGTCAGCC

```
TGCCCAACAC AGCAAGACCT CGTCTCTACA AAAAATTAAA AAATTAGCTG
GGTGTGGTGG CATTTGCCTG TAGCCCTAGC TACTCAAGAG GCTGAGGTGG
GAGGATTGCT TGAGCCCAGG GGTTGGAGGC TGCAGTGCGC TATGATGGTG
CCATTGAAAA CAAAAACAAA AACCAACCAA CAAACAAAAA AACAAACAAA
AAGAAAACGA TACTCAGTCT TTATAGGGAG GTTGGCCAGT CAATAGGTTA
CTTTATGAGT TGCTAACCCT GGTGAGCAGG AAGTTATGTG GACCAGGAGA
GAAACCCTTG GTTCAGCCTG GAGAAAGGAG AGGTTGACCC TAAACTGGAG
GGTGGAGAGG ACCCTGTTGT GACTCTCCGA CTGACTTGTC TTCCTTGATG
TCCTTTAAGC CGGAGCTGAT TCGGGCTGCT GCCTTATTTC TGAGTTAGCG
CTCTTAAGAT TGGGCCTCCC AGTTTGAGGA AGGGGCGGGC TGCTGTCTAC
CTCTGTGAAT CTGCCCTGGA CCACCCCGGG AGAGAAGGAG GGCTCCGGGG
AATCTCGCAC ATTCCAGGCA AAGGCTCCCG GGCCGCAGCC TCTGTGCCAC
ACCCTTGGCC CGGGCCAGGT GTGCGCCCTC CTCGCTGCGA GGGGGAGCGG
GCGGCTGCGG GGAGCGATTT TCCAGCCCGG TTTGTGCTCT GTGTGTTTGT
CTGCCTCTGG AGGGCTGGGT CCTCCTTATT CACAGGTGAG TCACACCCTG
AAACACAGGC TCTCTTCCTG TCAGGACTGA GTCAGGTAGA AGAGTCGATA
AAACCACCTG ATCAAGGAAA AGGAAGGCAC AGCGGAGCGC AGAGTGAGAA
CCACCAACCG

LAMS1 (SEQ ID NO: 10)
CGGGCCAGGT GTGCGCCCTC CTCGCTGCGA GGGGGAGCGG GCGGCTGCGG
GGAGCGATTT TCCAGCCCGG TTTGTGCTCT GTGTGTTTGT CTGCCTCTGG
AGGGCTGGGT CCTCCTTATT CACAGGTGAG TCACACCCTG AAACACAGGC
TCTCTTCCTG TCAGGACTGA GTCAGGTAGA AGAGTCGTGC GCCCTCCTCG
CTGCGAGGGG GAGCGGGCGG CTGCGGGGAG CGATTTTCCA GCCCGGTTTG
TGCTCTGTGT GTTTGTCTGC CTCTGGAGGG CTGGGTCCTC CTTATTCACA
GGTGAGTCAC ACCCTGAAAC ACAGGCTCTC TTCCTGTCAG GACTGAGTCA
GGTAGAAGAG TCGTGCGCCC TCCTCGCTGC GAGGGGGAGC GGGCGGCTGC
GGGGAGCGAT TTTCCAGCCC GGTTTGTGCT CTGTGTGTTT GTCTGCCTCT
GGAGGGCTGG GTCCTCCTTA TTCACAGGTG AGTCACACCC TGAAACACAG
GCTCTCTTCC TGTCAGGACT GAGTCAGGTA GAAGAGTCAA GCTTATAAAA
CCACCTGATC AAGGAAAAGG AAGGCACAGC GGAGCGCAGA GTGAGAACCA
CCAACCGGAA TTC

LAMS1: (SEQ ID NO: 11)
CGGTCGGGCC AGGTGTGCGC CCTCCTCGCT GCGAGGGGGA GCGGGCGGCT
GCGGGGAGCG ATTTTCCAGC CCGGTTTGTG CTCTGTGTGT TTGTCTGCCT
CTGGAGGGCT GGGTCCTCCT TATTCACAGG TGAGTCACAC CCTGAAACAC
AGGCTCTCTT CCTGTCAGGA CTGAGTCAGG TAGAAGAGTC GTGCGCCCTC
CTCGCTGCGA GGGGGAGCGG GCGGCTGCGG GGAGCGATTT TCCAGCCCGG
TTTGTGCTCT GTGTGTTTGT CTGCCTCTGG AGGGCTGGGT CCTCCTTATT
CACAGGTGAG TCACACCCTG AAACACAGGC TCTCTTCCTG TCAGGACTGA
GTCAGGTAGA AGAGTCGTGC GCCCTCCTCG CTGCGAGGGG GAGCGGGCGG
CTGCGGGGAG CGATTTTCCA GCCCGGTTTG TGCTCTGTGT GTTTGTCTGC
CTCTGGAGGG CTGGGTCCTC CTTATTCACA GGTGAGTCAC ACCCTGAAAC
ACAGGCTCTC TTCCTGTCAG GACTGAGTCA GGTAGAAGAG TCAAGCTTAT
AAAACCACCT GATCAAGGAA AAGGAAGGCA CAGCGGAGCG CAGAGTGAGA
ACCACCAACC G

LAMS2 (SEQ ID NO: 12)
CGGGCCAGGT GTGCGCCCTC CTCGCTGCGA GGGGGAGCGG GCGGCTGCGG
GGAGCGATTT TCCAGCCCGG TTTGTGCTCT GTGTGTTTGT CTGCCTCTGG
AGGGCTGGGT CCTCCTTATT CACAGGTGAG TCACACCCTG AAACACAGGC
TCTCTTCCTG TCAGGACTGA GTCAGGTAGA AGAGTCCAAC TCCCGGCACA
CCCCGCGCCG CCCCGCCTCT ACTCCCAGAA GGCCGCGGGG GGTGGACCGC
CTAAGAGGGC GTGCGCTCCC GACATGCCCC GCGGCGCGCC ATTAACCGCC
AGATTTGAAT CGCGGGACCC GTTGGCAGAG GTGGCGGCGG CGGC

LAMS2: (SEQ ID NO: 13)
CGGTCGGGCC AGGTGTGCGC CCTCCTCGCT GCGAGGGGGA GCGGGCGGCT
GCGGGGAGCG ATTTTCCAGC CCGGTTTGTG CTCTGTGTGT TTGTCTGCCT
CTGGAGGGCT GGGTCCTCCT TATTCACAGG TGAGTCACAC CCTGAAACAC
AGGCTCTCTT CCTGTCAGGA CTGAGTCAGG TAGAAGAGTC CAACTCCCGG
CACACCCCGC GCCGCCCCGC CTCTACTCCC AGAAGGCCGC GGGGGGTGGA
CCGCCTAAGA GGGCGTGCGC TCCCGACATG CCCCGCGGCG CGCCATTAAC
CGCCAGATTT GAATCGCGGG ACCCGTTGGC AGAGGTGGCG GCGGCGGC

LAMS3 (SEQ ID NO: 14)
ACTAGTACCG GTCAACTCCC GGCACACCCC GCGCCGCCCC GCCTCTACTC
CCAGAAGGCC GCGGGGGGTG GACCGCCTAA GAGGGCGTGC GCTCCCGACA
TGCCCCGCGG CGCGCCATTA ACCGCCAGAT TTGAATCGCG GGACCCGTTG
GCAGAGGTGG CGGCGGCGGC CGGGCCAGGT GTGCGCCCTC CTCGCTGCGA
GGGGGAGCGG GCGGCTGCGG GGAGCGATTT TCCAGCCCGG TTTGTGCTCT
GTGTGTTTGT CTGCCTCTGG AGGGCTGGGT CCTCCTTATT CACAGGTGAG
TCACACCCTG AAACACAGGC TCTCTTCCTG TCAGGACTGA GTCAGGTAGA
AGAGTCAAGC TT
```

SEQUENCE LISTINGS

LAMS3: (SEQ ID NO: 15)
CGGTCAACTC CCGGCACACC CCGCGCCGCC CCGCCTCTAC TCCCAGAAGG
CCGCGGGGGG TGGACCGCCT AAGAGGGCGT GCGCTCCCGA CATGCCCCGC
GGCGCGCCAT TAACCGCCAG ATTTGAATCG CGGGACCCGT TGGCAGAGGT
GGCGGCGGCG GCCGGGCCAG GTGTGCGCCC TCCTCGCTGC GAGGGGGAGC
GGGCGGCTGC GGGGAGCGAT TTTCCAGCCC GGTTTGTGCT CTGTGTGTTT
GTCTGCCTCT GGAGGGCTGG GTCCTCCTTA TTCACAGGTG AGTCACACCC
TGAAACACAG GCTCTCTTCC TGTCAGGACT GAGTCAGGTA GAAGAGTCAA
GCTT

EGR1 Binding Site (SEQ ID NO: 16)
GAGGGGGCG

P53 Binding Site (SEQ ID NO: 17)
GGGCGTGCGC TCCCGACATG CCC

Positions -327 to -1 of Human BIRC5/Survivin Promoter (SEQ ID NO: 18)
CCTGCCTAGG CCTCTCAAAG TGTTGGGATT ACAGGCGTGA GCCACTGCAC
CCGGCCTGCA CGCGTTCTTT GAAAGCAGTC GAGGGGGCGC TAGGTGTGGG
CAGGGACGAG CTGGCGCGGC GTCGCTGGGT GCACCGCGAC CACGGGCAGA
GCCACGCGGC GGGAGGACTA CAACTCCCGG CACACCCCGC GCCGCCCCGC
CTCTACTCCC AGAAGGCCGC GGGGGGTGGA CCGCCTAAGA GGGCGTGCGC
TCCCGACATG CCCCGCGGCG CGCCATTAAC CGCCAGATTT GAATCGCGGG
ACCCGTTGGC AGAGGTGGCG GCGGCGGC Positions -99 to +59 of Human BIRC5/Survivin Promoter (SEQ ID NO: 19)
CGGTCAACTC CCGGCACACC CCGCGCCGCC CCGCCTCTAC TCCCAGAAGG
CCGCGGGGGG TGGACCGCCT AAGAGGGCGT GCGCTCCCGA CATGCCCCGC
GGCGCGCCAT TAACCGCCAG ATTTGAATCG CGGGACCCGT TGGCAGAGGT
GGCGGCGGCG GC Positions +1 to +128 of Human BIRC5/Survivin Promoter (SEQ ID NO: 20)
ATGGGTGCCC CGACGTTGCC CCCTGCCTGG CAGCCCTTTC TCAAGGACCA
CCGCATCTCT ACATTCAAGA ACTGGCCCTT CTTGGAGGGC TGCGCCTGCA
CCCCGGAGCG GGTGAGACTG CCCGGCCTCC Positions -218 to -32 of Human LAMC2 Promoter (SEQ ID NO: 21)
CGGGCCAGGT GTGCGCCCTC CTCGCTGCGA GGGGGAGCGG GCGGCTGCGG
GGAGCGATTT TCCAGCCCGG TTTGTGCTCT GTGTGTTTGT CTGCCTCTGG
AGGGCTGGGT CCTCCTTATT CACAGGTGAG TCACACCCTG AAACACAGGC
TCTCTTCCTG TCAGGACTGA GTCAGGTAGA AGAGTC Positions -32 to +1 of Human LAMC2 Promoter (SEQ ID NO: 22)
GATAAAACCA CCTGATCAAG GAAAAGGAAG GCA

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. It will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The invention claimed is:

1. A nucleic acid comprising:
   a synthetic BIRC5 promoter having two or more nucleotide sequence motifs selected from:
   a site at which mRNA transcription is initiated comprising GGC (of SEQ ID NO: 1);
   a SP1 motif comprising GGC (residues 1410-1412 of SEQ ID NO: 1);
   a CDE motif comprising GCC (residues 1300-1302 of SEQ ID NO: 1);
   an EGR1 motif comprising GGG (residues 1223-1225 of SEQ ID NO: 1);
   a p53 motif comprising TCC (residues 1391-1393 of SEQ ID NO: 1);
   an E2F/Rb motif comprising CCC (residues 1401-1403 of SEQ ID NO: 1); wherein:
   the nucleotide sequence motifs are separated by 0 to 50 nucleotides;
   the synthetic BIRC5 promoter comprises SEQ ID NO: 24;
   the synthetic BIRC5 promoter comprises less than 500 nucleotides;
   and
   the synthetic BIRC5 promoter is operatively linked to a heterologous nucleic acid sequence.

2. The nucleic acid of claim 1, wherein the heterologous nucleic acid encodes a naturally occurring polypeptide.

3. The nucleic acid of claim 1, wherein the synthetic BIRC5 promoter exhibits at least a 80% sequence identity to the 100 nucleotides immediately upstream of the transcription start site of the BIRC5 gene.

4. An expression vector comprising the nucleic acid of claim 1.

5. A host cell comprising the vector of claim 4.

6. The host cell of claim 5 wherein the cell is an *Escherichia coli*, yeast or human cancer cell.

7. A composition of matter comprising the nucleic acid of claim 1 and a pharmaceutically acceptable carrier.

8. A nucleic acid comprising:
a synthetic BIRC5 promoter consisting essentially of the nucleotide sequence of SEQ ID NO: 24; wherein:
the synthetic BIRC5 promoter is operatively linked to a heterologous
nucleic acid sequence.

9. The nucleic acid of claim 8, wherein the heterologous nucleic acid encodes a polypeptide.

10. An expression vector comprising the nucleic acid of claim 8.

11. A host cell comprising the expression vector of claim 10.

12. The host cell of claim 11 wherein the cell is an *Escherichia coli*, yeast or human cancer cell.

13. A composition of matter comprising the nucleic acid of claim 8 and a pharmaceutically acceptable carrier.

* * * * *